US009717627B2

(12) United States Patent
Kuzma et al.

(10) Patent No.: US 9,717,627 B2
(45) Date of Patent: Aug. 1, 2017

(54) IMPLANT DELIVERY DEVICES, SYSTEMS, AND METHODS

(71) Applicant: Oculeve, Inc., South San Francisco, CA (US)

(72) Inventors: Janusz Kuzma, Bayview (AU); Douglas Michael Ackermann, San Francisco, CA (US); Christopher William Stivers, San Francisco, CA (US)

(73) Assignee: Oculeve, Inc., South San Francisco, CA (US)

( * ) Notice: Subject to any disclaimer, the term of this patent is extended or adjusted under 35 U.S.C. 154(b) by 0 days.

(21) Appl. No.: 14/207,072

(22) Filed: Mar. 12, 2014

(65) Prior Publication Data

US 2014/0277429 A1 Sep. 18, 2014

Related U.S. Application Data

(60) Provisional application No. 61/778,230, filed on Mar. 12, 2013, provisional application No. 61/943,921, filed on Feb. 24, 2014.

(51) Int. Cl.
*A61F 9/007* (2006.01)
*A61F 9/00* (2006.01)
(Continued)

(52) U.S. Cl.
CPC ............ *A61F 9/007* (2013.01); *A61F 9/0017* (2013.01); *A61F 2/14* (2013.01); *A61F 2/141* (2013.01);
(Continued)

(58) Field of Classification Search
CPC ...... A61F 9/007; A61F 9/0008; A61F 9/0017; A61F 2/14; A61F 2/141; A61F 2/142;
(Continued)

(56) References Cited

U.S. PATENT DOCUMENTS 4,520,825 A 6/1985 Thompson et al.
4,539,988 A * 9/1985 Shirley ................ A61B 5/1411 606/182

(Continued)

FOREIGN PATENT DOCUMENTS

EP 1497483 A1 1/2005
EP 1651307 A2 5/2006

(Continued)

OTHER PUBLICATIONS

International Search Report and Written Opinion received for PCT Patent Application No. PCT/US2014/024496, mailed on Aug. 22, 2014, 12 pages.

(Continued)

*Primary Examiner* — Bhisma Mehta
*Assistant Examiner* — Nilay Shah

(57) ABSTRACT

Systems, devices, and methods for delivering an implant to the orbit. In some instances, the systems may include a delivery device having a tongue member and a handle. The delivery device may further include an ejector configured to deliver an implant from the tongue member. The delivery device may also include a piercing member configured to create an opening in tissue. The systems may further include a piercing member for creating an opening in tissue. In some instances, the piercing member may have a first blade member rotatably connected to a second blade member.

13 Claims, 26 Drawing Sheets

100
116
106
118
114
102
112
130
104

(51) Int. Cl.
*A61F 2/14* (2006.01)
*A61F 2/16* (2006.01)
*A61M 31/00* (2006.01)

(52) U.S. Cl.
CPC ............. *A61F 2/148* (2013.01); *A61F 2/1662* (2013.01); *A61M 31/007* (2013.01); *A61M 2210/0612* (2013.01)

(58) Field of Classification Search
CPC ........ A61F 2/145; A61F 2/148; A61F 2/1662; A61M 2210/0612; A61M 37/0069; A61M 5/322; A61M 5/3237; A61M 5/3271; A61M 5/3221; A61M 5/3234; A61M 31/007; A61B 5/1519; A61B 17/3468; A61B 17/3415; A61K 9/0048; A61K 9/0051; A61K 9/02; A61K 9/0024
See application file for complete search history.

(56) References Cited

U.S. PATENT DOCUMENTS 4,628,933 A 12/1986 Michelson
4,868,154 A 9/1989 Gilbard et al.
5,025,807 A 6/1991 Zabara
5,090,422 A 2/1992 Dahl et al.
5,099,829 A 3/1992 Wu
5,147,284 A 9/1992 Fedorov et al.
5,324,316 A 6/1994 Schulman et al.
5,345,948 A 9/1994 O'Donnell, Jr.
5,360,438 A 11/1994 Fisher
5,545,617 A 8/1996 Dartt et al.
5,607,461 A 3/1997 Lathrop
5,707,400 A 1/1998 Terry, Jr. et al.
5,843,140 A 12/1998 Strojnik
5,948,006 A 9/1999 Mann
6,001,088 A 12/1999 Roberts et al.
6,035,236 A 3/2000 Jarding et al.
6,050,999 A * 4/2000 Paraschac ............... A61F 2/148 219/636
6,051,017 A 4/2000 Loeb et al.
6,083,251 A 7/2000 Shindo
6,152,916 A 11/2000 Bige
6,205,359 B1 3/2001 Boveja
6,208,902 B1 3/2001 Boveja
6,240,316 B1 5/2001 Richmond et al.
6,246,911 B1 6/2001 Seligman
6,272,382 B1 8/2001 Faltys et al.
6,275,737 B1 8/2001 Mann
6,277,855 B1 8/2001 Yerxa
6,324,429 B1 11/2001 Shire et al.
6,327,504 B1 12/2001 Dolgin et al.
6,366,814 B1 4/2002 Boveja et al.
6,458,157 B1 10/2002 Suaning
6,505,077 B1 1/2003 Kast et al.
6,535,766 B1 3/2003 Thompson et al.
6,539,253 B2 3/2003 Thompson et al.
6,564,102 B1 5/2003 Boveja
6,658,301 B2 12/2003 Loeb et al.
6,662,052 B1 12/2003 Sarwal et al.
6,701,189 B2 3/2004 Fang et al.
6,792,314 B2 9/2004 Byers et al.
6,829,508 B2 12/2004 Schulman et al.
6,871,099 B1 3/2005 Whitehurst et al.
6,879,859 B1 4/2005 Boveja
6,885,888 B2 4/2005 Rezai
6,895,279 B2 5/2005 Loeb et al.
7,024,241 B1 4/2006 Bornzin et al.
7,054,692 B1 5/2006 Whitehurst et al.
7,067,307 B2 6/2006 Hochleitner et al.
7,069,084 B2 6/2006 Yee
7,142,909 B2 11/2006 Greenberg et al.
7,146,209 B2 12/2006 Gross et al.
7,169,163 B2 1/2007 Becker
7,190,998 B2 3/2007 Shalev et al.
7,225,032 B2 5/2007 Schmeling et al.
7,228,184 B2 6/2007 Heath
7,317,947 B2 1/2008 Wahlstrand et al.
7,330,762 B2 2/2008 Boveja et al.
7,346,398 B2 3/2008 Gross et al.
7,369,897 B2 5/2008 Boveja et al.
7,442,191 B2 10/2008 Hovda et al.
7,460,911 B2 12/2008 Cosendai et al.
7,477,947 B2 1/2009 Pines et al.
7,502,652 B2 3/2009 Gaunt et al.
7,547,447 B2 6/2009 Yiu et al.
7,565,204 B2 7/2009 Matei et al.
7,599,737 B2 10/2009 Yomtov et al.
7,636,597 B2 12/2009 Gross et al.
7,650,186 B2 1/2010 Hastings et al.
D613,408 S 4/2010 Gausmann et al.
D614,303 S 4/2010 Gausmann et al.
D614,774 S 4/2010 Gausmann et al.
7,725,176 B2 5/2010 Schuler et al.
7,725,195 B2 5/2010 Lima et al.
D617,443 S 6/2010 Grenon et al.
7,758,190 B2 7/2010 Korb et al.
7,778,703 B2 8/2010 Gross et al.
7,778,711 B2 8/2010 Ben-David et al.
7,792,591 B2 9/2010 Rooney et al.
7,805,200 B2 9/2010 Kast et al.
7,805,202 B2 9/2010 Kuzma et al.
7,805,203 B2 9/2010 Ben-David et al.
7,809,442 B2 10/2010 Bolea et al.
7,835,794 B2 11/2010 Greenberg et al.
7,846,124 B2 12/2010 Becker
7,860,570 B2 12/2010 Whitehurst et al.
7,879,079 B2 2/2011 Tu et al.
D638,128 S 5/2011 Prokop et al.
7,981,095 B2 7/2011 Grenon et al.
7,998,202 B2 8/2011 Lesh
8,019,419 B1 9/2011 Panescu et al.
8,019,441 B2 9/2011 Wallace et al.
8,145,322 B1 3/2012 Yao et al.
8,165,680 B2 4/2012 Greenberg et al.
8,204,591 B2 6/2012 Ben-David et al.
8,318,070 B2 11/2012 Shiah et al.
8,489,189 B2 7/2013 Tronnes
8,494,641 B2 7/2013 Boling et al.
8,918,181 B2 12/2014 Ackermann et al.
8,996,137 B2 3/2015 Ackermann et al.
9,079,042 B2 7/2015 Tiedtke et al.
9,095,723 B2 8/2015 Ackermann et al.
9,265,956 B2 2/2016 Ackermann et al.
2001/0020177 A1 9/2001 Gruzdowich et al.
2002/0013594 A1 1/2002 Dinger et al.
2002/0035358 A1 3/2002 Wang
2002/0188331 A1 12/2002 Fang et al.
2003/0045909 A1 3/2003 Gross et al.
2003/0114899 A1 6/2003 Woods et al.
2003/0120323 A1 6/2003 Meadows et al.
2003/0130809 A1 7/2003 Cohen et al.
2003/0192784 A1 10/2003 Zhou
2003/0233134 A1 12/2003 Greenberg et al.
2004/0050392 A1* 3/2004 Tu ....................... A61F 9/00781 128/898
2004/0059466 A1 3/2004 Block et al.
2004/0098067 A1 5/2004 Ohta et al.
2004/0147973 A1 7/2004 Hauser et al.
2005/0004621 A1 1/2005 Boveja et al.
2005/0010250 A1 1/2005 Schuler et al.
2005/0010266 A1 1/2005 Bogdanowicz
2005/0101967 A1* 5/2005 Weber ..................... A61F 2/167 606/107
2005/0105046 A1 5/2005 Tung
2005/0197675 A1 9/2005 David et al.
2005/0251061 A1 11/2005 Schuler et al.
2005/0267542 A1 12/2005 David et al.
2006/0004423 A1 1/2006 Boveja et al.
2006/0074450 A1 4/2006 Boveja et al.
2006/0095077 A1 5/2006 Tronnes et al.
2006/0095108 A1 5/2006 Chowdhury et al.
2006/0100668 A1 5/2006 Ben-David et al.
2006/0142822 A1 6/2006 Tulgar

(56) References Cited

U.S. PATENT DOCUMENTS

2006/0161225 A1 7/2006 Sormann et al.
2006/0195169 A1 8/2006 Gross et al.
2006/0206155 A1 9/2006 Ben-David et al.
2006/0235430 A1 10/2006 Le et al.
2006/0239482 A1 10/2006 Hatoum et al.
2006/0259098 A1 11/2006 Erickson
2006/0271108 A1 11/2006 Libbus et al.
2007/0038267 A1 2/2007 Shodo et al.
2007/0060815 A1 3/2007 Martin et al.
2007/0060954 A1 3/2007 Cameron et al.
2007/0150034 A1 6/2007 Rooney et al.
2007/0250119 A1 10/2007 Tyler et al.
2007/0250135 A1 10/2007 Bartz-Schmidt et al.
2007/0276314 A1 11/2007 Becker
2007/0299462 A1 12/2007 Becker
2008/0021515 A1 1/2008 Horsager et al.
2008/0082131 A1 4/2008 Llanos
2008/0109054 A1 5/2008 Hastings et al.
2008/0132933 A1 6/2008 Gerber
2008/0140141 A1 6/2008 Ben-David et al.
2008/0183242 A1 7/2008 Tano et al.
2008/0183243 A1 7/2008 Shodo
2009/0005835 A1 1/2009 Greenberg et al.
2009/0024187 A1 1/2009 Erickson et al.
2009/0024189 A1 1/2009 Lee et al.
2009/0099626 A1 4/2009 De Juan, Jr. et al.
2009/0101139 A1 4/2009 Karell
2009/0124965 A1 5/2009 Greenberg et al.
2009/0138061 A1 5/2009 Stephens et al.
2009/0157142 A1 6/2009 Cauller
2009/0157145 A1 6/2009 Cauller
2009/0157147 A1 6/2009 Cauller et al.
2009/0192571 A1 7/2009 Stett et al.
2009/0204142 A1 8/2009 Becker
2009/0241840 A1 10/2009 Mills
2009/0264966 A1 10/2009 Blum et al.
2009/0281594 A1 11/2009 King et al.
2009/0281596 A1 11/2009 King et al.
2009/0306738 A1 12/2009 Weiss et al.
2010/0030150 A1* 2/2010 Paques .................. A61F 9/0017 604/116
2010/0076423 A1 3/2010 Muller
2010/0087896 A1 4/2010 McCreery
2010/0094280 A1 4/2010 Muller
2010/0139002 A1 6/2010 Walker et al.
2010/0161004 A1 6/2010 Najafi et al.
2010/0168513 A1 7/2010 Pless et al.
2010/0179468 A1 7/2010 Becker
2010/0274313 A1 10/2010 Boling et al.
2010/0280509 A1 11/2010 Muller et al.
2010/0318159 A1 12/2010 Aghassian et al.
2011/0021975 A1 1/2011 Covello
2011/0028807 A1 2/2011 Abreu
2011/0028883 A1* 2/2011 Juan, Jr. ................ A61F 9/0017 604/8
2011/0093043 A1 4/2011 Torgerson et al.
2011/0152969 A1 6/2011 Zehnder et al.
2011/0202121 A1 8/2011 Wen
2011/0276107 A1 11/2011 Simon et al.
2011/0295336 A1 12/2011 Sharma et al.
2012/0130398 A1 5/2012 Ackermann et al.
2012/0197338 A1 8/2012 Su et al.
2012/0232615 A1 9/2012 Barolat et al.
2012/0253249 A1 10/2012 Wilson et al.
2012/0323227 A1 12/2012 Wolf et al.
2012/0330376 A1 12/2012 Flynn et al.
2013/0006095 A1 1/2013 Jenkins et al.
2013/0006326 A1 1/2013 Ackermann et al.
2013/0178937 A1 7/2013 Vassallo et al.
2013/0261706 A1 10/2013 Mirro et al.
2013/0304154 A1 11/2013 Goodman et al.
2014/0163580 A1 6/2014 Tischendorf et al.
2014/0214120 A1 7/2014 Simon et al.
2014/0257433 A1 9/2014 Ackermann et al.
2014/0277429 A1 9/2014 Kuzma et al.
2014/0316310 A1 10/2014 Ackermann et al.
2014/0316485 A1 10/2014 Ackermann et al.
2014/0371812 A1 12/2014 Ackermann et al.
2015/0088156 A1 3/2015 Ackermann et al.
2015/0335900 A1 11/2015 Ackermann et al.
2016/0022992 A1 1/2016 Franke et al.
2016/0114163 A1 4/2016 Franke et al.
2016/0114172 A1 4/2016 Loudin et al.
2016/0121118 A1 5/2016 Franke et al.

FOREIGN PATENT DOCUMENTS

EP 1919553 A1 5/2008
EP 1958661 A1 8/2008
EP 2205193 A2 7/2010
EP 2205314 A1 7/2010
JP 2002-325851 A 11/2002
JP 2002-539859 A 11/2002
JP 2005-52461 A 3/2005
JP 2006-515900 A 6/2006
JP 2007-44323 A 2/2007
JP 2007-528751 A 10/2007
JP 2008-183248 A 8/2008
JP 2008-541850 A 11/2008
JP 2010-505563 A 2/2010
JP 2010-051562 A 3/2010
JP 2010-537777 A 12/2010
JP 2011-030734 A 2/2011
WO WO-00/56393 A1 9/2000
WO 00/62672 A1 10/2000
WO 03/087433 A1 10/2003
WO 2004/026106 A2 4/2004
WO 2004/091453 A1 10/2004
WO WO-2004/112893 A2 12/2004
WO WO-2004/112893 A3 12/2004
WO 2005/007234 A2 1/2005
WO 2005/060984 A1 7/2005
WO 2006/127366 A1 11/2006
WO 2008/156501 A2 12/2008
WO 2009/035571 A2 3/2009
WO 2009/070709 A1 6/2009
WO WO-2010/003011 A1 1/2010
WO 2010/027743 A1 3/2010
WO 2011/011373 A1 1/2011
WO 2012/068247 A1 5/2012
WO 2012/139063 A2 10/2012
WO 2012/139063 A3 12/2012
WO WO-2014/138709 A1 9/2014
WO WO-2014/165124 A1 10/2014
WO WO-2014/172693 A2 10/2014
WO WO-2014/172693 A3 10/2014
WO WO-2015/130707 A2 9/2015
WO WO-2015/130707 A3 9/2015
WO WO-2016/015025 A1 1/2016
WO WO-2016/065211 A1 4/2016
WO WO-2016/065213 A1 4/2016
WO WO-2016/065215 A1 4/2016

OTHER PUBLICATIONS

Invitation to pay additional fees received for PCT Patent Application No. PCT/US2014/024496, mailed on Jun. 19, 2014. 2 pages.

Extended European Search Report (includes Supplementary European Search Report and Search Opinion) received for European Patent Application No. 11842076.9, mailed on Oct. 10, 2014, 5 pages.

Extended European Search Report received for European Patent Application No. 12768458.7, mailed on Aug. 28, 2014, 7 pages.

Non-Final Office Action received for U.S. Appl. No. 13/298,042, mailed on Oct. 2, 2013, 10 pages.

Notice of Allowance received for U.S. Appl. No. 13/298,042, mailed on Apr. 29, 2014, 5 pages.

Notice of Allowance received for U.S. Appl. No. 13/298,042, mailed on Aug. 11, 2014, 7 pages.

Notice of Allowance received for U.S. Appl. No. 13/298,042, mailed on Nov. 13, 2014, 5 pages.

(56) References Cited

OTHER PUBLICATIONS

Final Office Action received for U.S. Appl. No. 13/441,806, mailed on Mar. 12, 2015, 10 pages.
Non-Final Office Action received for U.S. Appl. No. 13/441,806, mailed on Sep. 17, 2015, 11 pages.
Non-Final Office Action received for U.S. Appl. No. 13/441,806, mailed on Dec. 18, 2013, 9 pages.
Notice of Allowance received for U.S. Appl. No. 14/561,107, mailed on Mar. 31, 2015, 7 pages.
Non-Final Office Action received for U.S. Appl. No. 14/816,846, mailed on Sep. 11, 2015, 5 pages.
Notice of Acceptance Received for Australian Patent Application No. 2011328900, mailed on Mar. 10, 2015, 4 pages.
Office Action received for Australian Patent Application No. 2011328900, mailed on Feb. 28, 2014, 3 pages.
Notice of Allowance received for Chinese Patent Application No. 201180064627.8, mailed on Jun. 30, 2015, 2 pages (1 page of English Translation and 1 page of Official Copy).
Office Action Received for Chinese Patent Application No. 201180064627.8, mailed on Feb. 2, 2015, 16 pages (7 pages of English Translation and 9 pages of Official Copy).
Office Action Received for Chinese Patent Application No. 201180064627.8, mailed on Jun. 20, 2014, 19 pages (6 pages of English Translation and 13 pages of Official Copy).
Notice of Acceptance received for Australian Patent Application No. 2012239966, mailed on Nov. 12, 2015, 3 pages.
Office Action Received for Australian Patent Application No. 2012239966, mailed on Mar. 17, 2014, 6 pages.
Office Action received for Chinese Patent Application No. 201280028006.9, mailed on Nov. 14, 2014, 14 pages (7 pages English Translation and 7 pages Official Copy).
Office Action received for Japanese Patent Application No. 2013-539971, mailed on Oct. 5, 2015, 11 pages (5 pages of English Translation and 6 pages of Official Copy).
Calogne, Margarita, "The Treatment of Dry Eye", Survey of Ophthalmology, vol. 45, No. 2, Mar. 2001, 13 pages.
Elsby et al., "Lacrimal Secretion in the Cat", Br. J. Pharmac. Chemother, vol. 29, No. 1, Jan. 1967, pp. 1-7.
Lora et al., "Lacrimal Nerve Stimulation by an Neurostimulator for Tear Production", Investigative Ophthalmology & Visual Science, vol. 50, Issue 13, Apr. 2009, 1 page.
International Preliminary Report on Patentability received for PCT Patent Application No. PCT/US2011/060989, mailed on May 30, 2013, 14 pages.
International Search Report & Written Opinion received for PCT Patent Application No. PCT/US2011/060989, mailed on Feb. 23, 2012, 16 pages.
International Search Report received for PCT Patent Application No. PCT/US2012/32629, mailed on Oct. 26, 2012, 4 pages.
Written Opinion received for PCT Patent Application No. PCT/US2012/032629, mailed on Oct. 26, 2012, 8 pages.
International Preliminary Report on Patentability received for PCT Application No. PCT/US2014/024496, mailed on Sep. 24, 2015, 9 pages.
Roessler et al., "Implantation and Explantation of a Wireless Epiretinal Retina Implant Device: Observations During the EPIRET3 Prospective Clinical Trial", Investigative Ophthalmology & Visual Science, vol. 50, No. 6, Jun. 2009, pp. 3003-3008.
Ruskell, Gordon L., "Distribution of Pterygopalatine Ganglion Efferents to the Lacrimal Gland in Man", Experimental Eye Research, vol. 78, No. 3, Mar. 2004, pp. 329-335.
Velikay-Parel et al., "Perceptual Threshold and Neuronal Excitability as Long-Term Safety Evaluation in Retinal Implants", Meeting Abstract at the Association for Research in Vision and Ophthalmology, Inc. Annual Meeting, Available at <http://www.abstractsonline.com/Plan/ViewAbstract.aspx?sKey=00d4c2e2-2814-48d9-b49338f4761ab4ca&cKey•9d81879a-9b1d-49c2-aff4-489d9-b493, vol. 52, Issue 14, Apr. 2011, 2 pages.
Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
Final Office Action received for U.S. Appl. No. 13/441,806, mailed on May 20, 2016, 10 pages.
Final Office Action received for U.S. Appl. No. 14/816,846, mailed on May 11, 2016, 12 pages.
Final Office Action mailed on Sep. 23, 2016, for U.S. Appl. No. 14/809,109, filed Jul. 24, 2015, 10 pages.
International Preliminary Report on Patentability received for PCT Application No. PCT/US2014/022158, mailed on Sep. 17, 2015, 7 pages.
International Search Report & Written Opinion received for PCT Patent Application No. PCT/US2014/022158, mailed on Jul. 30, 2014, 8 pages.
International Search Report and Written Opinion received for PCT Application No. PCT/US2015/042130, mailed on Oct. 28, 2015, 5 pages.
International Search Report and Written Opinion received for PCT Patent Application No. PCT/US2015/057023, mailed on Mar. 4, 2016, 10 pages.
International Search Report received for PCT Patent Application No. PCT/US2015/57021, mailed on Feb. 10, 2016, 4 pages.
International Search Report received for PCT Patent Application No. PCT/US2015/57019, mailed on Feb. 11, 2016, 4 pages.
Invitation to Pay Additional Fees received for PCT Application No. PCT/US2012/032629, mailed on Aug. 28, 2012, 2 pages.
Invitation to Pay Additional Fees received for PCT Patent Application No. PCT/US2015/057023, mailed on Jan. 7, 2016, 3 pages.
Invitation to Pay Additional Fees received for PCT Patent Application No. PCT/US2015/57021, mailed on Dec. 18, 2015.
Meng, I.D. et al. (2013). "The role of corneal afferent neurons in regulating tears under normal and dry eye conditions," Exp. Eye Res. 117:79-87.
Non-Final Office Action received for U.S. Appl. No. 14/201,753, mailed on Apr. 2, 2015, 6 pages.
Non-Final Office Action received for U.S. Appl. No. 14/809,109, mailed on Apr. 8, 2016, 8 pages.
Non-Final Office Action Received for U.S. Appl. No. 14/920,860, mailed Aug. 17, 2016.
Non-Final Office Action Received for U.S. Appl. No. 14/920,852, mailed on Aug. 1, 2016.
Non-Final Office Action mailed on Sep. 27, 2016, for U.S. Appl. No. 14/920,847, filed Oct. 22, 2015, 13 pages.
Notice of Allowance received for U.S. Appl. No. 14/201,753, mailed on Dec. 15, 2015, 2 pages.
Notice of Allowance received for U.S. Appl. No. 14/201,753, mailed on Oct. 15, 2015, 5 pages.
Restriction Requirement mailed on Jul. 2, 2013, for U.S. Appl. No. 13/298,042, filed Nov. 16, 2011, 7 pages.
Written Opinion received for PCT Patent Application No. PCT/US2015/57021, mailed on Feb. 10, 2016.
Written Opinion received for PCT Patent Application No. PCT/US2015/57019, mailed on Feb. 11, 2016, 6 pages.
Extended European Search Report mailed on Oct. 21, 2016, for EP Application No. 14 778 719.6, filed on Mar. 12, 2014, 8 pages.
Non-Final Office Action mailed on Nov. 2, 2016, for U.S. Appl. No. 13/441,806, filed Apr. 6, 2012, 11 pages.
Non-Final Office Action mailed on Dec. 6, 2016, for U.S. Appl. No. 14/816,846, filed Aug. 3, 2015, 13 pages.
Notice of Allowance mailed on Dec. 19, 2016, for U.S. Appl. No. 14/809,109, filed Jul. 24, 2015, 8 pages.

* cited by examiner 808
804
804
824
802
800
702
806
814
812
818
818
816
816
818
818
812
θ
814
800

824
802
702
806
814

702
812
820
808
816
810
804

708
904
900
902
906

1002

1000
1008
1006
1004
1010

714
812

706
716
702
704

706

814
800
1100
704

704

820
1100
902
702
900
708

704
1100

902
708
702

1100

902
708
702
706

1100

902
708
900
702
706

1200
1224
1218
1226
1220
1304
1230
1308
1232
1310
1228
1300
1206
1202
1210
1240
1242

1200
1242
1206
1226
1224
1218
1240
1204
1210
1202
1212

1200
1242
1218
1240
1204
1202
1244

1224
1230
1202
1218
1244
1212
1242

1204
1224
1230
1308
1300
1228
1304
1238
1206
1304
1310
1240
1214
1202
1242

1224
1218
1308
1310

1306
1300
1304
1304
1208
1202
1232
1210

1218
1308

1300
1304
1304
1208
1202
1232
1210

IMPLANT DELIVERY DEVICES, SYSTEMS, AND METHODS

CROSS-REFERENCE TO RELATED APPLICATIONS

This application claims priority to U.S. Provisional Patent Application Ser. No. 61/778,230, filed Mar. 12, 2013 and titled "IMPLANT DELIVERY DEVICES, SYSTEMS, AND METHODS" and to U.S. Provisional Patent Application Ser. No. 61/943,921, filed Feb. 24, 2014 and titled "IMPLANT DELIVERY DEVICES, SYSTEMS, AND METHODS," the contents of each of which are hereby incorporated in its entirety.

FIELD

The present invention relates generally to systems, devices, and methods for delivering an implant to a portion of the anatomy such as the orbit.

BACKGROUND

Treatment methods for ocular conditions such as dry eye may require delivery of an implant or other device to the orbit of a patient. The orbit is a cavity of the skull that houses the eyeball and its nerves, muscles, and other appendages. The presence of these anatomical structures within the orbit, which in some instances may be easily damaged, can provide a limited working space for delivery of implants. Accordingly, it may be desirable to provide one or more devices which may facilitate delivery of one or more implants to the orbit.

BRIEF SUMMARY

Described here are systems, devices, and methods for delivering an implant to the orbit. In some variations, the devices described here may comprise a handle and a tongue member extending from a distal portion of the handle. In some variations, the devices may further comprise an ejector. In some of these variations, the ejector may comprise a control slider slidably attached to the handle, a pusher slidably attached to the tongue member, and a linkage connecting the control slider and the pusher. In these variations, advancement of the control slider relative to the handle may advance the pusher relative to the tongue member, and withdrawal of the control slider relative to the handle may withdraw the pusher relative to the tongue member. In some of these variations, the tongue member may be curved, and in some variations may comprise a tapered tip. Additionally or alternatively, the tongue member may comprise one or more depth stops positioned along a length of the tongue member. In some of these variations, the one or more depth stops comprises one or more projections or protrusions. In others of these variations, the one or more depth stops comprises one or more notches. In still other variations, the one or more depth stops comprises one or more markers.

In some variations, the devices described here may comprise a piercing member having a piercing tip. In some variations, the piercing member may be moveable between a piercing configuration in which the piercing tip extends beyond a tip of the tongue member and a retracted configuration in which the piercing tip does not extend beyond a tip of the tongue member. In some variations, the piercing member may be biased toward the retracted configuration.

Additionally or alternatively, in variations of the devices described here comprising a control slider, the control slider may be configured to move the piercing member from the retracted configuration to the piercing configuration. In some of these variations, control slider may be configured to move the piercing member from the retracted configuration to the piercing configuration during withdrawal of the control slider.

In some variations, the devices described here may further comprise a rocker, wherein the rocker is rotatably connected to the handle, wherein the device is configured such that rotation of the rocker in a first direction to a first position moves the piercing member to the piercing configuration, and wherein rotation of the rocker in a second direction opposite the first direction to a second position moves the piercing member to the retracted configuration. In some of these variations, the rocker may be biased toward the second position. In variations where the device comprises a control slider, the control slider may be configured to rotate the rocker in the first direction. In some of these variations, the control slider may comprise a button, wherein depression of the button rotates the rocker in the first direction. In some of these variations, the control slider may be slidable along the handle between a retracted position and an advanced position, and the handle may configured to allow depression of the button when the control slider is in the retracted position and to prevent depression of the button when the control slider is in the advanced position.

In some variations of the systems described here, the system may comprise an implant, and a delivery device comprising a handle, a tongue member extending from the handle, and an ejector. In these variations, the implant may be releasably and slidably connected to the tongue member, and the ejector may advance the implant relative to the tongue member to release the implant from the tongue member. In some of these variations, the system further comprises a piercing device, wherein the piercing device comprises a first blade member pivotally attached to a second blade member. In other variations, the delivery device may further comprises a piercing member moveable between a piercing configuration in which the piercing tip extends beyond a tip of the tongue member and a retracted configuration in which the piercing tip does not extend beyond a tip of the tongue member.

In other variations of the devices described here, the devices may comprise a first blade member and a second blade member pivotally connected to the first blade member, each comprising a tip, an inner edge, an outer edge, and a notch positioned along the outer edge. The device may further comprise a first grip connected to the first blade member and a second grip connected to the second blade member. Rotation of the first and second grip may rotate the first and second blade members between a first configuration in which the tip of the first blade member coincides with the tip of the second blade member to form a point, and a second configuration in which the tip of the first blade member is spaced apart from the tip of the second blade. In some of these variations, a distance between the notch of the first blade member and the notch of the second blade member in the first configuration is less than a distance between the notch of the first blade member and the notch of the second blade member in the second configuration. In some variations, the device may further comprise a spring member biasing the first grip away from the second grip. Additionally or alternatively, the device may further comprise a range-limiting element configured to limit the amount that the first grip may rotate away from the second grip. Additionally or alternatively, the device may further comprise a range-limiting element configured to limit the amount that the first grip may rotate toward the second grip.

Also described here are methods for delivering an implant into an orbit. In some variations, the methods may comprise piercing the conjunctiva to form an opening therein, advancing a tongue member of a delivery device through the opening to form a pocket between tissues beyond the opening, and delivering an implant from the tongue member into the pocket. In some variations, the method may further comprise dilating the opening. In some of these variations, piercing the conjunctiva and dilating the opening may comprise piercing the conjunctiva and dilating the opening with a piercing device. In others of these variations, piercing the conjunctiva and dilating the opening may comprise piercing the conjunctiva and dilating the opening with the delivery device. In some of these variations, the delivery device may comprise a piercing member moveable between a piercing configuration in which a piercing tip of the piercing member extends beyond a tip of the tongue member and a retracted configuration in which the piercing tip does not extend beyond a tip of the tongue member. In some of these variations, piercing the conjunctiva may comprise piercing the conjunctiva with the piercing tip of the piercing member. Additionally or alternatively, advancing the tongue member may comprise advancing the tongue member with the piercing member in the retracted configuration.

In other variations of the systems described here, the system may comprise a delivery device. The delivery device may comprise a cannula defining a channel extending between an inlet and an outlet, the cannula comprising a blade. The delivery device may further comprise a tongue slidably connected to the cannula and positioned to extend at least partially through the channel, and a plunger slidably connected to the cannula and positioned to extend at least partially through the channel. The cannula may comprise a top wall, wherein the top wall comprises a slot extending at least partially along the channel. In some of these variations, the plunger may be positioned between the tongue and the top wall. In some variations, the plunger comprises a plunger portion, a stopper portion, and a transition region connecting the stopper portion and the plunger portion. The plunger may be positioned such that the plunger portion of the plunger is positioned at least partially inside the channel, the stopper portion is positioned outside of the channel, and the transition region extends through the slot of the top wall. In some of these variations, a distal end of the stopper portion may extend distally of a distal end of the transition region to define a space between a distal portion of the stopper portion and the plunger portion. In some of these variations, the cannula may comprise a stop bar having an aperture therethrough, and the distal portion of the stopper portion may be sized to fit through the aperture of the stop bar. In some variations, the stop bar is perpendicular to a longitudinal axis of the cannula. In other variations, the stop bar may be positioned an angle clockwise of the longitudinal axis, wherein the angle is less than 90 degrees. In still other variations, the stop bar may be positioned an angle clockwise of the longitudinal axis, wherein the angle is greater than 90 degrees. In some variations where a top wall of the cannula comprises a slot, the slot may comprise a proximal segment, a distal segment, and an intermediate segment positioned between the proximal segment and the distal segment. In some of these variations, the intermediate segment may have a width greater than or equal to a width of the implant, and the distal segment may have a width less than the width of the implant.

In some variations, the tongue may be moveable between a retracted position in which a distal end of the tongue is positioned in the channel and an advanced position in which a distal end of the tongue is positioned distally of the outlet of the channel. In some of these variations, the tongue may comprise a handle, wherein the handle is sized to be prevented from entering the inlet, and wherein the handle of the tongue contacts the inlet when the tongue is in the advanced position. In some of these variations, the distal end of the tongue is positioned distal to a distal end of the blade when the tongue is in the advanced position. Additionally or alternatively, the plunger may comprise a handle, and the plunger and tongue may be positioned such that the handle of the tongue is prevented from being withdrawn proximally of the handle of the plunger.

In some variations, the plunger may be moveable between a retracted position in which a distal end of the plunger is positioned in the channel and an advanced position in which a distal end of the plunger is positioned distally of the outlet of the channel. In some of these variations, the delivery device further comprises an intermediate stop positioned to temporarily prevent advancement from the retracted position to the advanced position. In some of these variations, the intermediate stop may comprise a bumper plate moveable between a lowered position and a raised position, wherein the bumper plate prevents advancement of the plunger to the advanced position when the bumper plate is in the lowered position and wherein the bumper plate does not prevent advancement of the plunger to the advanced position when the bumper plate is in the raised position. In some of these variations, the delivery device comprises on or more springs connecting the bumper plate to the cannula. In some of these variations, the one or more springs bias the bumper plate toward the raised position. Additionally or alternatively, the bumper plate may comprise an extension positioned to extend into the channel through the slot of the top wall when the bumper plate is in the lowered position. In some variations, the delivery device may further comprise a release bracket, wherein the release bracket is positioned to releasably hold the bumper plate in the lowered position. In some variations, the system may comprise a biasing member connected to the cannula, wherein the biasing member has a first end connected to a bottom wall of the channel and a free end biased toward a top wall of the channel. In some variations, the system may further comprise an implant.

In some variations, the methods described here may comprise piercing tissue with a blade of a cannula of a delivery device to form a tissue opening, advancing a tongue through a channel of the cannula to advance a distal end of the tongue out of an outlet of the channel and through the tissue opening, and advancing a plunger through the channel of the cannula to advance the implant out of the outlet of the channel and through the tissue opening to deliver the implant to a pocket formed between tissue beyond the tissue opening. In some of these variations, the cannula may comprise a top wall, wherein the top wall comprises a slot extending at least partially along the channel. In some of these variations, advancing the plunger may comprise advancing the plunger between the tongue and the top wall. In some of these variations, the plunger may comprise a plunger portion, a stopper portion, and a transition region connecting the stopper portion and the plunger portion, and advancing the plunger may comprise advancing the plunger with the plunger portion of the plunger is positioned at least partially inside the channel, the stopper portion positioned outside of the channel, and the transition region extending through the slot of the top wall. In some of these variations, a distal end of the stopper portion may extend distally of a distal end of the transition region to define a space between a distal portion of the stopper portion and the plunger portion. In these variations, advancing the plunger may comprise advancing the plunger such that a distal end of the stopper portion as advanced distally of a distal end of the slot of the top wall. In some of these variations the cannula comprises a stop bar having an aperture therethrough, and advancing the plunger comprises advancing the distal portion of the stopper portion through the aperture of the stop bar.

In some variations where a top wall of a cannula comprises a slot, the slot comprises a proximal segment, a distal segment, and an intermediate segment positioned between the proximal segment and the distal segment. In some of these variations, the intermediate segment has a width greater than or equal to a width of the implant, and the method further comprises inserting the implant into the channel through the intermediate segment. In some variations, advancing the tongue comprises advancing the tongue from a retracted position in which the distal end of the tongue is positioned in the channel. In some of these variations, the tongue comprises a handle, wherein the handle is sized to be prevented from entering the inlet, and advancing the tongue comprises advancing the tongue until the handle of the tongue contacts the inlet. In some of these variations, the distal end of the tongue is positioned distal to a distal end of the blade when the handle of the tongue contacts the inlet. In some of these variations, the plunger comprises a handle, and the plunger and tongue are positioned such that the handle of the tongue is prevented from being withdrawn proximally of the handle of the plunger.

In some variations, advancing the plunger comprises advancing the plunger from a retracted position in which the distal end of the tongue is positioned in the channel. In some of these variations, the method may further comprise advancing the plunger to an intermediate position, wherein an intermediate stop is positioned to temporarily prevent further advancement of the plunger. In some of these variations, the intermediate stop comprises a bumper plate moveable, and the method further comprises raising the bumper plate from a lowered position to a raised position to allow further advancement of the plunger. In some of these variations, the delivery device comprises on or more springs connecting the bumper plate to the cannula. The one or more springs may bias the bumper plate toward the raised position. Additionally or alternatively, the bumper plate comprises an extension positioned to extend into the channel through the slot of the top wall when the bumper plate is in the lowered position. Additionally or alternatively, the delivery device further comprises a release bracket. The release bracket may be positioned to releasably hold the bumper plate in the lowered position, and raising the bumper plate from a lowered position to a raised position may comprise deflecting the release bracket.

DETAILED DESCRIPTION

Figure 1A:
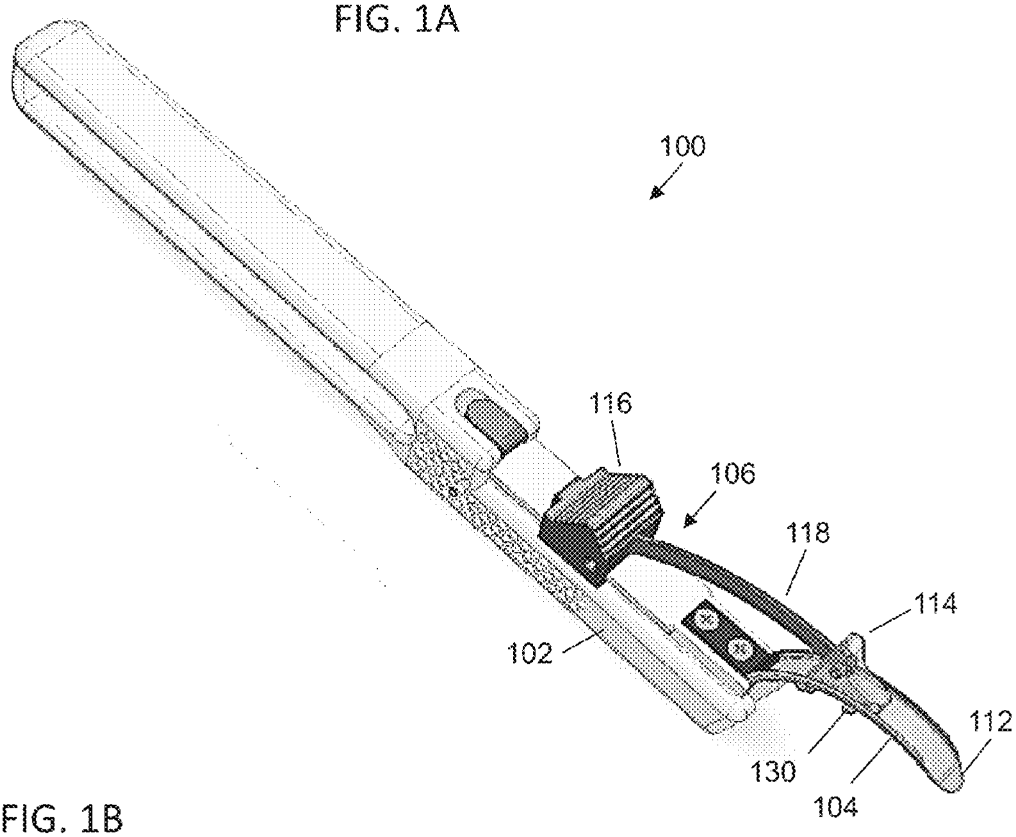
FIG. 1A depicts a perspective view of an illustrative variation of one of the delivery devices described here.

Described here are systems, devices, and methods for delivery of an implant into the orbit. Generally, the systems and devices may be configured to deliver one or more implants into tissue within the orbit (e.g., between the eyeball and the bones forming the orbit). Generally, the systems and devices described here may be used to form an opening in a tissue, such as the conjunctiva, to separate tissue beyond the opening to form a pocket in the tissue, and to deliver an implant into the pocket. The systems described here may include one or more devices configured to perform these steps. In some instances, the systems include a single device that performs all of the steps. In other instances, the system may include multiple devices which collectively perform these steps. The devices described here may be sterilizable (and in some instances, resterilizable), and may or may not be disposable (or partially disposable). Examples of these devices, systems, and methods will be described in more detail below.

The systems, devices, and methods described here may be used to deliver any suitable implant or implants. In some variations, the implant may include a stimulation device or one or more components thereof. The stimulation device may be configured to provide stimulation therapy to one or more target tissues. In some instances, the stimulation device may be configured to excite or activate an anatomic structure (e.g., the lacrimal gland). Additionally or alternatively, the stimulation device may be configured to inhibit activity of anatomic structure (e.g., one or more paintransmitting nerves). The systems, devices, and methods may be configured to deliver the entire stimulation device, or may be configured to deliver one or more components thereof (e.g., one or more electrode-bearing leads). In some variations, the stimulation device may be any device such as described in U.S. patent application Ser. No. 13/441,806, titled "STIMULATION DEVICES AND METHODS" and filed on Apr. 6, 2012, which is hereby incorporated by reference in its entirety.

Additionally or alternatively, the implant may include one or more drug-releasing devices or substances. In variations where the implant includes a stimulation device, the stimulation device may be configured to elute or otherwise release one or more drugs. In other variations, the implant may include an implantable pump which is configured to dispense one or more drug-containing substances. In yet other variations, the implant may include one or more drug-releasing depots (e.g., a solid or gel-like depot, which may or may not be formed from a polymer) and/or one or more drug-releasing liquids or gases. Additionally or alternatively the implant may comprise an orthopedic support (e.g., a wedge, shim, or the like) which is configured to provide structural support to surrounding tissue. In still other variations, the implant may comprise one or more mesh implants, retinal detachment treatment methods, or the like.

When the systems, devices, and methods described here are used to deliver an implant or implants to the orbit, the implants or implants may be delivered to any suitable portion of the orbit, such as, for example, the upper orbit, the lower orbit, the nasal orbit, the temporal orbit, the anterior orbit, and/or the posterior orbit. In some variations, the systems and devices described here may be used to deliver an implant to the lacrimal fossa. In some of these variations, the implant may be delivered in, on, or near the lacrimal gland. For example, in some instances the systems and methods described here may be used to position and deliver an implant in the lacrimal fossa between the lacrimal gland and the fontal bone of the orbit.

Figure 5A:
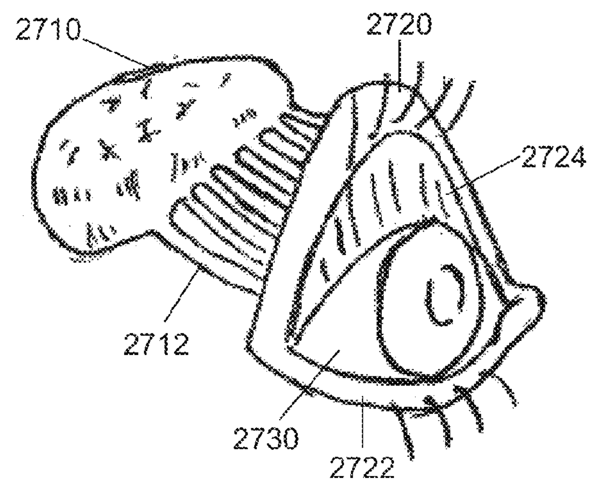
FIG. 5A depicts a perspective view of a lacrimal apparatus.
Figure 5B:
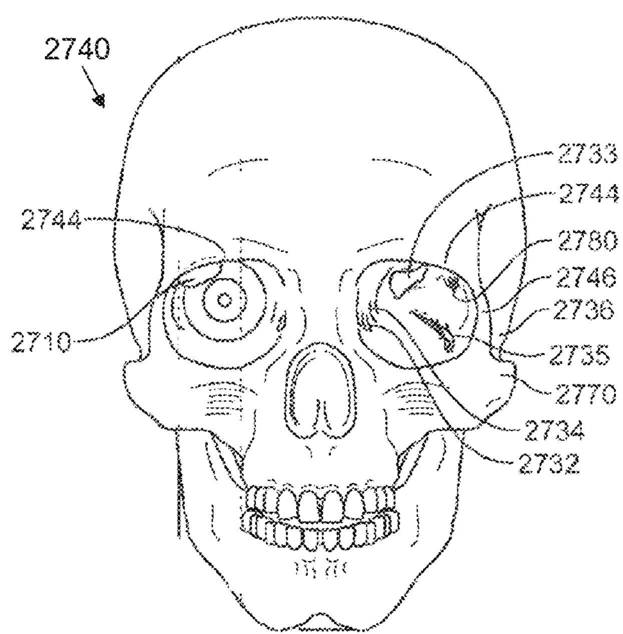
FIGS. 5B and 5C depict front views of the anatomy of the skull.
Figure 5C:
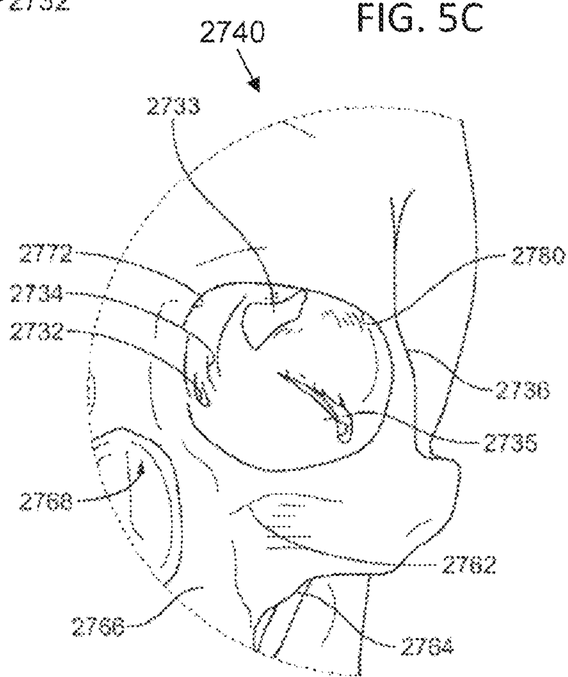

For the purposes of illustration, FIGS. 5A-5C depict various views of the anatomy of the head of a patient. FIG. 5A illustrates the lacrimal (or lachrymal) apparatus, the physiological system that contains the structures of the orbit for tear production and drainage. Shown there is an eye (2730) having an upper lid (2720) and a lower lid (2722). The upper lid (2722) is shown in FIG. 5A as being raised to reveal the conjunctiva (2724), which may line the inside of the eyelids and cover the sclera of the eye (2730). The lacrimal apparatus may include a lacrimal gland (2710) and ducts (2712). The lacrimal gland (2710) may secrete lacrimal fluid (i.e., tears) which may flow through the ducts (2712) into the space between the eye (2730) and the upper (2720) and lower (2722) lids. The lacrimal gland (2710) may be innervated by several nerves. These nerves may include the rami lacrimales, the lacrimal nerve, perivascular nerves of lacrimal artery, and sympathetic nerves fibers and neurites which innervate the lacrimal gland and its associated vasculature. When the eye (2730) blinks, the lacrimal fluid may be spread across the surface of the eye (2730). The lacrimal fluid (2714) may collect in the lacrimal lake (not shown), and may be drawn into the puncta (not shown) by capillary action. The lacrimal fluid may flow through lacrimal canaliculi (not shown) at the inner corner of the upper (2720) and lower (2722) lids to enter lacrimal ducts (not shown) and drain through to the nasolacrimal duct (not shown). The lacrimal fluid may drain from the nasolacrimal duct into the nasal cavity of the patient.

FIG. 5B shows a front view of the skull, and emphasizes the anatomy of the orbit with respect to the bones of the skull (2740). FIG. 5C shows an enlarged view of the left orbit of the skull (2740). As shown there, the exterior to the orbit includes the posterior lacrimal crest (2734), the supraorbital process (2744), the frontal process (2746), the sphenoid bone (2736), and the zygomatic bone (2770). The interior of the left orbit includes the superior orbital fissure (2733), inferior orbital fissure (2735), the fossa for the lacrimal gland (2780) and the fossa for the lacrimal sac (2732). The structures that enter the orbit through the superior orbital fissure may include the cranial nerves (CN) III, IV, and VI, lacrimal nerve, frontal nerve, nasociliary nerve, orbital branch of middle meningeal artery, recurrent branch of lacrimal artery, superior orbital vein, and the superior ophthalmic vein. The structures that enter the orbit through the inferior orbital fissure may include the infraorbital nerve, zygomatic nerve, parasympathetics to the lacrimal gland, infraorbital artery, infraorbital vein, and inferior ophthalmic vein branch to pterygoid plexus. Some of the bony structures and regions shown in FIG. 5C include, but are not limited to, the infraorbital foramen (2762), the maxillary axis (2764), the nasal-maxillary area (2766), the nasal cavity (2768), and the inferior medial aspect of the supraorbital process (2772).

Generally, the methods described here comprise piercing a first tissue to form an opening therein, forming a pocket in tissue beyond the opening, delivering an implant into that pocket, and, in some variations, closing the opening in the first tissue. In some variations, the methods further comprise dilating the opening formed in the first tissue. For example, in some variations, the methods comprise piercing the conjunctiva to form an opening therein, separating tissue beyond the conjunctiva to form a pocket in the tissue, and delivering an implant into the pocket. In some of these variations, the pocket is formed between the lacrimal gland and the frontal process of the orbit. In some variations, the methods further comprise closing the opening in the conjunctiva.

When the methods described here comprise piercing the conjunctiva to form an opening therein, it may be necessary to either move or pierce the eyelid covering the conjunctiva. Accordingly, in some variations, the method may comprise retracting an eyelid. In these variations, the eyelid may be held in a retracted position (e.g., using one or more tools, a finger, or the like). In other variations, the methods may comprise piercing both the eyelid and the conjunctiva. In variations that include piercing the eyelid, the method may further comprise tensioning the eyelid, which may facilitate piercing of the eyelid. Additionally or alternatively, the method may further comprise raising a user's brow to pull a portion of the eyelid into the eyelid crease under the frontal process.

When piercing the conjunctiva, it may be desirable to create tension in the conjunctiva before and/or during piercing of the conjunctiva. For example, the patient may be directed to look away from the intended piercing location, which may act to tension the conjunctiva. Additionally or alternatively, retracting the eyelid may act to at least partially tension the conjunctiva (and may also move structures such as the cornea away from the insertion point). In some variations, once the conjunctiva has been pierced to form an opening therein, the opening in the conjunctiva may be dilated, such as will be described in more detail below. Dilating of the opening in the conjunctiva may facilitate introduction of a portion of delivery device through the opening.

Following formation (and dilation, when the methods include a dilation step) of the opening, a portion of a delivery device may be advanced through the opening in the conjunctiva to form a pocket between tissue beyond the conjunctiva. For example, in some variations, this may include forming a pocket between the lacrimal gland and the frontal process of the orbit. In some of these variations, this may further include forming a pocket between the periosteum and the lacrimal gland. In others of these variations, this may further include forming a pocket between the periosteum and the bone of the orbit. In other variations, this may include forming a pocket between the lacrimal gland and the tarsus of the eyelids. The pocket is preferably formed using a blunt portion of the device, which may reduce the likelihood of inadvertently damaging tissue such as the eye or the lacrimal gland.

An implant (or plurality of implants) may be delivered into the pocket formed between tissues beyond the conjunctiva. In some instances, the implant may be delivered simultaneously with the formation of the pocket. In other variations, the implant may be delivered after formation of the pocket. In some instances, the methods may also comprise removing any delivery devices that have been advanced into the conjunctiva or the tissues beyond the conjunctiva. Removal of the one or more delivery devices may occur simultaneously with delivery of the implant, or may occur after the implant has been delivered. Following removal of the one or more delivery devices, the opening in the conjunctiva may be closed. The opening may be closed in any suitable manner. In some variations, the opening may be closed using one or more sutures, one or more adhesives, electrocautery techniques, one or more staples, combinations thereof, and the like. In some instances, the methods may not comprise a separate closing step, as the opening of the conjunctiva may naturally contract sufficiently to at least partially close the opening.

The methods described here may be performed by a system including one or more delivery devices. In some variations, the system may include a single device which may be used to pierce the conjunctiva to form an opening (and to dilate the opening in variations that comprise a dilating step), create the pocket between tissue beyond the conjunctiva, and deliver the implant. In other variations, a first device may be used to pierce the conjunctiva to form an opening (and to dilate the opening in variations that comprise a dilating step), while a second device may be inserted into the opening to form the pocket between tissues beyond the conjunctiva. The second device may be further used to deliver the implant. In yet other variations, a first device may be used to pierce the conjunctiva to form an opening in the conjunctiva (and to dilate the opening in variations that comprise a dilating step), a second device may be inserted into the opening to form the pocket between tissues beyond the conjunctiva, and a third device may be advanced into the pocket to deliver the implant. Any suitable delivery devices as described here may be used to perform one or more of these steps, and several illustrative devices will be described in more detail below.

Figure 1B:
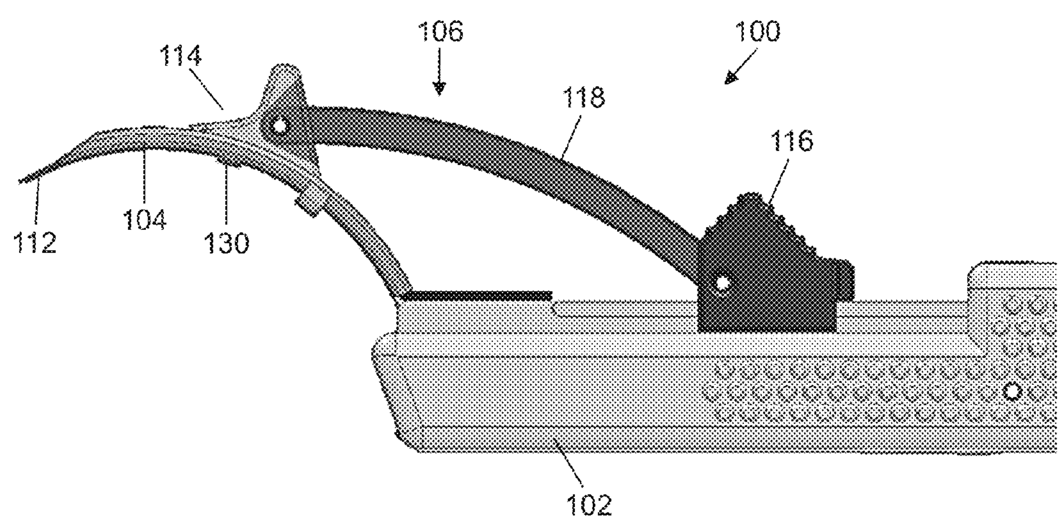
FIG. 1B shows a side view of a distal portion of the delivery device of FIG. 1A.
Figure 1C:
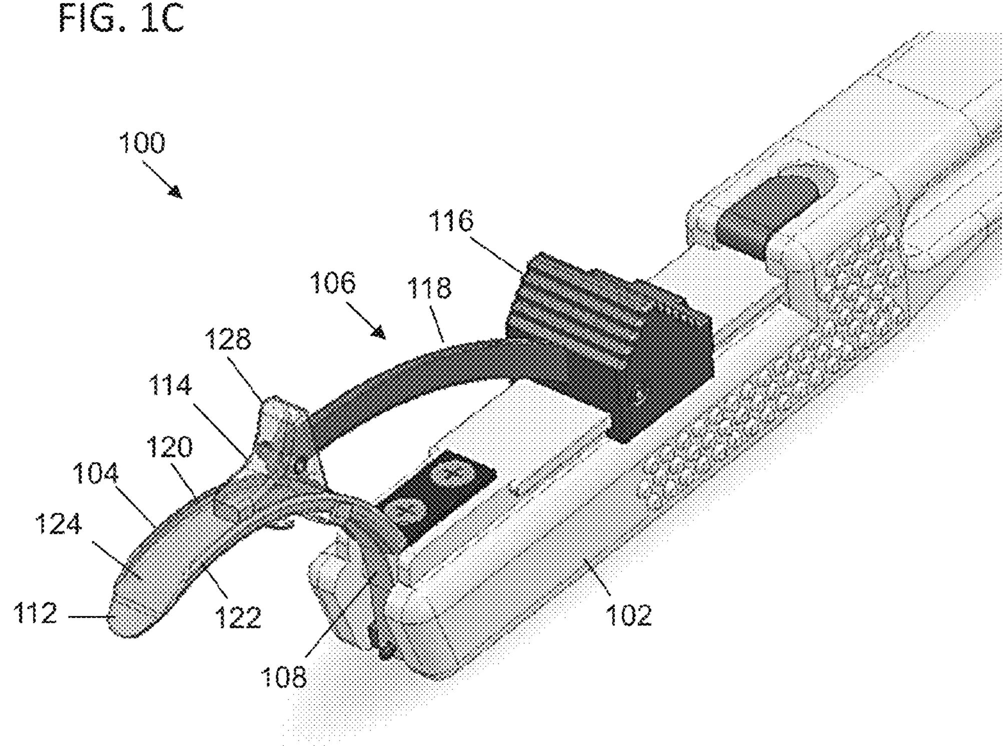
FIGS. 1C-1E show perspective views of a distal portion of the delivery device of FIG. 1A.
Figure 1D:
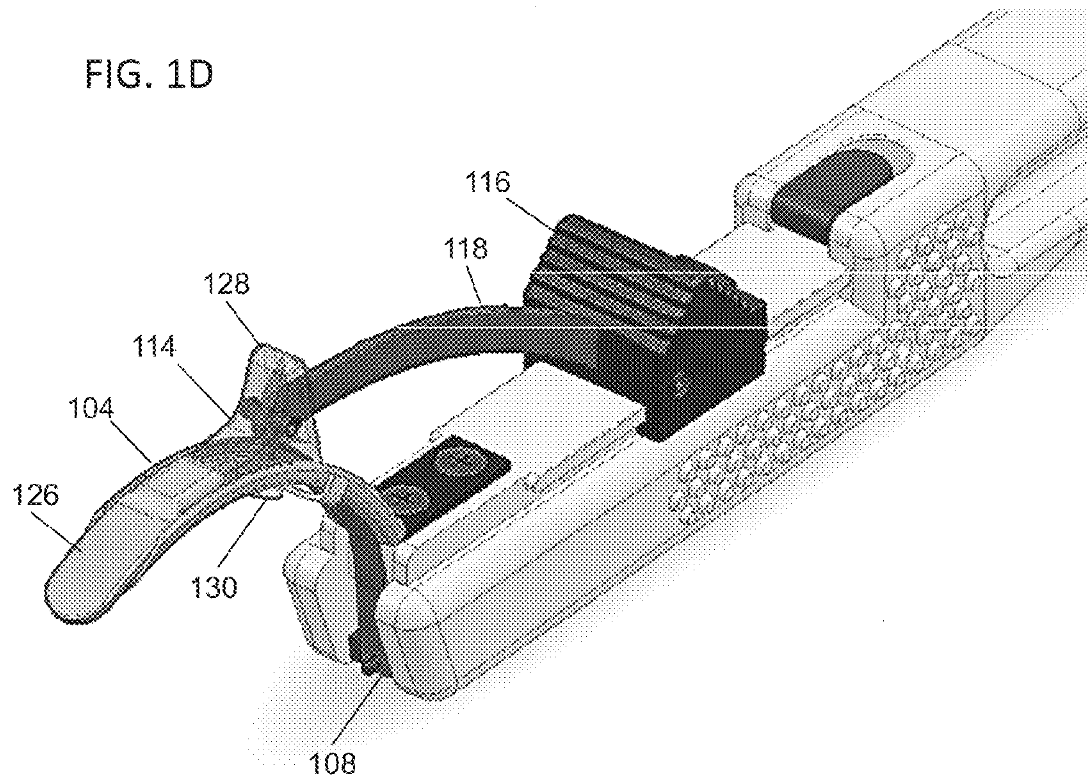

For example, FIGS. 1A-1H depict one variation of the delivery devices described here. FIG. 1A depicts a perspective view of the delivery device (100), and FIGS. 1B and 1C show a side view and a perspective view, respectively, of a distal portion of the delivery device (100). As shown there, the delivery device (100) may comprise a handle (102) and a tongue member (104) extending from a distal portion the handle (102). In some variations, the delivery device (100) may further comprise an ejector (106), but need not. In variations where the delivery device (100) comprises an ejector (106), the ejector (106) may be configured to deliver an implant from the delivery device (100). Additionally or alternatively, the delivery device (100) may comprise a piercing member (108), but need not. In variations where the delivery device (100) comprises a piercing member (108), the piercing member (108) may have a piercing tip (132) configured to pierce tissue such as the conjunctiva to form an opening therein. In some variation, the delivery device (100) may comprise both an ejector (106) and a piercing member (108). In other variations, the delivery device (100) may comprise an ejector (106), but not a piercing member (108). In these variations, a separate device may be used to form an opening in tissue, as will be described in more detail below, and the tongue member (104) of the delivery device (100) may be advanced through the opening. In still other variations the delivery device (100) may comprise a piercing member (108), but not an ejector (106). In these variations, a separate device may be used to deliver an implant. Each of the components of the delivery device (100) will be described in more detail below.

Generally, the handle (102) is sized and configured to be held by a user, which may allow the user to manipulate and control the delivery device (100). The handle (102) may have any suitable length (e.g., between about 5 cm and about 20 cm, between about 10 and about 15 cm, or the like) and diameter (e.g., between about 0.5 cm and about 4 cm, between about 1 cm and 3 cm, or the like). While shown in FIG. 1A as having a generally squared cross-sectional shape, the handle (102) may have a cross-section having any suitable shape (e.g., circular, oval, rectangular, another polygon, an irregular shape, or the like). Additionally, in some variations the handle (102) may comprise one or more finger grooves (not shown), but need not. Finger grooves may create a grip-like arrangement that allow a user to more easily grasp and hold the delivery device (100). Generally, the handle (102) allows the device to be gripped and manipulated with one hand, such that the device may be operated with a single hand. The various components of the delivery device (100) (e.g., the handle (102), the tongue member (104)) may be formed from any suitable material or materials, such as one or more metals (e.g., stainless steel, titanium, titanium alloys, or the like), one or more biocompatible plastics (e.g., polycarbonate, ABS, or the like), combinations thereof and the like.

The tongue member (104) may extend from the handle (102) (e.g., a distal portion of the handle as shown in FIG. 1A). Generally, the tongue member (104) is configured to pass between tissues to form a pocket therebetween. In some variations the tongue member (104) may be curved (such as shown in FIG. 1A), but it should be appreciated that in other variations the tongue member (104) may be straight. When the tongue member (104) is curved, it may have any suitable radius of curvature. In some variations, a curved tongue member (104) may have a radius of curvature that corresponds to a radius of curvature of the orbit. In other variations, it may be desirable to have a curved tongue member (104) having a radius of curvature greater than the radius of curvature of the orbit. In these variations, a tip (112) of the tongue member (104) may be used to palpate the orbit or other tissue structures during advancement of the tongue member (104) past the conjunctiva. The radius of curvature of the orbit may be between about 10 mm and about 50 mm, depending at least in part on the patient and the specific portion of the orbit. In some variations, the curved tongue member (104) may have a radius of curvature greater than about 10 mm, between about 10 mm and about 50 mm, between about 20 and 40 mm, about 25 mm, or the like. In some instances, a delivery device (100) may be selected from a plurality of delivery devices (100) having curved tongue members (104) with different radii of curvatures, depending on the patient. In variations where the delivery device (100) comprises a straight tongue member (104), the tongue member (104) may be used to palpate the orbit or other tissue structures during advancement of the tongue member (104).

In some variations, the tongue member (104) may be configured to dilate an opening formed in tissue, such as the conjunctiva. For example, in the variation of the delivery device (100) shown in FIG. 1A, the width of the tip (112) of the tongue member (104) may be tapered such that the width decreases from a proximal end of the tip to the distal end of the tip. When the tip (112) is advanced through an opening in tissue (such as the conjunctiva), the increasing width of the tip (112) may dilate the opening as the tip passes therethrough. In some variations, the height of the tongue member (104) may also be tapered to further assist in dilation of an opening and/or forming the pocket between tissues. It should be appreciated that in some variations, the tip (112) of the tongue member (104) may not be tapered. Additionally, in some variations it may be preferable to configure the tongue member (104) such that the tip (112) is rounded or otherwise blunt. In these variations, the tongue member (104) may still be able to push or otherwise displace tissue to create a pocket between tissues, but may have a reduced likelihood of cutting or otherwise damaging certain tissue (such as the eyeball) during advancement of the tongue member (104).

Generally, it may be desirable to allow a user to control the amount that the tip (112) of the tongue member (104) is advanced beyond the tissue opening. For example, in instances where the delivery devices described here are used to position an implant between the lacrimal gland and the frontal process of the orbit, it may be desirable to first position the tip (112) of the tongue member (104) between the lacrimal gland and the frontal process of the orbit. If the tongue member (104) is not advanced far enough, the implant may not reach the target location on the lacrimal gland. Conversely, if the tongue member is advanced too far, the implant may be placed beyond the lacrimal gland. Accordingly, in some variations the tongue members (104) described here may comprise one or more features to assist a user in controlling the advancement of the tongue member (104) through tissue.

Figure 1E:
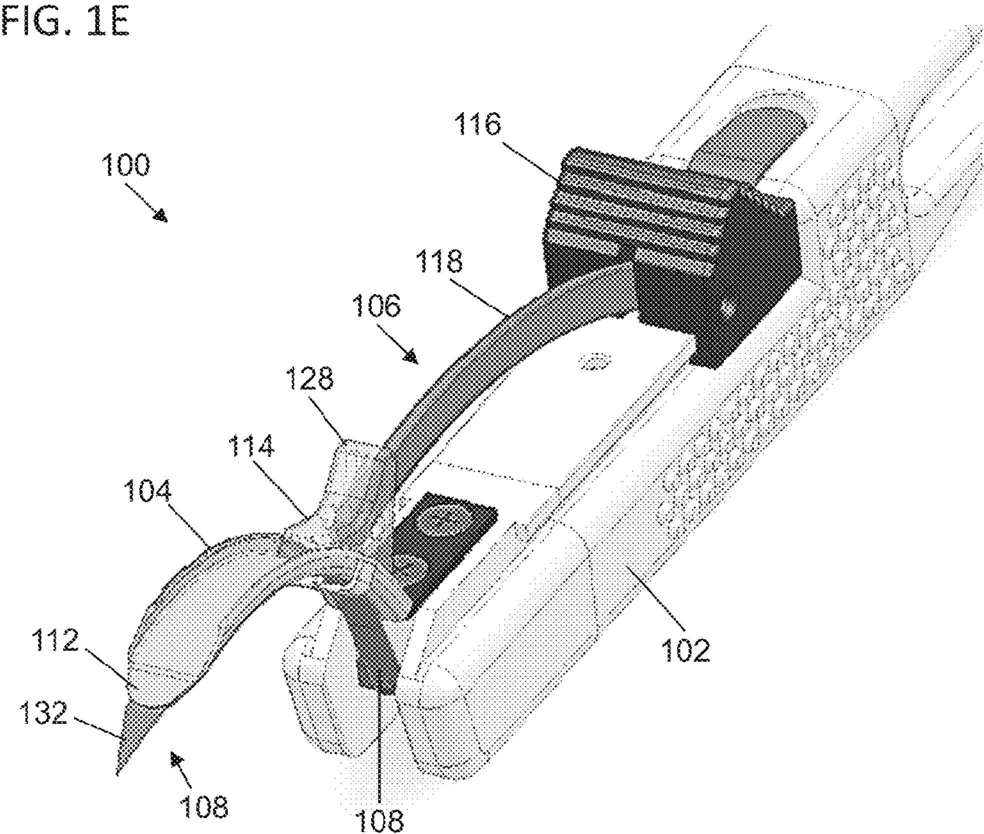
Figure 1F:
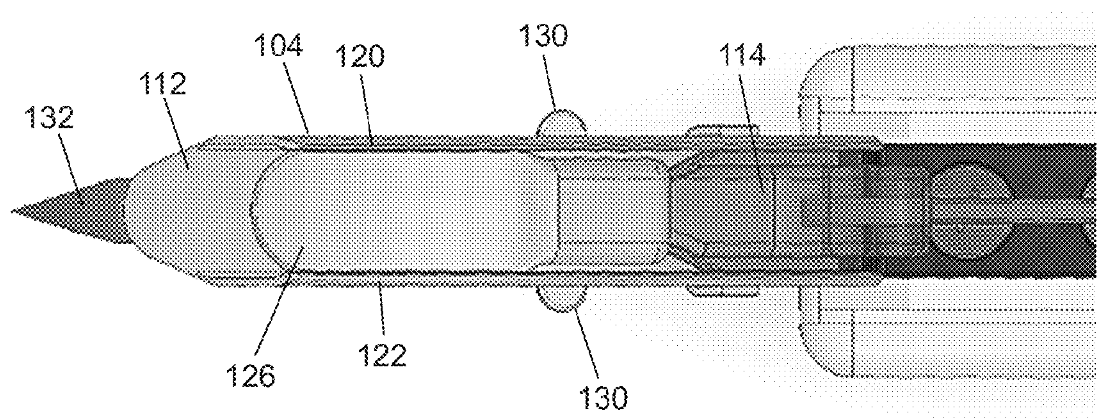
FIG. 1F shows a top view of a distal portion of the delivery device of FIG. 1A.

In some variations, the tongue member (104) may comprise one or more depth stops which may stop or otherwise hinder advancement of the tongue member (104) relative to tissue. For example, in the variation of the delivery device (100) shown in FIGS. 1A-1H, the tongue member (104) may comprise one or more projections (130) extending from one or both sides of the tongue member (104). For example, FIG. 1F shows a top view of a distal portion of the delivery device (100), and as shown there, the tongue member (104) may comprise a projection (130) extending from each side of the tongue member (104). In other variations, the tongue member (104) may comprise one projection (130) extending from only one side of the tongue member (104). Generally, the projections (130) may increase the width of the tongue member (104), and may engage tissue during advancement of the tongue member (104). For example, when the tongue member (104) is advanced through an opening formed in the conjunctiva, the opening of the conjunctiva may fit closely enough around the tongue member (104) during advancement of the tongue member (104) such that the projections (130) may catch on or otherwise press against the conjunctiva. This engagement between the projections (130) and the conjunctiva may resist advancement of the projections (130) past the opening of the conjunctiva. Distance between the tip (112) and the projections (130) may set the distance the tip (112) of the tongue member (104) will be advanced into the orbit when the projections (130) engage tissue. Accordingly, a user may advance the tongue member (104) until the projections (130) resist further advancement, which may indicate to the user how far the tip (112) of the tongue member (104) has been advanced. For example, the projections (130) may be positioned such that the tip (112) of the tongue member is positioned between the lacrimal gland and the frontal process of the orbit when the projections (130) engage an opening in the conjunctiva.

While the projections (130) are shown in FIGS. 1A-1H as being fixed relative to the tongue member, in other variations the projections (130) may be adjustable relative to the tongue member (104). When the projections (130) are adjustable relative to the tongue member (104), a user may adjust the positioning of the projections (130) to control a penetration depth of the tip (112) of the tongue member (104). Additionally, while shown in FIG. 1A as comprising projections, the tongue member (104) may comprise any suitable structure to help control the advancement of the tongue member (104). For example, in some variations the tongue member (104) may comprise a distal portion and a proximal portion having a larger width than the proximal portion. In these variations, the distal portion tongue member (104) may be advanced through a tissue opening until the proximal portion of the tongue member (104) catches on the tissue opening. In other variations, the tongue member (104) may comprise one or more notches along the tongue member. In these variations, when the tongue member (104) is advanced far enough through a tissue opening such that the notches reach the opening, the tissue opening may contract (e.g., due to elasticity of the tissue) into the notches and may resist further advancement. In still other variations, the tongue member (104) may comprise one or more markers positioned along the length of the tongue member (104). In these variations, a user may advance the tongue member (104) through a tissue opening until a specific marker reaches the tissue opening, at which point the user may know that the tip (112) of the tongue member (104) has been advanced a depth indicated by that marker. It should also be appreciated that the delivery devices described here need not comprise any depth stops or markers.

As mentioned above, in some variations the delivery device (100) may comprise an ejector. In these variations, the ejector (106) may cooperate with the tongue member (104) to deliver an implant. For example, in the variation of the delivery device (100), the ejector (106) may comprise a pusher (114), a control slider (116), and a linkage (118) connecting the pusher (114) to the control slider (116). The pusher (114) may be slidably connected to the tongue member (104), and the control slider (116) may be slidably connected to the handle (102). A user may advance the control slider (116) relative to the handle (102), and the connection between the control slider (116) and the pusher (114) provided by the linkage (118) may cause advancement of the pusher (114) along the tongue member (104). Similarly, withdrawal of the control slider (116) relative to the handle (102) may proximally withdraw the pusher (114) relative to the tongue member (104).

In use, the ejector (106) may be used to deliver an implant from the delivery device (100). In some variations, an implant may be slidably connected to the tongue member (104). For example, as shown in FIG. 1C, the tongue member (104) may comprise a first lip (120) on a first side of the tongue member (104) and a second lip (122) on an opposite side of the tongue member (104). The first lip (120) and the second lip (122) may form a track (124) along at least a portion of the length of the tongue member (104). In the variation of the delivery device (100) shown in FIG. 1A, the first lip (120), the second lip (122) and corresponding track (124) may extend along the tongue member (104) from the handle (102) to a proximal end of the tip (112). In other variations, the first lip, second lip, and track may extend along the entire length of the tongue member (104).

When the tongue member (104) comprises a track (124), the pusher (114) of the ejector (106) may be slidably connected to the tongue member (104) along the track (124). Additionally, as shown in a perspective view in FIG. 1D and a top view in FIG. 1F, an implant (126) may be positioned such that it is slidably received in the track (124). In these variations, the implant (126) may be positioned such that the first lip (120) and the second lip (122) may hold the implant (126) in engagement with the tongue member (104). To deliver the implant (126) from the tongue member (104), the pusher (114) may be advanced (e.g., by advancing the control slider (116)) into contact with the implant (126) and may be further advanced to push the implant (126) along the track (124) until the implant (126) clears the track (124) and is thereby released from the tongue member (104).

In some variations in which the delivery device (100) comprises an ejector (106) having a pusher (114), the pusher (114) may comprise one or more structures that may be configured to limit advancement of the pusher (114) relative to tissue. For example, in the variation of the delivery device (100) shown in FIGS. 1A-1F, the pusher (114) may have a stop portion (128) having a height sufficient to stop advancement of the pusher (114) relative to a specific tissue structure. For example, when the delivery device (100) is used to advance the tongue member (104) between the eyeball and the frontal process of the orbit, the stop portion (128) may be dimensioned to contact the orbital fossa (e.g., the supraorbital process) when the pusher (114) is advanced along the tongue member (104). When the tongue member (104) is advanced between the eyeball and the orbital fossa to position the tip (112) of the tongue member (104) at a target position, the pusher (114) may be advanced (e.g., via advancement of the control slider (116)) until the stop portion (128) contacts the orbital fossa. At this point, the pusher (114) may be stopped from forward movement relative to the orbital fossa (e.g., which may prevent or resist the pusher (114) from moving between the eyeball and the frontal process of the orbit), but continued advancement of the control slider (116) relative to the handle (102) may cause retraction of the handle (102) and tongue member (104) relative to the tissue. The retraction of the tongue member (104) may pull some or all of the tongue member (104) out of the tissue opening, but the engagement between the pusher (114) and the implant (126) may prevent the implant (126) from being withdrawn, and may result in delivery of the implant (126) from the delivery device.

As mentioned above, in some variations the delivery device (100) may comprise a piercing member (108) configured to form an opening in tissue such as the conjunctiva. In some variations where the delivery device (100) comprises a piercing member (108), the piercing member (108) may be selectively moveable between a retracted configuration and a piercing configuration. For example, in the variation of the delivery device (100) shown in FIGS. 1A-1F, the piercing member (108) may be selectively moveable between a retracted configuration (such as shown in FIG. 1C), in which a piercing tip (132) of the piercing member (108) is retracted relative to the tip (112) of the tongue member (104), and a piercing configuration (as shown in FIGS. 1E and 1F), in which the piercing tip (132) of the piercing member (108) extends beyond the tip (112) of the tongue member (104). In these variations, the piercing member (108) may be placed in a piercing configuration, and the delivery device (100) may be advanced to drive the piercing tip (132) of the piercing member (108) through tissue (such as the conjunctiva) to form an opening therein. Once the opening has been formed, the piercing member (108) may be placed in the retracted configuration, which may help prevent the likelihood that the piercing member (108) damages tissue beyond the tissue opening.

The piercing member (108) may be moveable between piercing and retracted configurations in any suitable manner. For example, in some variations, the handle (102) may comprise one or more controls which may be configured to move the piercing member (108) between the piercing and retracted configurations. In variations where the delivery device comprises an ejector, one or more portions of the connector may be configured to move the piercing member (108) between the piercing and retracted configurations.

In variations where the delivery devices described here comprise both an ejector configured to advance an implant and a piercing member, it may be desirable to configure the delivery device such that the piercing member is prevented from moving to a piercing configuration while the ejector is delivering an implant. For example, in the variation of the delivery device (100) shown in FIGS. 1A-1F, the control slider (116) of the ejector (106) may be configured to control both delivery of the implant (126) and movement of the piercing member to a piercing configuration. Specifically, the control slider (116) may be configured such that advancement of the control slider (116) advances the pusher (114) to advance and deliver an implant (126) (such as described above), while retraction of the control slider (116) may contact a mechanism to move the piercing member (108) to a piercing configuration. Because the control slider (116) requires retraction to move the piercing member (108) to a piercing configuration and advancement to deliver the implant, a user may be prevented from inadvertently moving the piercing member (108) to a piercing configuration when the user is advancing the control slider (116) to deliver an implant.

Figure 1G:
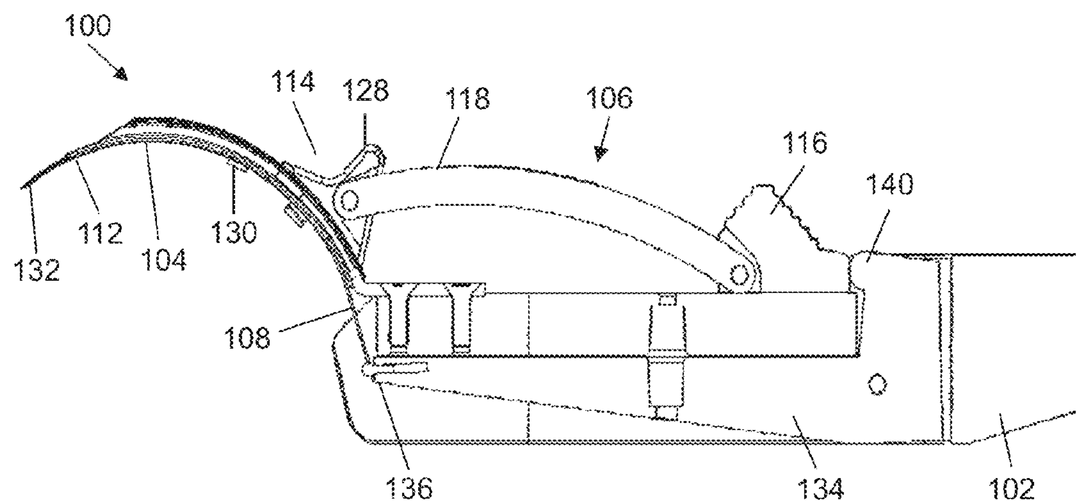
FIGS. 1G and 1H show cross-sectional side views a distal portion of the delivery device of FIG. 1A.
Figure 1H:
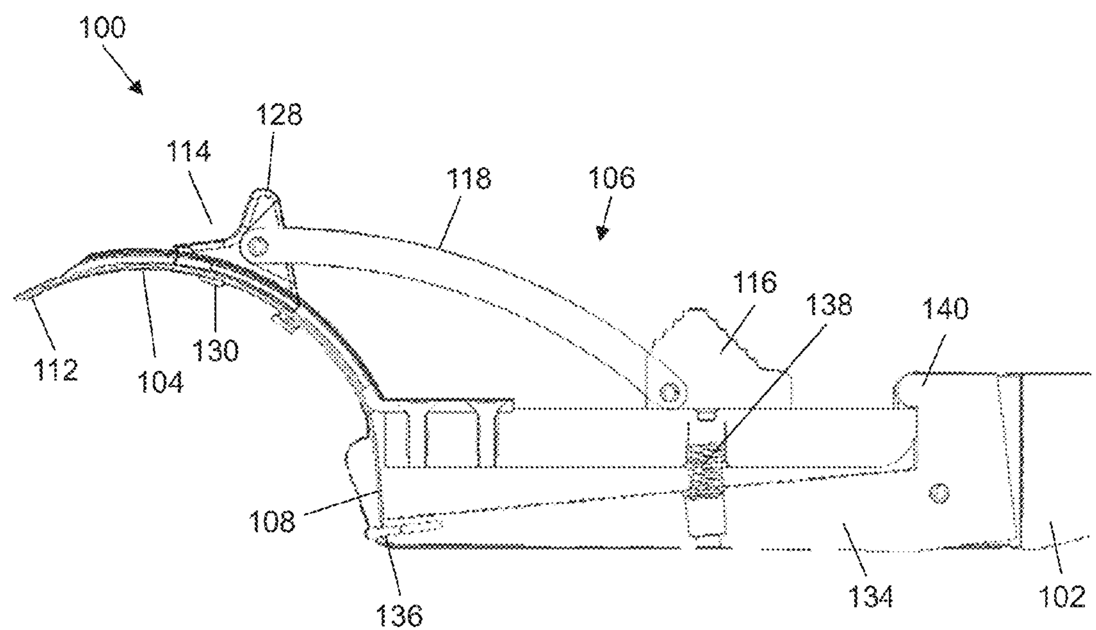

FIGS. 1G and 1H depict cross-sectional side views of the delivery device (100) depicting an illustrative mechanism by which retraction of the control slider (116) may move the piercing member (108) to a piercing configuration. In this variation, the handle (102) may comprise a rocker (134) that is pivotably mounted to the handle (102). A first end (136) of the rocker (134) may be connected to the piercing member (108), and may be configured such that the rocker (134) may be rotated relative to the handle (102) in a first direction to a first position (as shown in FIG. 1G), wherein rotation in the first direction to the first position advances the piercing member (108) relative to the tongue member (104) (e.g., to advance the piercing tip (132) of the piercing member (108) past the tip (112) of the tongue member (104) to place the device in the piercing configuration). The rocker (134) may be further configured such that the rocker (134) may be rotated relative to the handle (102) in a second direction opposite the first direction to a second position (as shown in FIG. 1H), wherein rotation of the rocker (134) in the second direction retracts the piercing member (108) relative to the tongue member (104) (e.g., to move the piercing member (108) to the retracted configuration). The handle (102) may further comprise a spring (138) (not shown in FIG. 1G) that pushes against the rocker (134) to bias the rocker (134) toward the second position, thereby biasing the piercing member (108) toward the retracted configuration.

The control slider (116) may be configured such that retraction of the control slider (116) along the handle (112) moves the control slider (116) into contact with a second end (140) of the rocker (134). The control slider (116) may press against the second end (140) of the rocker (134) to overcome the biasing force provided by the spring (138), and this may rotate the rocker (134) in the first direction and move the piercing member (108) to the piercing configuration (as shown in FIG. 1G). Subsequent advancement of the control slider (116) may disengage the control slider (116) from the rocker (134), thereby allowing the spring (138) to rotate the rocker (134) in an opposite direction to return the piercing member (108) to the retracted configuration (as shown in FIG. 1H). In this variation, in order to advance the control slider (116) to deliver an implant (as discussed above), the control slider (116) needs to be moved out of engagement with the rocker (134). Since the spring (138) biases the delivery device to the retracted configuration when the control slider (116) is not in contact with the rocker (134), a user may be prevented from advancing the control slider (116) and delivering an implant with the piercing member (108) in an extended configuration.

Figure 2A:
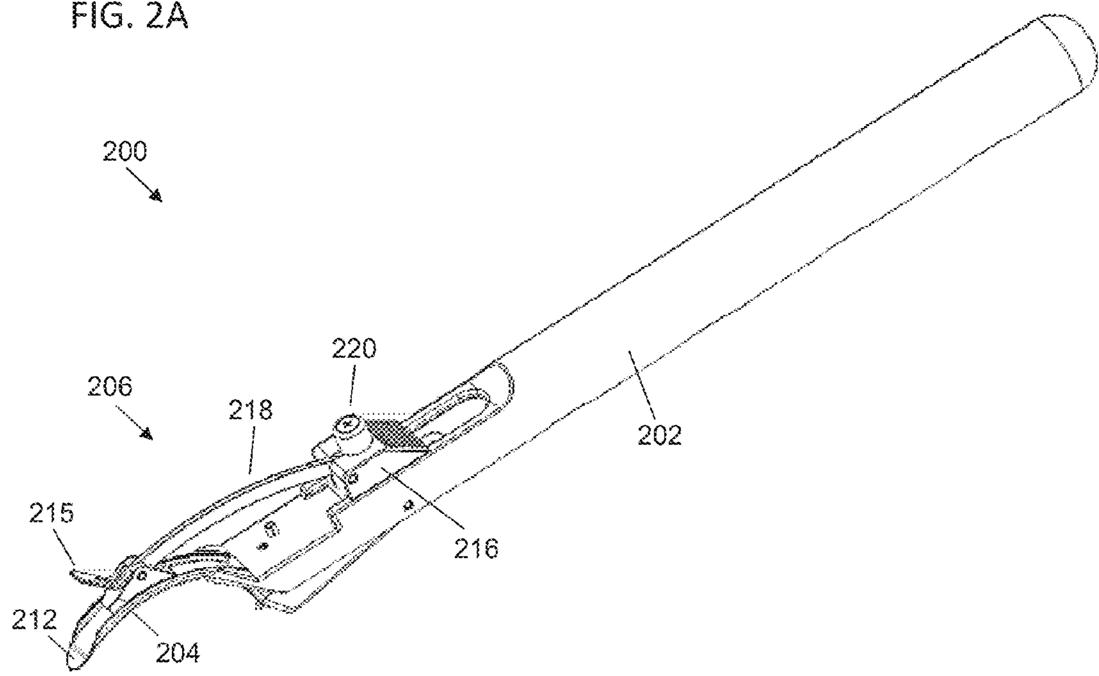
FIG. 2A depicts a perspective view of an illustrative variation of one of the delivery devices described here.
Figure 2B:
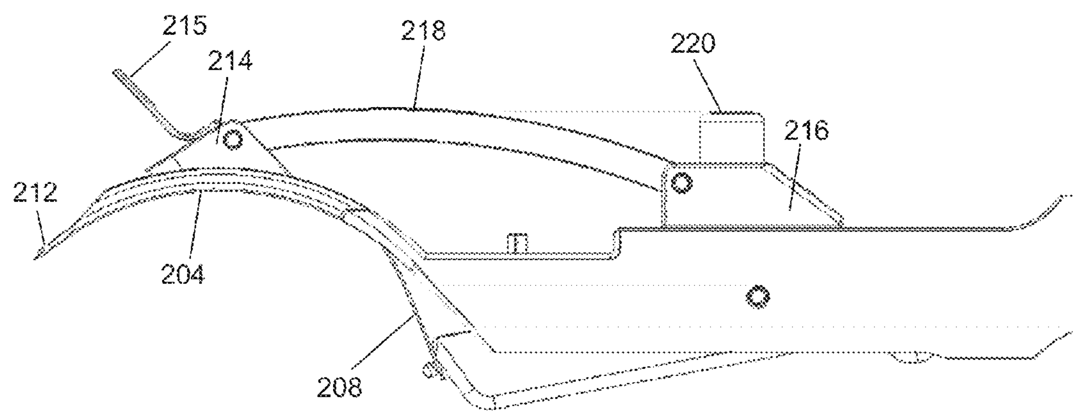
FIGS. 2B and 2C depict side and perspective views, respectively, of the delivery device of FIG. 2A.
Figure 2C:
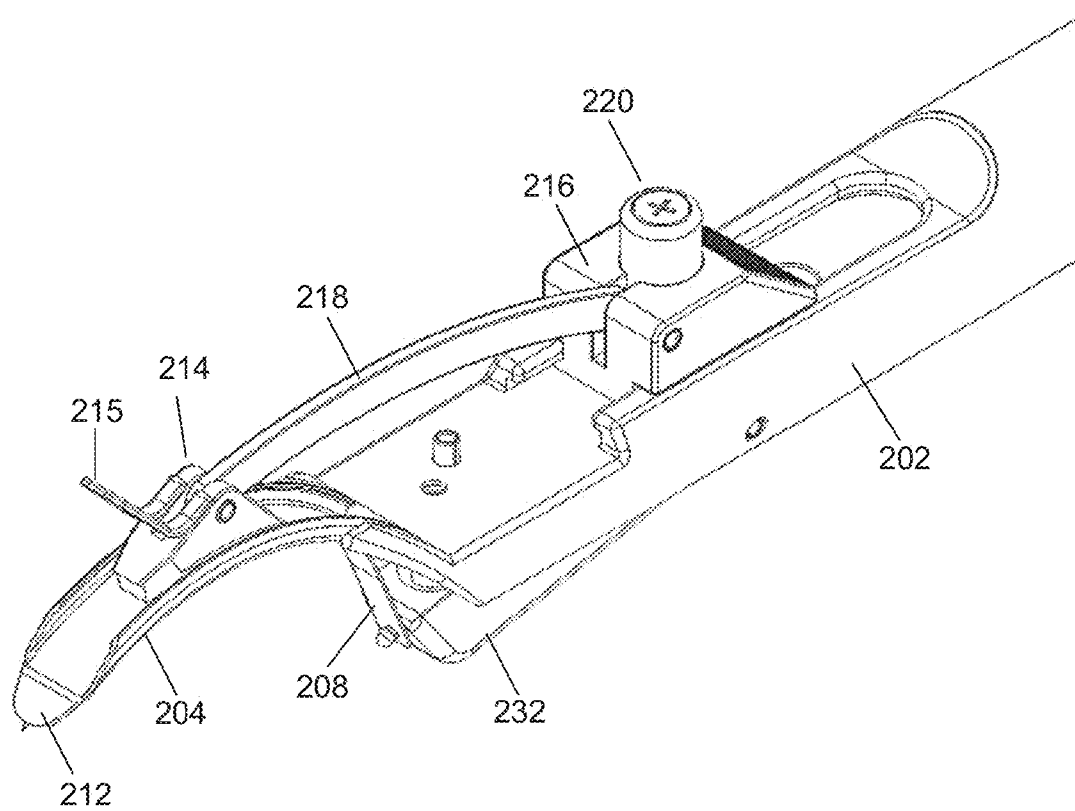

FIGS. 2A-2E depict a second variation of a delivery device (200) which may also be configured to prevent a piercing member from being moved to a piercing configuration during delivery of an implant. FIG. 2A show a perspective view of the delivery device (200), while FIGS. 2B and 2C show a side view and a perspective view, respectively, of a distal portion of the delivery device (200). As shown there, the delivery device may comprise a handle (202), a tongue member (204), an ejector (206), and a piercing member (208), such as described in more detail above. The tongue member (204) and handle (202) may be configured in any suitable manner, such as described in more detail above. As shown there, the ejector (206) may comprise a pusher (214) slidably connected to the tongue member (204), a control slider (216) slidably connected to the handle (202), and a linkage (218) connecting the pusher (214) and the control slider (216). In some variations, the pusher (214) may comprise a stop member (215) attached thereto, such as described above. Advancement and retraction of the control slider (216) may advance and retract, respectively, the pusher (214) relative to the tongue member (204), as described in more detail above. In the variation of the delivery device (200) show in FIGS. 2A-2E, the control slider (216) may comprise a button (220) which may move the piercing member (208) from a retracted configuration (in which a piercing tip (210) of the piercing member (208) is retracted relative to a tip (212) of the tongue member (204)) to a piercing configuration (in which the piercing tip (210) of the piercing member (208) is advanced beyond the tip (212) of the tongue member (204)).

Figure 2D:
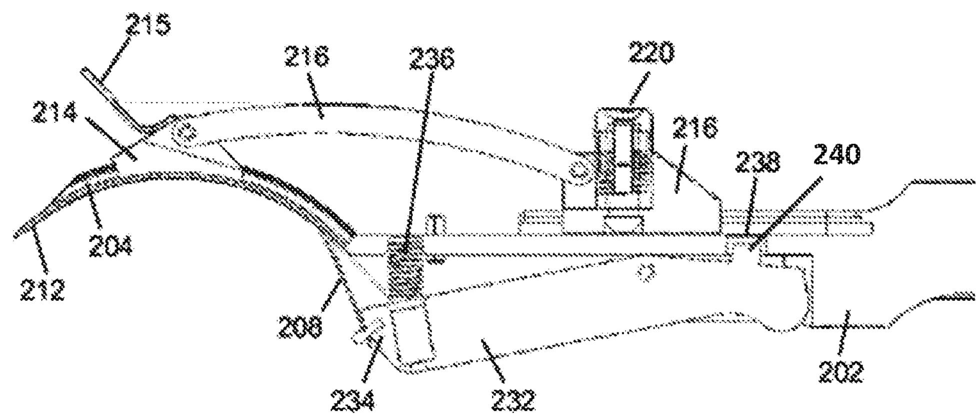
FIGS. 2D and 2E show cross-sectional side views a distal portion of the delivery device of FIG. 2A.
Figure 2E:
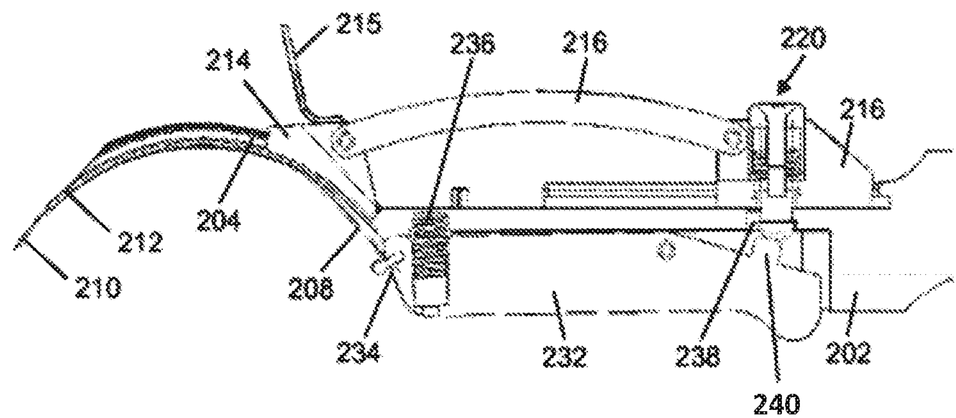

FIGS. 2D and 2E depict an illustrative mechanism by which the button (220) of the control slider (216) may be used to move the piercing member (208) from a retracted configuration to a piercing configuration. The handle (202) may comprise a rocker (232) that is pivotably mounted to the handle (202). A first end (234) of the rocker (232) may be attached to the piercing member (208), and the rocker (232) may be rotated in a first direction toward a first position, wherein rotation of the rocker (232) to the first position may advance the piercing member (208) relative to the tongue member (204) to move the piercing member (208) to the piercing configuration as described above (and as shown in FIG. 2E). The rocker (232) may also be rotated in a second direction opposite the first direction toward a second position, wherein rotation of the rocker (232) to the second position may retract the piercing member (208) relative to the tongue member (204) to move the piercing member (208) to the retracted configuration as describe above (and as shown in FIG. 2D). In some variations, the handle (202) may further comprise a spring (236) which may bias the rocker (232) toward the second position, thereby biasing the piercing member (208) toward the retracted configuration.

In order to move the piercing member (208) to the piercing configuration, a user may depress the button (220). The button (220) may be configured such that depression of the button presses against a second end (240) of the rocker (232) to rotate the rocker (232) in the first direction toward the first position, thereby moving the piercing member (208) to the piercing configuration as discussed above. When the user releases the button (220) (the button (220) may be spring-biased towards an un-depressed position), the spring (236) may return the rocker (232) to the second position, thereby returning the piercing member (208) to the retracted configuration.

In some variations, the delivery device (200) may be configured such that the button (220) may not be depressed during delivery of an implant. For example, in some variations, the control slider (216) of the ejector (206) may be moveable relative the handle (202) between a retracted position (in which the pusher (214) of the ejector is retracted relative to the tongue member (204)) and an advanced position (in which the pusher (214) of the ejector is advanced relative to the tongue member (204)). As discussed in more detail above, advancement of the control slider (216) and the pusher (214) may advance and deliver an implant (not shown). In order to prevent the button (220) from accidentally being depressed during delivery of the implant, the delivery device (200) may be configured such that the button (220) may be depressed when the control slider (216) is in the retracted position (shown in FIG. 2E), and may further be configured such that the button (220) cannot be depressed when the control slider (216) is outside of the retracted position (e.g., when the control slider (216) is in the advanced position). For example, as shown in FIGS. 2D and 2E, the button (220) may be configured to contact the second end (240) of the rocker (232) through an opening (238) in the handle (202). This opening (238) may be configured such that the button (220) may only be depressed when the button (220) is positioned over the opening (238), and the device may be further configured such that button (220) is positioned over the opening (238) only when the control slider (216) is in the retracted position.

The delivery device (200) may further be configured such that the control slider (216) may be prevented from advancing while the button (220) is depressed. For example, when the button (220) is depressed into the opening (238) as shown in FIG. 2E, the portion of the button (220) positioned in the opening (238) may be prevented from advancing relative to the handle (202) by a distal end of the opening (238). This in turn may prevent advancement of the control slider (216) while the button (220) is depressed into the opening (238). Accordingly, to advance the control slider (216) from the retracted position, a user may need to release the button (220), which may cause the piercing member (208) to return to the retracted configuration. In this way, the control slider (216) may only be advanced when the button (220) is not pressed (and the piercing member (208) is in the retracted configuration), and the button (220) may be prevented from inadvertently moving the piercing member (208) to the piercing configuration during advancement of the control slider (216).

In some variations, the delivery devices described here may be configured to absorb blood or other fluids that may escape through a tissue opening as the delivery device is advanced through the opening. For example, in some variations, one or more of the components of the delivery devices described above may be at least partially covered with or otherwise contain a fluid-absorbing material (e.g., one or more porous or sponge materials, one or more woven or non-woven materials, one or more pulps, or the like, which may be formed from collagen, wood pulp, rayon, cotton, or the like). In some variations, one or more portions of a tongue member may be at least partially covered with an absorbent material, such that the tongue member may be configured to absorb fluid contacted by the tongue member. Additionally or alternatively, in variations where the tongue member comprises an ejector having a pusher, one or more portions of the tongue may be covered with an absorbent material.

Figure 6A:
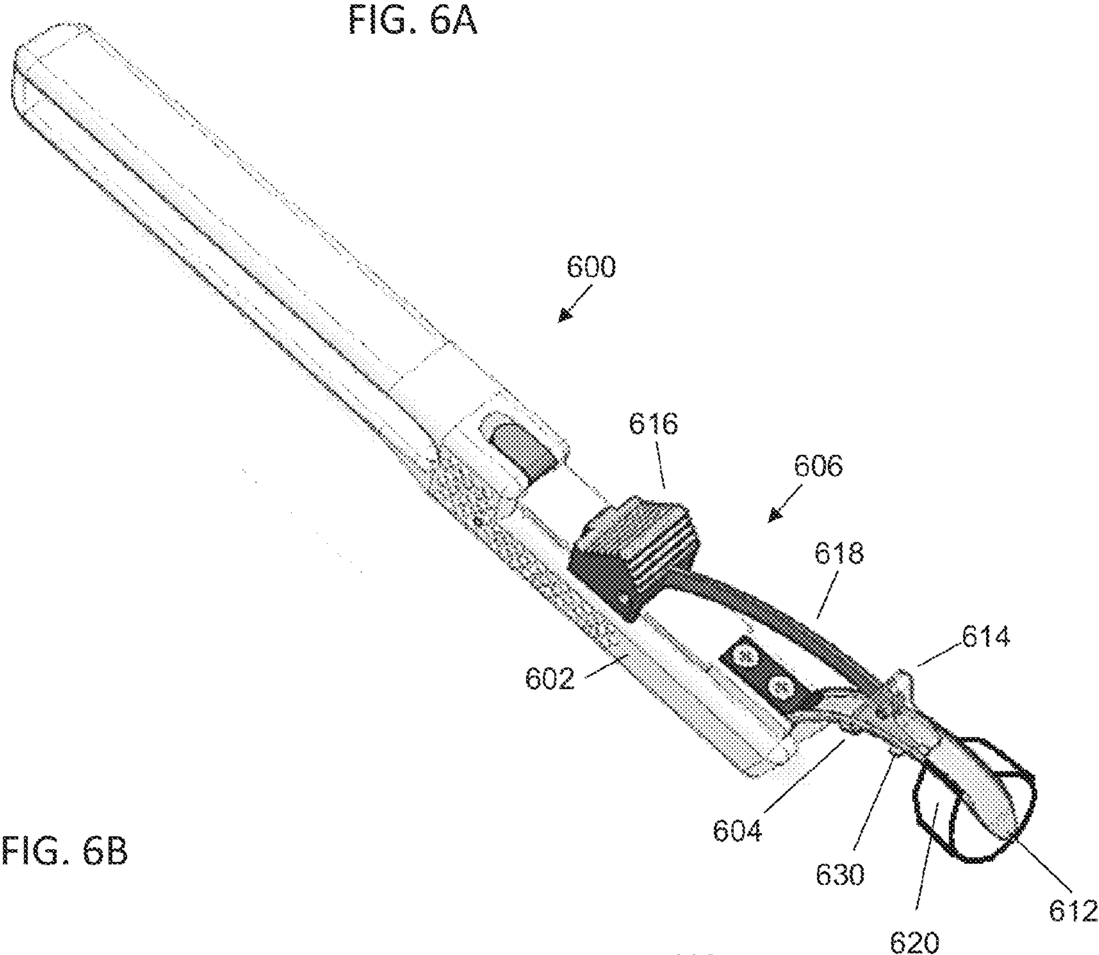
FIG. 6A depicts a perspective view of an illustrative variation of one of the delivery devices described here.
Figure 6B:
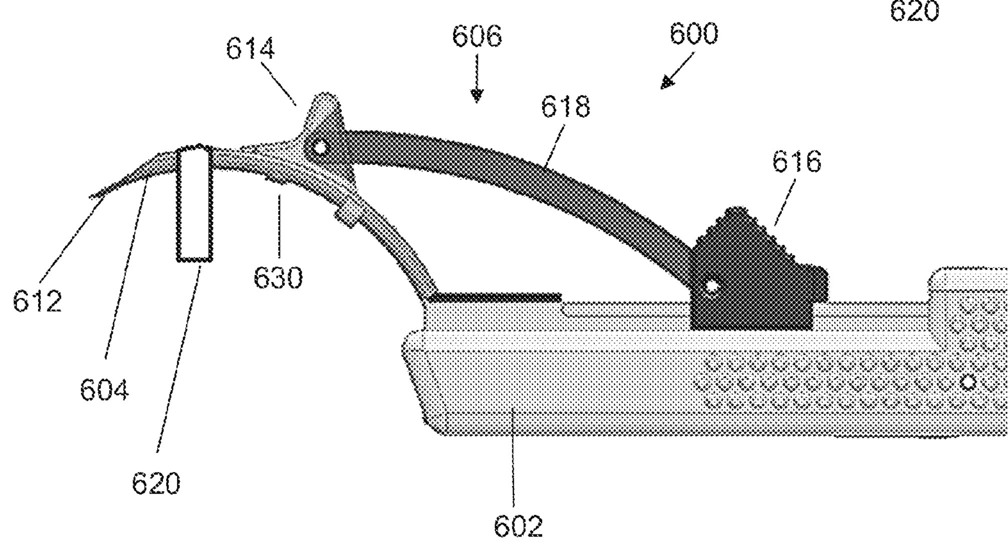
FIG. 6B shows a side view of a distal portion of the delivery device of FIG. 6A.

FIGS. 6A and 6B depict a variation of a delivery device (600) described here which may be configured to absorb fluid. As shown there, the delivery device (600) may comprise a handle (602) and a tongue member (604) having a tip (612). The delivery device (600) may further comprise an ejector (606) comprising a pusher (614), control slider (616), and linkage (618) and/or a piercing member (not shown), such as described in more detail above. Additionally, in some variations the tongue member (604) may comprise projections (630) or other depth stops as discussed above, but need not. Also shown in FIGS. 6A and 6B is an absorbing member (620). The absorbing member (620) is generally configured to absorb fluid, and may be at least partially formed from one or more of the materials discussed above. The absorbing member (620) may be configured such that it may be slidably connected to the tongue member (604). For example, in some variations the absorbing member (620) may comprise a slot or channel that may be placed at least partially around the tongue member (604) to slidably couple the absorbing member (620) thereto. In these variations, when the tongue member (604) is advanced through an opening in tissue (such as the conjunctiva), the absorbing member (620) may be pressed against the tissue opening. When pressed against the opening, the absorbing member (620) may absorb fluid (e.g., blood) that exits the tissue opening. As the tongue member (604) is further advanced relative to the tissue opening, the absorbing member (620) may be too large to fit through the opening and the tongue member (604) may slide relative to the absorbing member (620). Accordingly, the tongue member (604) may be advanced into the opening while maintaining the absorbing member (620) at the tissue opening.

In variations where the tongue member (604) comprises projections (630), such as shown in FIGS. 6A and 6B, the projections (630) may be configured to catch against a proximal end of the absorbing member (620), when the tongue member (604) is advanced relative to the absorbing member (620). In these variations, when the projections (630) contact the absorbing member (620), the projections (630) may resist advancement relative to the absorbing member (620). If the absorbing member (620) is positioned against the tissue opening, the absorbing member (620) may be prevented from further advancement, which may in turn resist further advancement of the projections (630) and the tongue member (604). In other variations, the projections (630) may be configured to advance through the absorbing member (620) (e.g., through one or more lumens or channels (not shown) in the absorbing member (620)) as the tongue member (604) is advanced, and the projections (630) may directly engage the tissue opening, as described in more detail above.

Figure 3A:
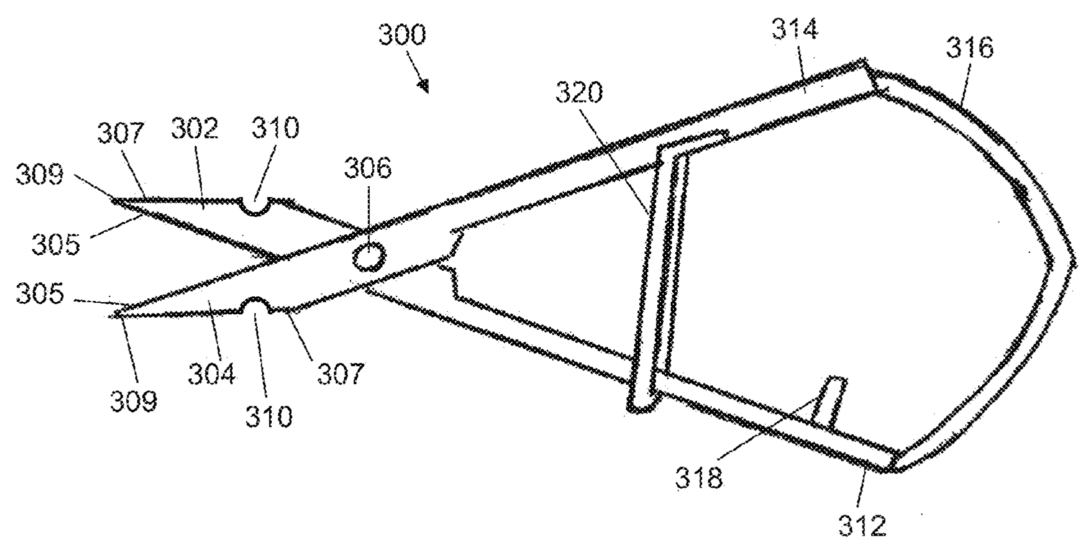
FIGS. 3A and 3B depict a variation of a piercing device suitable for use with the systems described here.
Figure 3B:
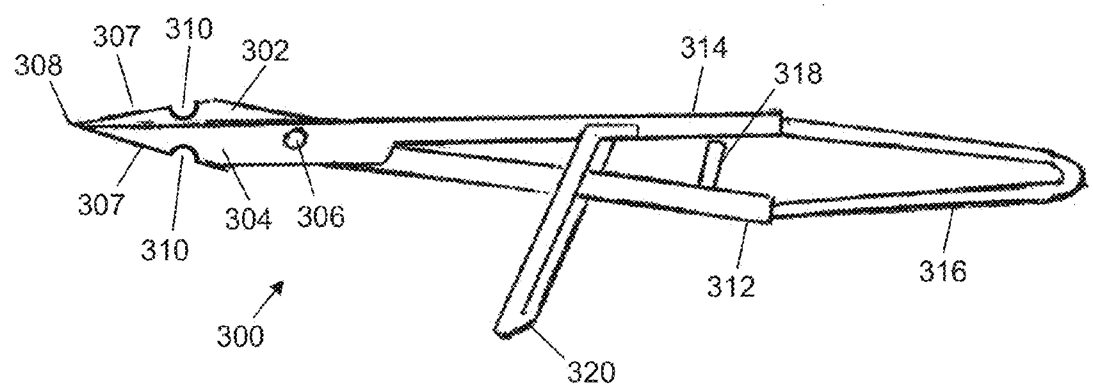

As mentioned above, in some variations, the delivery devices described here do not comprise a piercing member. In some of these variations, the systems described here may comprise a second device that may be used to form an opening in tissue such as the conjunctiva. For example, FIGS. 3A and 3B illustrate a variation of a device configured to puncture or cut a tissue (e.g., the conjunctiva) to form an opening therein. FIG. 3A shows a side view of the piercing device (300). As shown there, the piercing device (300) may comprise a first blade member (302) rotatably connected to a second blade member (304) via a pivot point (306). The first (302) and second (304) blade members may each have an inner edge (305), an outer edge (307), and a tip (309), and may cooperate to create an opening in tissue (such as the conjunctiva). In some instances, the first (302) and second (304) blade members may be used to expand the opening, as will be described in more detail below. Specifically, to create an opening in the tissue, the first (302) and second (304) blade members may be positioned in a first configuration (e.g., by rotating the first blade member (302) relative to the second blade member (304)) in which the tips (309) of the first (302) and second (304) blade members are aligned and coincide to form a point (308), as shown in a side view in FIG. 3B. When the first (302) and second (304) blade members are positioned in the first configuration, the point (308) may be sufficiently sharp to pierce tissue such as the conjunctiva. Accordingly, the first (302) and second (304) blade members may be positioned in the first configuration, and the point (308) may be pressed against a target tissue (e.g., the conjunctiva) to pierce that tissue and form an opening therein. It should be appreciated that in some variations, the first (302) and second (304) blade members may be used to cut tissue and form an opening as the blade members are rotated toward the first configuration, as will be discussed in more detail below, and may be advanced into the opening when in the first configuration.

Once the point (308) has formed an opening in the target tissue (or the blade members have been inserted in an opening formed in the tissue, such as by cutting the target tissue with the blade members), the first (302) and second (304) blade members may be moved to a second configuration to expand the opening formed in the tissue. Specifically, the first blade member (302) may be rotated relative to the second blade member (304) (e.g., around the pivot point (306)) to move the tips of the first (302) and second (304) blade members away from each other, such as shown in a side view in FIG. 3A. As the first (302) and second (304) blade members move from the first to the second configuration, the outer edges (307) of the blade members move away from each other. The outer edges (307) of the blade members may in turn push against tissue of the opening to stretch or otherwise enlarge the opening in the tissue. With the tissue opening stretched, one or more delivery devices (such as those described above) may be advanced through the opening and may be used to perform one or more additional steps of the methods described here.

As the outer edges (307) of the blade members are separated, the tissue opening may have a tendency to slide relative to the blade members (e.g., slipping off the front of the piercing device (300) or slipping toward the pivot point (306)). This may interfere with the ability of the first (302) and second (304) blade members to stretch the tissue opening. Accordingly, in some variations, the piercing device (300) may comprise one or more features to help temporarily secure the first (302) and/or second (304) blade members relative to tissue. For example, in some variations, at least one of the first and second blade members comprises a notch. In the variation shown in FIGS. 3A and 3B, each of the first (302) and second (304) blade members comprise a notch (310) in the outer edge (307) of the respective blade members. It should be appreciated, however, that in some variations only the first blade member (302) may comprise a notch (310), only the second blade member (304) comprises a notch (310), or neither of the blade members comprise a notch. Generally, a notch (310) on a blade member may reduce the cross-sectional area of that blade member. When the first (302) and second (304) blade members are placed in a first configuration and advanced to puncture tissue, the piercing device (300) may be further advanced until the notches (310) of the first (302) and second (304) blade members reach the opening. The tissue opening may have an elasticity that may cause the tissue opening to contract into the notches (310). This tension may help hold tissue within the notches (310), and may reduce the likelihood that the tissue opening will slide relative to the first (302) and/or second (304) blade members as the blade members are moved from the first configuration to the second configuration to expand the opening.

The first (302) and second (304) blade members may be moved between the first and second configurations in any suitable manner. For example, in the variation of the piercing device (300) shown in FIGS. 3A and 3B, each of the first (302) and second (304) blade members may be attached to a first grip and a second grip, respectively (labeled as (312) and (314), respectively). Rotation of the first grip (312) relative the pivot point (306) may rotate the first blade member (302) relative to the pivot point (306), while rotation of the second grip (314) relative to the pivot point (306) may rotate the second blade member (302) relative to the pivot point (306). In the variation shown in FIGS. 3A and 3B, the piercing device (300) may be configured such that rotating the first grip (312) toward the second grip (314) rotates the first blade member (302) toward the second blade member (304) (e.g., toward the first configuration) and rotating the first grip (312) away from the second grip (314) rotates the first blade member (302) away from the second blade member (304) (e.g., toward the second configuration). In other variations, the piercing device (300) may instead be configured such that rotating the first grip (312) toward the second grip (314) rotates the first blade member (302) away the second blade member (304) (e.g., toward the second configuration) and rotating the first grip (312) away from the second grip (314) rotates the first blade member (302) toward from the second blade member (304) (e.g., toward the first configuration). In either of the above embodiments, a user may manipulate the first (312) and second (314) grips to move the first (302) and second (304) blade members between the first and second configurations.

In some variations, the piercing device may be biased toward one of the first and second configurations. For example, in the variation shown in FIGS. 3A and 3B, the piercing device (300) may comprise a spring member (316) connecting the first (312) and second (314) grips. As shown there, the spring member (316) may bias the first (312) and second (314) grips away from each other, which in turn may bias the first (302) and second (304) blade members toward the second configuration. In these instances, a user may squeeze the first (312) and second (314) grips together to overcome the biasing force provided by the spring member (316) and position the first (302) and second (304) blade members together in the first configuration. Releasing or otherwise reducing the squeezing force applied to the first (312) and second (314) grips may allow the spring member (316) to move the first (302) and second (304) blade members toward the second configuration. It should be appreciated that in some variations, the piercing device (300) may comprise a spring member that is configured to bias the first and second grips toward each other, which in turn may bias the first and second blade members toward the first configuration. In still other variations, the piercing device need not be biased toward any particular position.

The piercing device may further be configured to limit the range of motion of the first (312) and second (314) grips, which thereby limits the range of motion of the first (302) and second (304) blade members. For example, in the variation shown in FIGS. 3A and 3B, the piercing device (300) may comprise two range-limiting elements. Specifically, one of range-limiting element may limit how closely the first grip (312) may be rotated toward the second grip (314) and the other range-limiting element may limit how far the first grip (312) may be rotated away from the second grip (314). It should be appreciated that in some variations, the piercing device (300) may comprise only a range-limiting element configured to limit rotation of the first grip (312) toward the second grip (314), may comprise only a range-limiting element configured to limit rotation of the first grip (312) away from the second grip (314), or may not comprise any range-limiting element.

The range-limiting elements may be any structure suitable to limit the rotation of the first grip (312) relative to the second grip (314). In the variation shown in FIGS. 3A and 3B, the piercing device (300) comprises a range-limiting pin (318) positioned between the first (312) and second (314) grips. The range-limiting pin (318) may be attached to one of the grips (e.g., the first grip (312) in the variation shown in FIGS. 3A and 3B) and may act as a stop to rotation of the first grip (312) toward the second grip (314). For example, as shown in FIG. 3B, the first grip (312) may be rotated toward the second grip (314) until the range-limiting pin (318) contacts the second grip (314). This contact between the range-limiting pin (318) and the second grip (314) may prevent the first grip (312) from rotating further toward the second grip (314). In some variations, the range-limiting pin (318) may be configured such that it stops rotation between the first (312) and second (314) grips when the first (302) and second (304) blade members reach the first configuration. In this way, a user may position the first (302) and second (304) blade members in the first configuration by squeezing the first (312) and second (314) grips toward each other until the range-limiting pin (318) prevents further rotation of the grips. This may also act to prevent the first (302) and second (304) blade members from over-rotating past the first configuration.

Additionally, the piercing device (300) may comprise a range-limiting bar (320) which may limit rotation of the first grip (312) away from the second grip (314). Specifically, the range-limiting bar (320) may be attached to either of the grips (in the variation shown in FIGS. 3A and 3B, the range-limiting bar (320) may be attached to the second grip (314)) and may act as a stop to limit rotation of the first grip (312) away from the second grip (314). For example, the first grip (312) may be free to rotate away from the second grip until it contacts the range-limiting bar (320) (as shown in FIG. 3A). Contact between the range-limiting bar (320)

and the first grip (312) may prevent further rotation of the first grip (312) away from the second grip (314). Accordingly, the range-limiting bar (320) may control how far the first (312) and second (314) grips may be separated. This in turn may control how far the first (302) and second (304) blade members may be separated when in the second configuration. By controlling the possible separation of the first (302) and second (304) blade members, the range-limiting bar (320) may control the amount that the opening formed by the piercing device (300) may be stretched. For example, when each of the first (302) and second (304) blade members comprise a notch (310), the range-limiting bar (320) may be configured to stop rotation of the first (312) and second (314) grips when the distance between the notch (310) of the first blade member (302) and the notch (310) of the second blade member (304) reaches a certain amount (e.g., between about 4 mm and about 8 mm or the like). In some instances, it may be desirable to dilate the opening sufficiently to allow for introduction of one or more portions of a delivery device through the opening. When the tissue is engaged in the notches (310), the controlled separation between the notches may provide a predictable, controlled amount of expansion of the opening.

To use the piercing device (300), a user may initially manipulate the first and second grips to position the first and second blade members in the first configuration (as described above). In the variation shown in FIG. 3B, this may include rotating the first grip (312) toward the second grip (314) (e.g., by squeezing the first and second grips together). When the piercing device comprises a range-limiting element that limits the amount that the first grip (312) may be rotated toward the second grip (314) (such as range-limiting pin (318) depicted in FIGS. 3A and 3B), placing the first and second blade members in the first configuration may comprise rotating the first and second grip members toward each other until the range-limiting element prevents further rotation of the grip members. The user may hold the piercing device (300) in the first configuration, and may advance the point (306) through tissue to puncture the tissue and form an opening therein. The first (302) and second (304) blade members may be advanced into the opening until the notches (310) of the first and/or second blade members reach and engage the opening. With the tissue opening engaged by the notch or notches (310), the first and second grips may be moved to position the first and second blade members in the second configuration. For example, in the variation shown in FIGS. 3A and 3B, the user may release the squeezing force applied to first (312) and second (314) grips, and the spring member (316) may cause the first grip (312) to rotate away from the second grip (314). This in turn may cause the first blade member (302) to rotate away from the second blade member (304), which may stretch the opening engaged by the first (302) and second (304) blade members. In variations where the piercing device comprises a range-limiting element that limits the amount that the first grip (312) may rotate away from the second grip (314) (such as the range-limiting bar (320) depicted in FIGS. 3A and 3B)), the range-limiting element may limit the stretching of the opening.

In some variations, the piercing device (300) may also act as scissors to cut tissue. Specifically, the inner edges (307) of the first (302) and second (304) blade members may be sharpened, such that the inner edges (307) may cut tissue positioned therebetween. For example, the first (302) and second (304) blade members may be positioned in the second configuration, and the piercing device (300) may be positioned with the first (302) and second (304) blade members on either side of a structure to be cut. When the first (302) and second (304) blade members are moved back to the first configuration, the sharpened inner edges (305) of the first (302) and second (304) blade members may cut the structure. In these variations, the first (302) and second (304) blade members may be moved to the first configuration to cut tissue (such as the conjunctiva) to form an opening therein. With the first (302) and second (304) blade members in the first configuration, the tip (308) formed by the blade members may be advanced through the opening, and the first (302) and second (304) blade members may be moved to the second configuration to stretch or otherwise enlarge the opening, as described in more detail above.

Figure 4A:
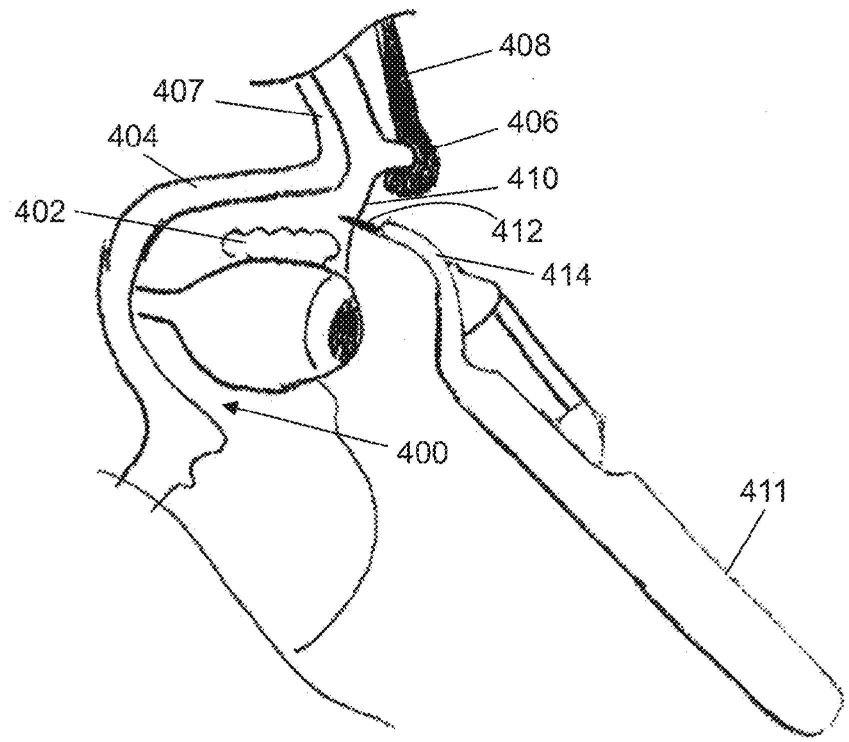
FIGS. 4A-4D depict an illustration variation of one of the methods described here.

FIGS. 4A-4E depict a variation of a method by which the delivery devices described above may be used to deliver an implant in the orbit (400) between the lacrimal gland (402) and the frontal process (404). As shown there, the method may comprise retracting an eyelid (406), such as shown in FIG. 4A. When the eyelid (406) is retracted it may be retracted using one or more fingers, or using one or more devices. For example, in some variations, a hook member (408) may be used to retract and/or hold the eyelid (406) in a retracted position. It should also be appreciated that in some variations, the method does not comprise retracting the eyelid (406), but instead comprises piercing through eyelid (e.g., using one or more of the devices described above).

The method may further comprise piercing the conjunctiva (410) to form an opening therein. In some variations, a delivery device (411) comprising a piercing member (412) may be used to pierce the conjunctiva (410), such as shown in FIG. 4A. The delivery device may be one of the delivery devices described above with respect to FIGS. 1A-1H and 2A-2E. In variations where the piercing member (402) is moveable between a retracted configuration and a piercing configuration (such as described in more detail above), the piercing member (412) may be moved to the piercing configuration, and a piercing tip of the piercing member (412) may be advanced through the conjunctiva (410) to form an opening therein. In other variations, the delivery device (411) does not form the opening in the conjunctiva, but instead a piercing device (such as those described above with respect to FIGS. 3A and 3B) may be used to form the opening in the conjunctiva, in a manner as discussed in more detail above.

In some variations, the method may further comprise dilating the opening formed in the conjunctiva (410). In variations where a piercing member (412) of the delivery device (411) is used to form the opening in the conjunctiva, the delivery device (411) may be further advanced into the opening of the conjunctiva to begin advancing a tongue member (414) of the delivery device (411) into the opening. As the tongue member (414) is advanced into the opening, the tongue member (414) may dilate the opening in the conjunctiva (410) as described above. For example, when the tongue member (414) has a tapered tip, advancement of the tip through the opening may dilate the opening. In variations where a piercing device forms the opening in the conjunctiva (410), the piercing device may also dilate the opening in the conjunctiva (e.g., by rotating a first blade member relative to a second blade member, such as described in more detail above.

Figure 4B:
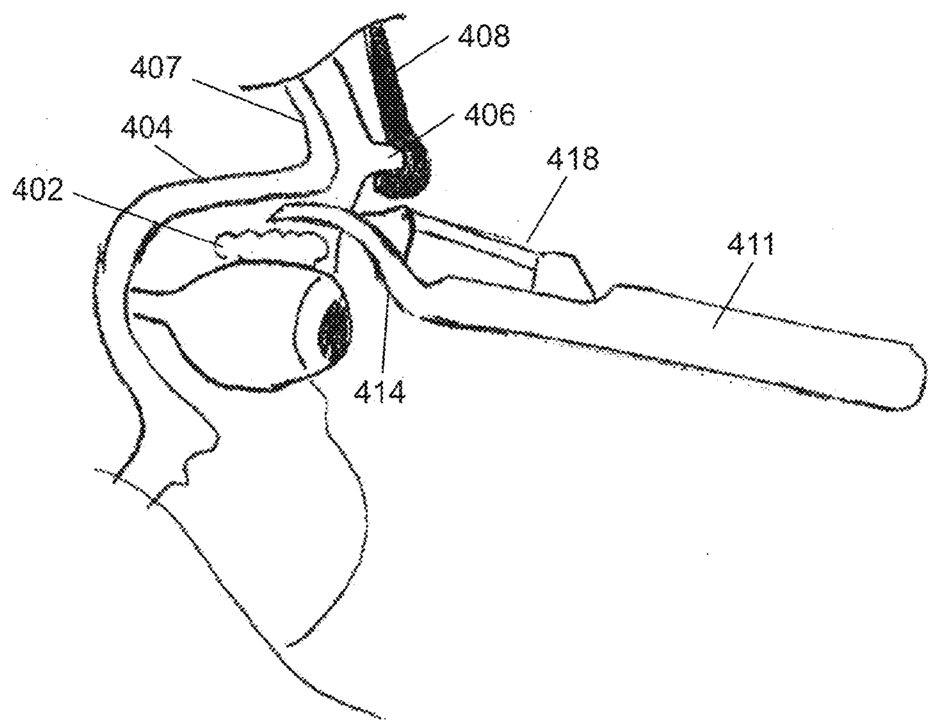

As shown in FIG. 4B, the tongue member (414) may be advanced through the opening in the conjunctiva to form a pocket between tissues beyond the conjunctiva. In variations where the tongue member (414) comprises a piercing member (412) as shown in FIG. 4A, the piercing member (412) may be placed in a retracted configuration during advancement of the tongue member (414). In variations where a piercing device is used to form the opening in the conjunctiva, the piercing device may be removed once the tongue member (414) has been inserted into the opening. The tongue member (414) may be advanced to position a tip of the tongue member (414) at a target position in the orbit (e.g., between the lacrimal gland (402) and the frontal process (404) of the orbit (400)). In variations where the delivery device comprises one or more depth stops or markers, the tongue member (414) may be advanced until the depth stops or markers reach the opening in the conjunctiva (410), which may control the depth of insertion of the tongue member (414).

Figure 4C:
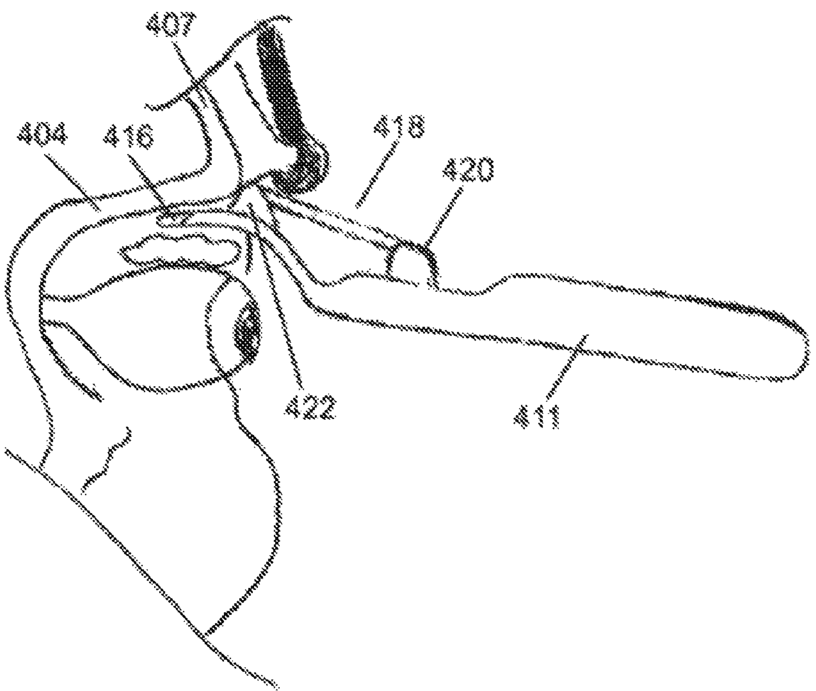
Figure 4D:
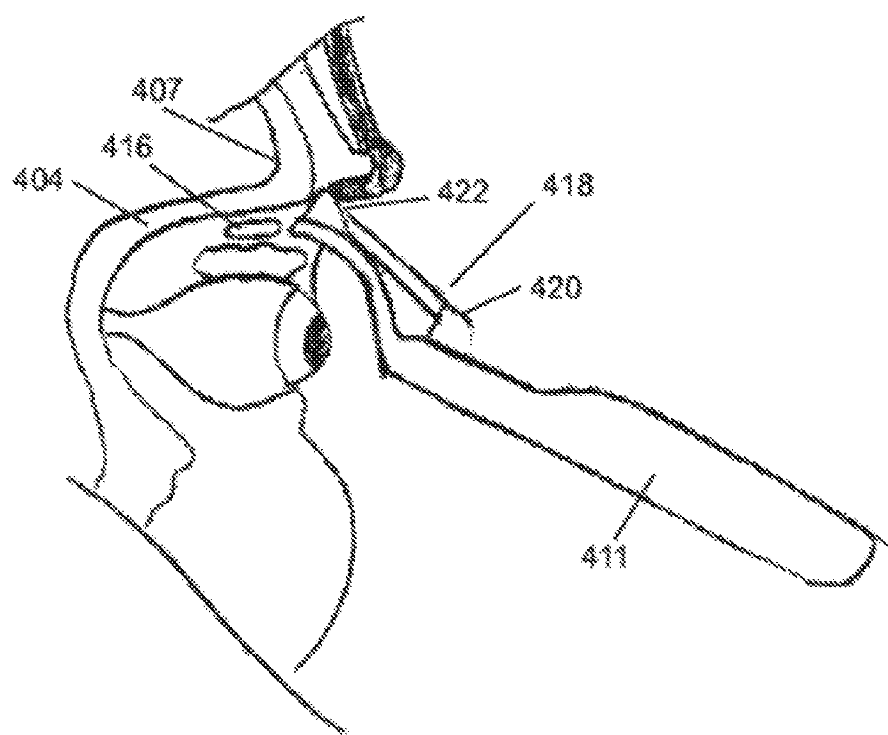

Once the tongue member (414) has been advanced to form a pocket, the delivery device (400) may deliver an implant (416) into the pocket. For example, in variations where the delivery device (400) comprises an ejector (418) (such as described in more detail above), the ejector (418) may deploy the implant (416) (which may be pre-loaded into the delivery device (411)). For example, a control slider (420) of the ejector (418) may be advanced relative to the delivery device (411) to advance a pusher (422) along the tongue member (414). The pusher (422) in turn may push against the implant (416) to begin deploying the implant (416) from the tongue member (414), such as shown in FIG. 4C. In some variations, advancement of the pusher (422) may be advanced until it contacts the frontal process (404), the supraorbital process (407), and/or the upper eyelid as shown in FIG. 4C. In these variations, engagement between the pusher (422) and the bone may prevent further advancement of the pusher (422). Continued advancement of the control slider (420) relative to the delivery device (411) may instead cause the tongue member (414) to be retracted relative the orbit (400), which may result in release of the implant into the pocket formed by the tongue member (414), such as shown in FIG. 4D.

Following delivery of the implant (416), the devices may be removed from the orbit (400), and the opening in the conjunctiva may be closed, as described above. In some variations, the method may further comprise testing the functionality of the implant. For example, in some variations the delivery devices described here may be configured to provide one or more test signals to the implant (e.g., in instances where the implant comprises a stimulator) which may test whether the implant is properly positioned and/or is functioning properly.

Figure 7:
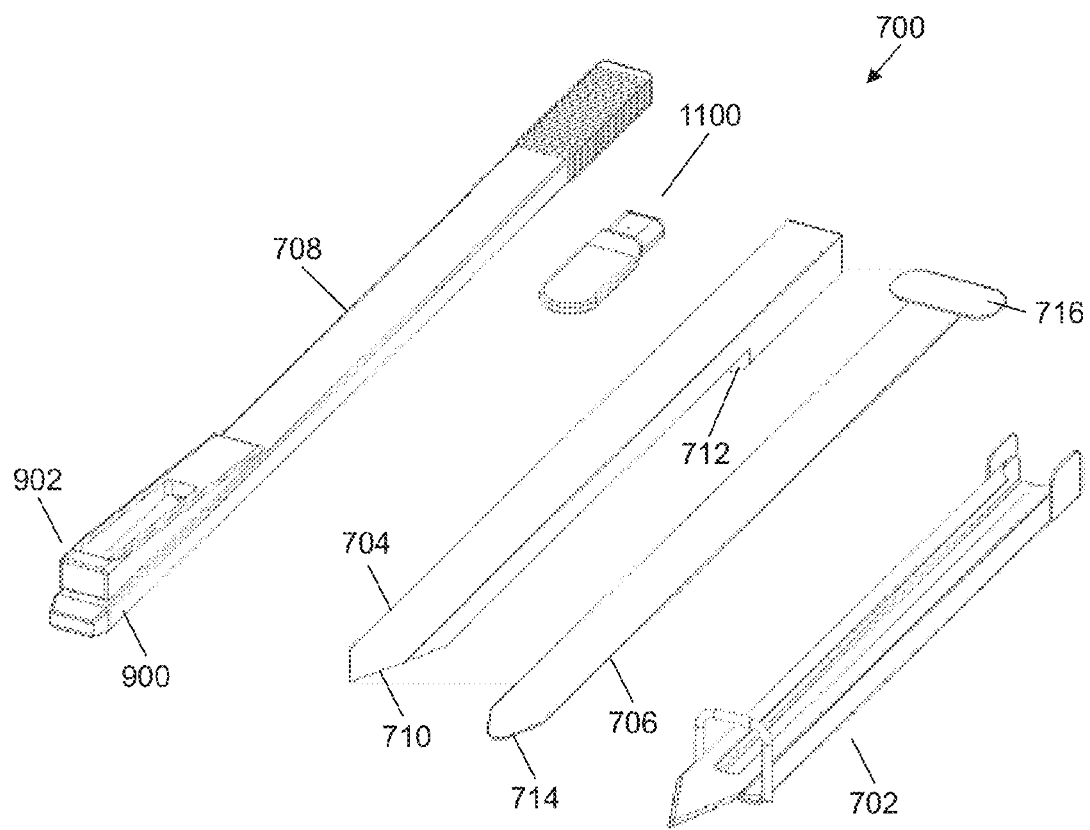
FIG. 7 depicts a perspective view of a variation of a delivery system as described here.

FIG. 7 depicts a delivery system (700) for delivering an implant (1100) to an orbit of a patient. As shown there, the system may comprise a cannula (702), a spacer (704), a tongue (706), and a plunger (708) (although, as discussed in more detail below, the delivery system may comprise a plunger that may act as both a spacer and a plunger). Generally, the cannula (702) may be used to form an opening in a tissue (e.g., an opening in the conjunctiva, an opening in the eyelid and the conjunctiva, or the like) and may separate tissue beyond the opening to a pocket in the tissue (e.g., the pocket may be formed between the periosteum and the orbital bone, between the periosteum and the lacrimal gland, or the like). The spacer (704) may be advanced through a portion of the cannula and into the tissue opening. As the spacer (704) is advanced through the tissue opening, the spacer (704) may expand the tissue opening and the pocket. The tongue (706) may be advanced through the cannula and through the tissue opening, and may further separate tissue to extend the length of the pocket. With the tongue (706) is positioned through the tissue opening, the spacer (704) may be removed and an implant may be advanced through the cannula (702) using the plunger (708). The plunger (708) may also advance the implant through the tissue opening to position the implant in the pocket. Once the implant is positioned in the pocket, the components of the delivery device may be withdrawn from the body, and the tissue opening may be closed in any manner such as discussed above. The components of the delivery system (700), as well as the steps of using the delivery system (700) to deliver an implant, will each be described in more detail below.

Figures 8A, 8B, 8C:
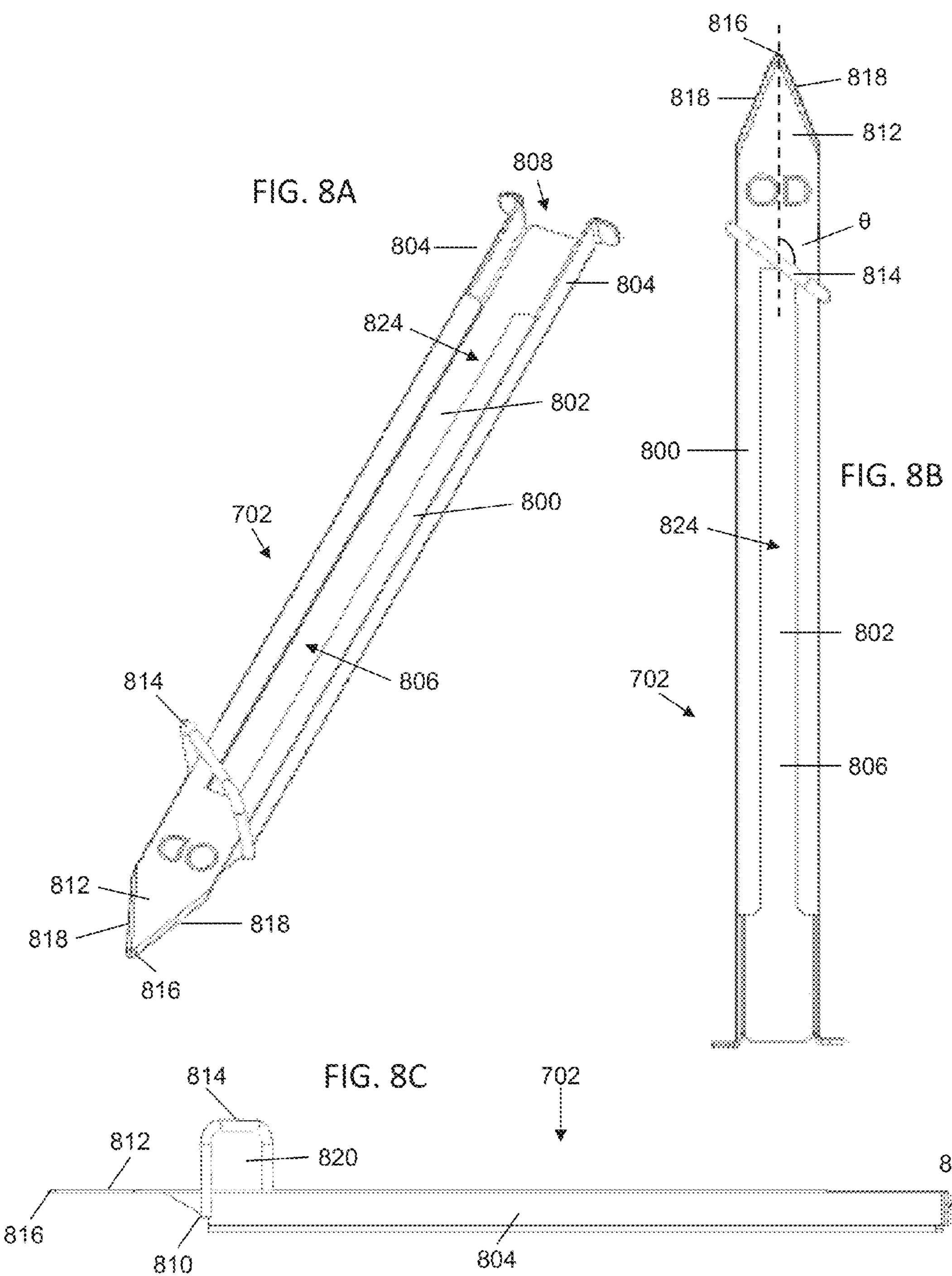
FIGS. 8A-8C depict perspective, top, and side views, respectively, of a variation of a cannula suitable for use with the delivery system of FIG. 7.

FIGS. 8A-8C show perspective, top, and side views, respectively, of a variation of the cannula (702) of the delivery system (700) of FIG. 7. As shown there, the cannula (702) may comprise a top wall (800), bottom wall (802) and first and second side walls (each labeled as (804)), which together may define a channel (806) extending between an inlet (808) and an outlet (810). While the top wall (800) only extends partially along the channel (806) in the variation shown in FIGS. 8A-8C, it should be appreciated that in other variations the top wall (800) may extend along the entire length of the channel (806). The channel (806) may allow for the cannula (702) to guide one or more components relative to the cannula (702), as will be described in more detail below. Each of the walls of the cannula (702) may be formed together as a unitary piece, or some walls may be formed separately and attached (e.g., via bonding, welding, or the like). For example, in some variations, the bottom wall (802) and the first and second side walls (804) may be formed together as a single piece, and the top wall (800) may be formed separately from and may be subsequently attached to the side walls (804). In some of these variations, the bottom wall (802) and the first and second side walls (802) may be formed from a first material or materials (e.g., one or more metals, plastics, polymers, or the like), and the top wall (800) may be formed from a second material or materials (e.g., one or more metals, plastics, polymers, or the like) which may be different from the first material or materials.

Also shown in FIGS. 8A-8C are blade (812) and stop bar (814). The blade (812) may be positioned and arranged to extend beyond the outlet (810) of the channel (806). In the variation shown in FIGS. 8A-8C, the blade (812) may extend from the top wall (800) (e.g., the blade (812) may be formed as part of the top wall (800), or may be formed separately from the top wall (800) and attached thereto). The blade (812) may include a piercing tip (816) configured to puncture tissue to form an opening in tissue (e.g., an opening in the conjunctiva, an opening in the eyelid, or the like). In some variations, the width of the blade (812) may be tapered from the piercing tip (816) (i.e., the width of the blade (812) may increase proximally from the piercing tip (816)), such that advancement of the blade (812) into a tissue opening may expand the tissue opening by increasing the width of the blade (812) positioned in the tissue opening. In some variations, the blade (812) may include one or more cutting edges (818), which may be configured to cut tissue as the blade (812) is advanced into the tissue opening to facilitate dilation of the tissue opening. Additionally, as the blade is inserted past the tissue opening, the blade (812) may separate tissue past the tissue opening to form a pocket in the orbit. In some instances, the blade (812) may be advanced between the periosteum and the orbital bone to form a pocket therebetween. In other instances, the blade (812) may be advanced between the periosteum and another tissue, such as the lacrimal gland, to form a pocket therebetween.

While shown in FIGS. 8A-8C as having a stop bracket (814), it should be appreciated that the cannula (702) need not comprise a stop bracket (814). In variations where the cannula (702) comprises a stop bracket (814), the stop bracket (814) may be configured to limit the advancement of the blade (812) through tissue. Specifically, the stop bracket (814) may be configured to engage a tissue structure during advancement of the blade (812) through a tissue opening, whereby the engagement between the stop bracket (814) and the tissue structure may limit further advancement of the blade (812) into the tissue opening. For example, when the blade (812) is used to form an opening through an eyelid and/or the conjunctiva (as will described in more detail below), the stop bracket (814) may be configured to engage tissue overlying orbital fossa (e.g., the supraorbital process, the orbital process of the zygomatic bone, or the like) to limit further advancement of the blade when the stop bracket (814) engages the orbital fossa.

As shown in FIGS. 8A-8C, the stop bracket (814) may extend away from the top wall (800) by a height (H). The height (H) between the stop bracket (814) and the top wall (800) may be any suitable value, such as, for example, about 1 cm, between about 0.75 and about 1.25 cm, at least about 0.75 cm and the like. As used here, "about" means ±5%. For example, the height may be configured such that the stop bracket (814) is tall enough to engage tissue of the orbital fossa when the blade (812) is advanced between the eye and the orbital fossa. Additionally, in some variations the stop bracket (814) may be configured to define an aperture (820) between the stop bracket (814) and cannula (702) (e.g., between the stop bracket (814) and the top wall (800) of the cannula (702)). The aperture (820) may be sized and configured to allow one or more components of delivery system (700) to be advanced through the aperture (820) during use of the delivery system (700), as will be described in more detail below.

In some variations, the stop bracket (814) may be angled relative to the longitudinal axis of the cannula (700), which may facilitate creation of an opening in the left or right orbit of a patient. Specifically, the stop bracket (814) may be angled to accommodate the contours of the left or right orbit to help increase the surface contact between the stop bracket (814) and the orbital fossa during advancement of the cannula (700). As shown in FIG. 8B, the stop bracket (814) may be positioned at an angle (θ) relative to the longitudinal axis (822) of the cannula (700) in a clockwise direction. The angle (θ) may be any suitable angle. In some variations, the angle (θ) may be about 90 degrees, such that the stop bracket (814) is perpendicular to the longitudinal axis (822) of the cannula (700). In these variations, the cannula (700) may be used to form an opening in either the left orbit or the right orbit, as a similar amount of the stop bracket (814) will contact each orbit when a blade (812) is inserted between the eye and the orbital fossa. In other variations, the angle (θ) may be less than 90 degrees. For example, in the variation shown in FIG. 8B, the angle (θ) may be about 45 degrees. An angle (θ) less than 90 degrees may increase the contact area between the stop bracket (814) and the orbital fossa of a patient's right orbit during advancement of the blade (812) into the right orbit. Conversely, in other variations, the angle (θ) may be greater than 90 degrees, which may facilitate the formation of a tissue opening in the left orbit. For example, in some variations, the angle (θ) may be about 135. An angle (θ) greater than 90 degrees may increase the contact area between the stop bracket (814) and the left orbit during advancement of the blade (812) into the left orbit. It should be appreciate that, depending on the intended angle of insertion of the blade (812) relative to tissue, the angled stop brackets (814) may be used to facilitate formation of tissue openings in either orbits. For example, a cannula (700) with a stop bracket (814) at an angle (θ) greater than 90 degrees may be used to create an opening in the right orbit. In other instances, a cannula (700) with a stop bracket (814) at an angle (θ) less than 90 degrees may be used to create an opening in the left orbit.

Returning to FIG. 7, the delivery system (700) may further comprise a spacer (704). Generally, the spacer (704) may be sized to fit within and extend through the channel (806) of the cannula (702). The spacer (704) may be advanced through the channel (806) of the cannula to advance a distal end of the spacer (704) distally of the outlet (810) of the cannula (702). This may introduce the distal end of the spacer (704) into the tissue opening, which may dilate or otherwise expand the tissue opening (and in some instances a portion of the pocket). For example, the spacer (704) may have a dilating tip (710) at the distal end of the spacer (704), which may be configured to dilate the tissue opening and pocket formed by the blade (812) of the cannula (702). As shown in FIG. 7, the width and height of the dilating tip (706) may be tapered. In some of these variations, the tapering width of the dilating tip (706) may match the tapering width of the blade (812) of the cannula (702), although it should be appreciated that in some instances the surfaces of the dilating tip (706) may be rounded or otherwise dull to limit the ability of the dilating tip (706) to cut or sever tissue. As the dilating tip (706) is introduced through the tissue opening and into the pocket, the increasing height of the dilating tip (706) may dilate the tissue opening and the pocket.

In some variations, the spacer (704) may comprise a lip (712). In some variations, the lip (712) may catch or otherwise engage the inlet (808) of the cannula (702) during advancement of the spacer (704) to limit further advancement of the spacer (704). In some variations, the spacer (704) and cannula (702) may be sized such that when the lip (712) engages the inlet (808) of the cannula (702), the distal end of the dilating tip (706) is aligned with the distal end of the blade (812). In variations where the tapering width of the dilating tip (706) matches the tapering width of the blade (812), the edges of the dilating tip (706) may also be aligned with the edges of the blade (812) when the lip (712) engages the inlet (808) of the cannula (702).

The tongue (706) may be configured for advancement through the channel (806) of the cannula (702) while the spacer (704) is positioned to extend through the channel (806). Accordingly, the tongue (706), the spacer (704) and the channel (806) may each be sized such that the tongue (706) and spacer (704) may simultaneously fit inside the channel (806). As shown in FIG. 7, the tongue (706) may have a tapered tip (714) in which the width of the tongue (706) tapers. In some variations, the tapering width of the tongue (706) may match the tapering width of the dilating tip (706) of the spacer (704) and/or the tapering width of the blade (812) of the cannula (702), but need not. In some variations, the tongue (706) may further comprise a stop (716) configured to limit advancement of the tongue (706) through the channel (806) of the cannula. In some instances, the stop (716) may be a portion of the tongue having an increased width or height (such as a lip, or the like), which may catch on the inlet (808) of the channel (806) to prevent further advancement of the tongue (706) relative to the cannula (702). In some variations, the tongue (706) and cannula (702) may be sized such that when the stop (716) of the tongue (706) engages the inlet (808) of the channel (806) of the cannula (702), the tip of the tongue (706) may extend distally of the blade (812) of the cannula (702). In these variations, the tongue (706) may further separate tissue to extend the length of the pocket. Additionally, in variations where the tongue (706) comprises a tapered tip (714), the tapered width of the tapered tip (714) may facilitate separation of tissue. In other variations, the tongue (706) and cannula (702) may be sized such that when the stop (716) of the tongue (706) engages the inlet (808) of the cannula (702), the distal tip of the tongue (706) may be aligned with the distal tip of the blade (812) of the cannula (702). When the tongue (706) is positioned in the cannula (702), the tongue (706) may aid in insertion of the implant into tissue, as described in more detail below.

Figure 9:
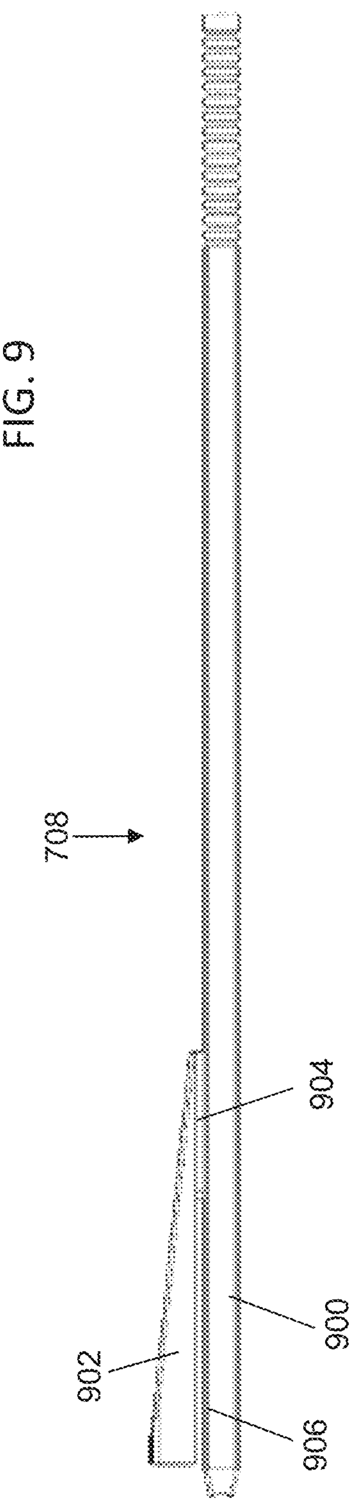
FIGS. 9 and 10 show side views of variations of plungers suitable for use with the delivery system of FIG. 7.

As mentioned above, the delivery system (700) may also comprise a plunger (708) which may be advanced into the channel (806) of the cannula (702) to advance an implant through the channel (806). FIG. 9 shows a side view of one variation of a plunger (708) suitable for use with the delivery system of FIG. 7. As shown there, the plunger (708) may comprise a plunger portion (900) sized and configured to be inserted into the channel (806) of the cannula (702) through the inlet (808). The plunger (708) may further comprise a stopper portion (902) connected to a distal portion of the plunger portion (900) via a transition region (904). The stopper portion (902) may be a portion of the plunger (708) configured to remain outside of the channel (806) when the plunger portion (900) is inserted into the channel (806). For example, in the variation of the cannula (702) shown in FIGS. 8A-8C, the top wall (800) may include a slot (824) extending at least partially along the channel (806) (which in some variations may extend from the inlet (808)). In some variations, the slot (824) may extend along the entire length of the channel (806). When the plunger portion (900) is inserted into the channel (806), the transition region (904) may extend through the slot (824) to position the stopper portion (902) outside of the channel (806). In some instances, the plunger portion (900) and stopper portion (902) may each be wider than the slot (824) of the top wall (800), such that when the transition region (904) is positioned at least partially into the slot (824), the plunger portion (900) may be prevented from exiting the channel (806) through the slot (824) of the top wall (800) and the stopper portion (902) may be prevented from entering the channel (806) through the slot (824) of the top wall (800). Similarly, the transition region (904) may be narrower than the slot (824) to allow the transition region (904) to enter the slot (824) during advancement of the plunger (708).

In some variations, a distal portion of the stopper portion (902) may extend distally of the distal end of the transition region (904) to define a space (906) between the distal portion of the stopper portion (902) and the plunger portion (900). This space (906) may allow the distal end of the stopper portion (902) to be advanced distally of the distal end of the slot (824) of the top wall (800). Specifically, the distal end of the transition region (904) may prevent further advancement of the plunger (708) relative to the cannula (702) when the distal end of the transition region (904) reaches and engages the distal end of the slot (824). In variations where the distal end of the stopper portion (902) is flush with the distal end of the transition region (904), the distal end of the stopper portion (902) may be aligned with the distal end of the slot (824) when the distal end of the transition region (904) reaches the distal end of the slot (824). In variations where the distal end of stopper portion (902) extends distally of the distal end of the transition region (904), the top wall (800) may be received in the space (906) between the stopper portion (902) and the plunger portion (900) until the distal end of the transition region (904) reaches the distal end of the slot (824) to prevent further advancement of the plunger (708) relative to the cannula (702). At this point, the distal end of the stopper portion (902) may extend distally of the distal end of the slot (824) of the top wall (800). Additionally or alternatively, the plunger (708) may be sized and configured such that a distal end of the plunger portion (900) may extend distally of the outlet (810) of the channel (806) when the transition region (904) reaches the distal end of the slot (824). Additionally, in variations where the cannula (702) comprises a stop bracket (814) having an aperture (820) extending therethrough, a distal portion of the stopper portion (902) may be sized to fit through the aperture (820) of the stop bracket (812), which may allow the stopper portion (902) to be advanced through the aperture (820) during advancement of the plunger (708) relative to the cannula (702).

Figure 10:
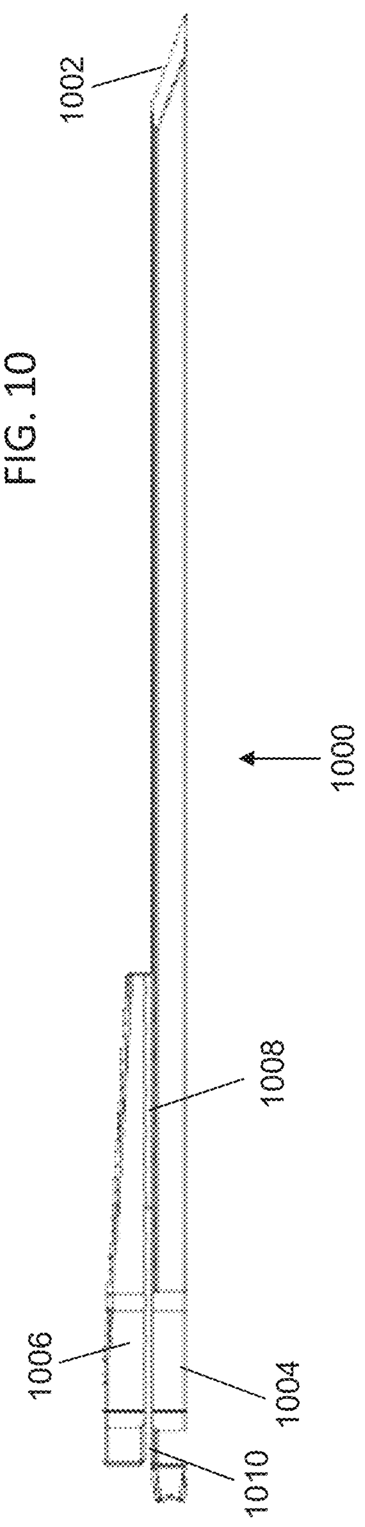

While the variation of the delivery system (700) depicted in FIG. 7 is shown as having a plunger (708) that is separate from the spacer (704), it should be appreciated that in other variations the delivery system (700) may include a single member that may act as both a plunger and a spacer. For example, FIG. 10 shows one such variation of a plunger (1000) that may be used with the delivery system (700). As shown there, the plunger (1000) may comprise a first end having a dilating tip (1002). The dilating tip (1002) may be configured in any manner as described above with respect to the dilating tip (710) of the spacer (702) of FIG. 7. In these variations, the first end of the plunger (1000) may be inserted into the channel (806) of a cannula (702) to act as a spacer (704), as will be discussed in more detail below.

The plunger (1000) may further comprise a second end may be configured to include one or more elements of the plunger (708) described above with respect to FIG. 9. Specifically, the second end of the plunger (1000) may comprise a plunger portion (1004) and a stopper portion (1006) connected to the plunger portion (1004) by a transition region (1008). The plunger portion (1004) of the second end of the plunger (1000) may be inserted into the channel (806) of the cannula (700), and the stopper portion (1006) may be configured to remain outside of the channel (806) when the plunger portion (1004) of the second end is inserted into the channel (806). In some variations, such as shown in FIG. 10, a distal end of the stopper portion (1006) may extend distally of the transition region (1008) to define a space (1010) between the stopper portion (1006) and the plunger portion (1004) of second end of the plunger (1000). In these variations, a portion of the top wall (800) may be received in the space (1010) during advancement of the second end of the plunger (1000) into the channel (806) of the cannula (702). Additionally, a proximal end of the transition region (1008) and/or the stopper portion (1006) may act as a stop to limit advancement of the dilating tip (1002) of the first end of the plunger (1000) into the cannula (700).

Figure 11A:
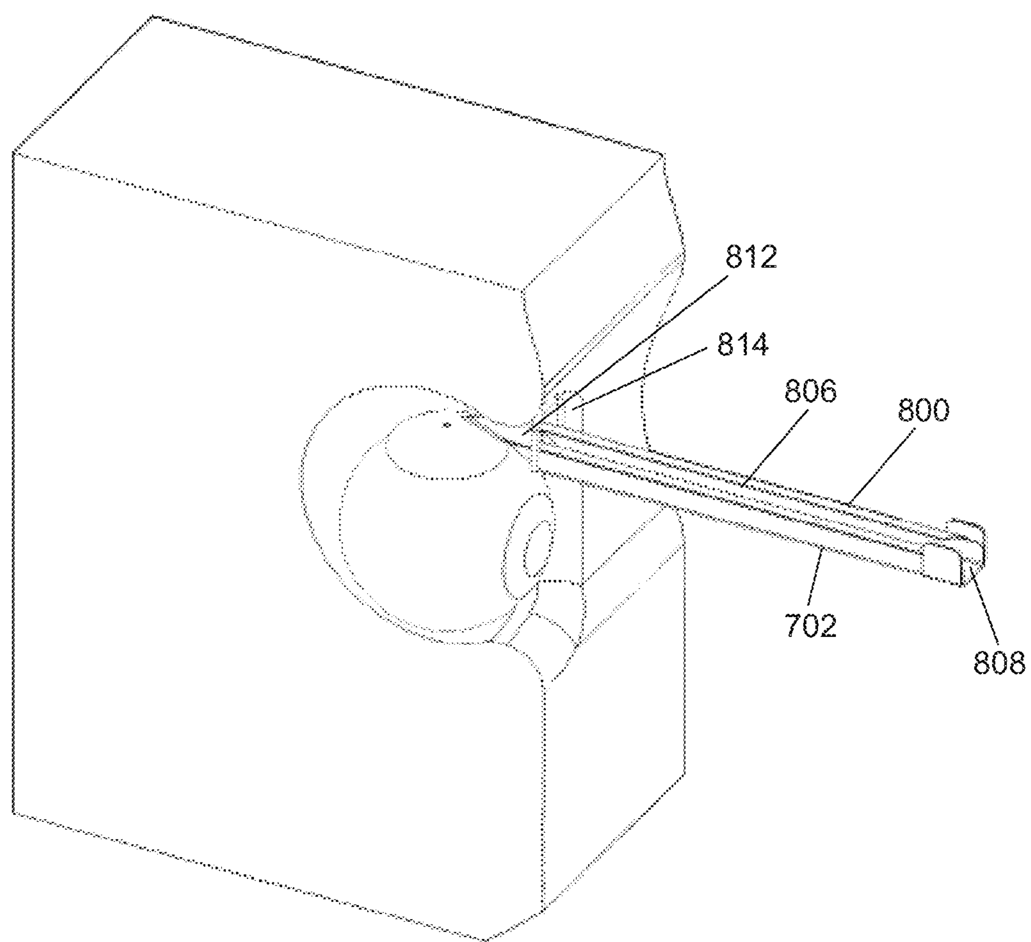
FIGS. 11A-11I depict an illustrative method by which the delivery system of FIG. 7 may be used to deliver an implant.

FIGS. 11A-11I depict an illustrative method by which the delivery system (700) described above with respect to FIGS. 7-10 may be used to deliver an implant (1100) to the orbit of a patient. The cannula (702) may be advanced toward the orbit of a patient as illustrated in FIG. 11A, and the blade (812) may be advanced to pierce tissue of the patient to form an opening therein. In some variations, the piercing tip (816) of the blade (812) may puncture the conjunctiva to form a tissue opening in the conjunctiva. In some of these variations, the method may comprise retracting an eyelid prior to piercing the conjunctiva. In other variations, the piercing tip (816) of the blade (812) may puncture the eyelid to form a tissue opening in the eyelid. The blade (812) may be further advanced relative to the tissue opening to separate tissue beyond the opening to form a pocket in the tissue. In some variations, the blade (812) may be advanced between the periosteum and the orbital bone to form a pocket therebetween. In other instances, the blade (812) may be advanced between the periosteum and another tissue, such as the lacrimal gland, to form a pocket therebetween. In variations where the width of the blade (812) tapers, advancement of the blade (812) through the tissue opening may dilate the tissue opening. Additionally, in variations where the cannula (700) comprises a stop bracket (814), the cannula (700) may be advanced to advance the blade (812) into tissue until the stop bracket (814) contacts tissue (e.g., tissue overlying the orbital fossa such as shown in FIG. 11A), which may prevent or otherwise limit further advancement of the cannula relative to tissue.

Figure 11B:
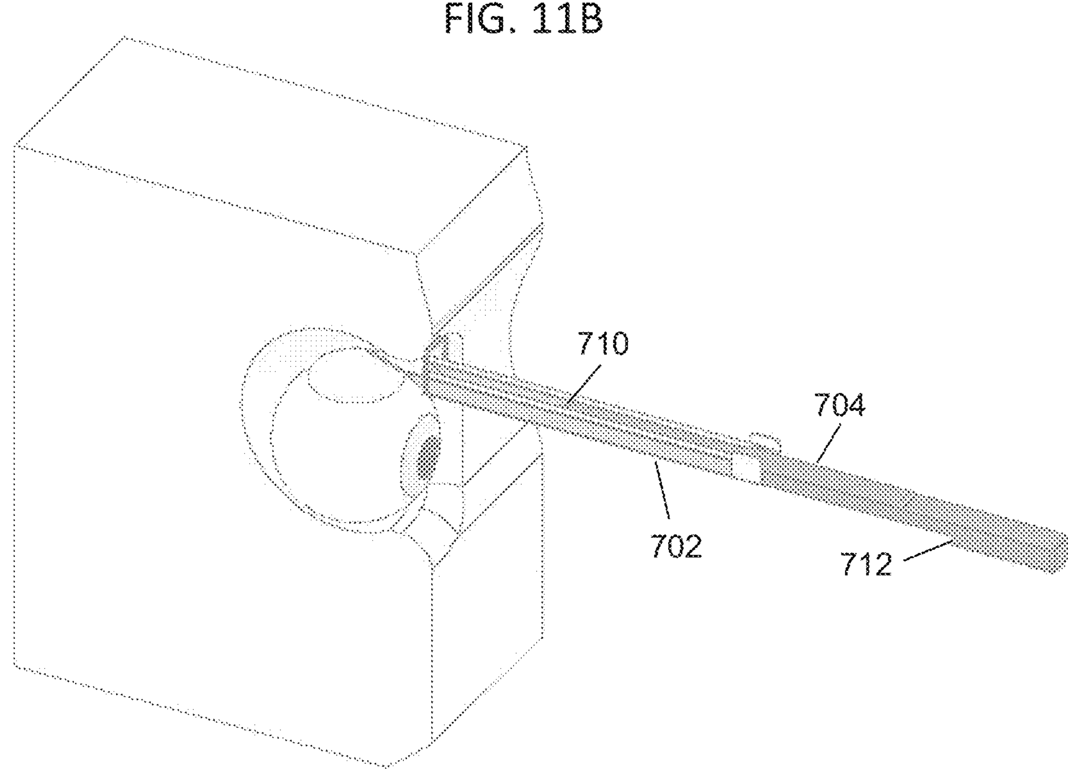
Figure 11C:
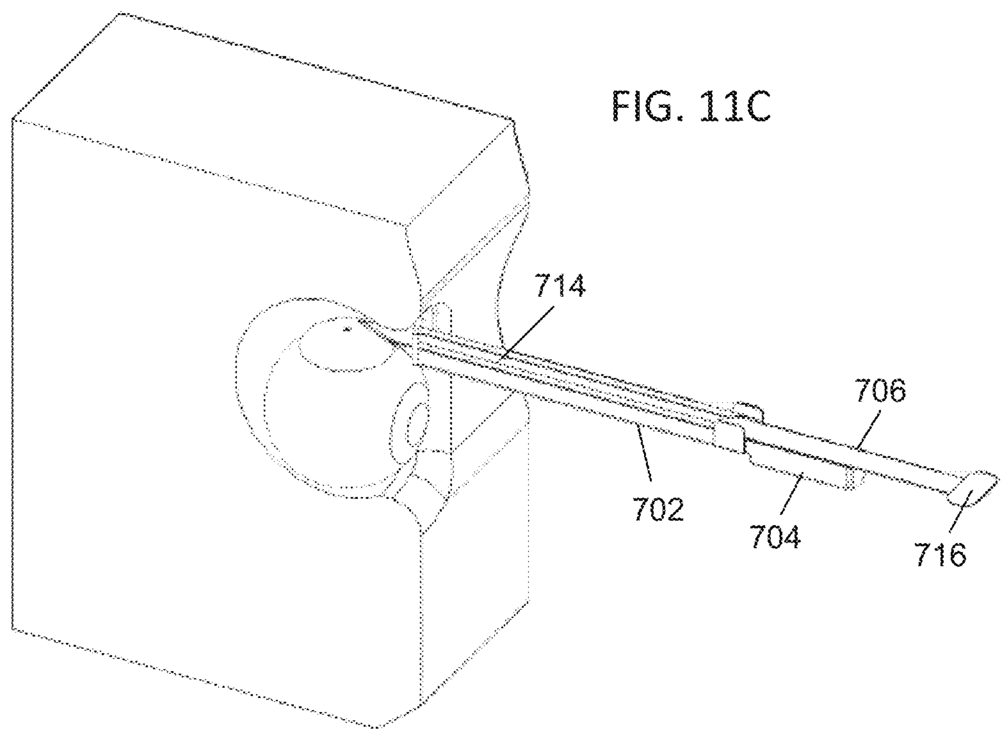

With the blade (812) positioned to extend through the tissue opening, the spacer (704) may be introduce into and advanced through the channel (806) of the cannula (700), as illustrated in FIG. 11B, and may be further advanced to position a dilating tip distally of the outlet (810) of the channel (806). This advancement may advance the dilating tip (710) of the spacer (704) through the tissue opening and into the pocket, as illustrated in FIG. 11C. As the dilating tip (710) passes through the tissue opening and into the pocket, the dilating tip (710) may dilate the tissue opening and the pocket. While the dilating tip (710) of the spacer (704) is shown in FIGS. 11B and 11C as expanding the tissue opening and the pocket, it should be appreciated that in some variations, the dilating tip (1002) of the first end of plunger (1000) described above with respect to FIG. 10 may be instead be advanced into the cannula (700) as described above.

Generally, the dilating tip (710) may be introduced into the channel (806) through an inlet (808) of the channel, advanced through the channel (806), and out of the outlet (810) of the channel (806). In some variations, the dilating tip (710) may be advanced into the pocket until the distal end of the dilating tip (710) is aligned with a distal tip of the blade (812). In some instances, the dilating tip of the spacer (or plunger) may be advanced through the cannula until a portion of the spacer (or plunger) engages the inlet (808) of the channel (806) of the cannula (702). For example, in variations where the spacer (704) comprises a lip (712), the spacer (704) may be advanced through the channel (806) of the cannula (700) until the lip (712) catches on the inlet (808) of the channel (806) (e.g., the engagement between the lip (712) and the inlet (808) may prevent further advancement of the spacer (704) relative to the cannula (700)), such as shown in FIG. 11C. In variations where a dilating tip (1002) of a plunger (1000) is advanced through the cannula, the plunger (1000) may be advanced through the channel (806) of the cannula (700) until a portion of the stopper portion (1006) and/or transition region (1008) of the second end of the plunger (1000) catches on the inlet (808) of the channel (806) (e.g., the engagement between the stopper portion (1006) and/or transition region (1008) and the inlet (808) may prevent further advancement of the plunger (1000) relative to the cannula (700)).

Figure 11D:
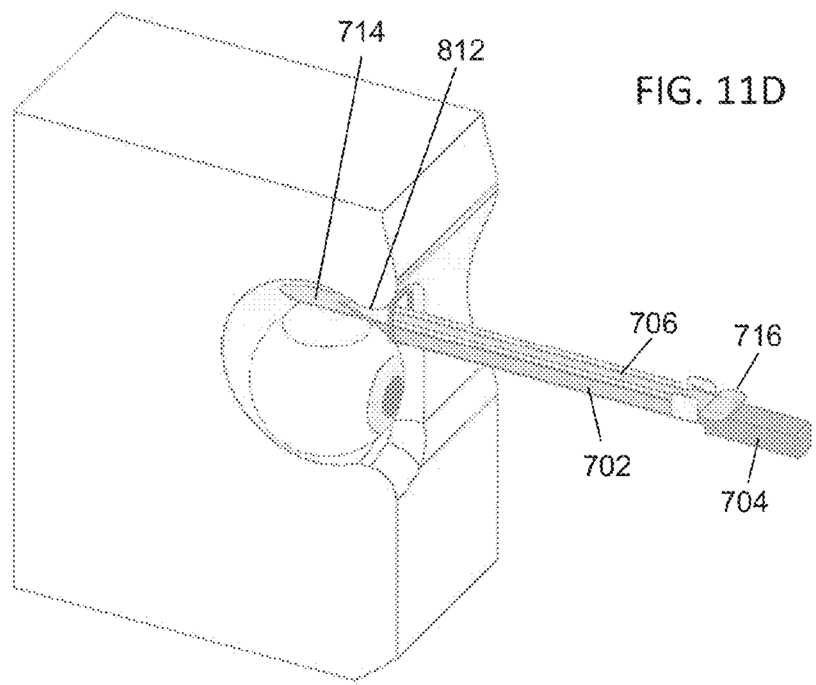

With the blade (816) of the cannula (700) and the dilating tip of either a spacer or a plunger positioned to extend through the tissue opening, the tongue (706) may be advanced through the channel (806) of the cannula (700), as shown in FIG. 11C, and may be advanced out of the outlet (808) of the channel (806) of the cannula (700) to advance a distal tip of the tongue (706) through the tissue opening and into the pocket, as shown in FIG. 11D. In some of these variations, the tip of the tongue may be advanced distally of the tip of the blade and the dilating tip of the spacer (or plunger), which may further separate tissue to extend the length of the pocket. In some instances, the tongue (706) may be advanced through the cannula (700) between the spacer (or plunger) and the top wall (800) of the cannula. In variations where the tongue (706) comprises a stop (716), the tongue may be advanced until the stop (716) engages the inlet (808) of the channel (806) of the cannula (702), which in turn may control how far the tip of the tongue (706) is advanced into the orbit.

Figure 11E:
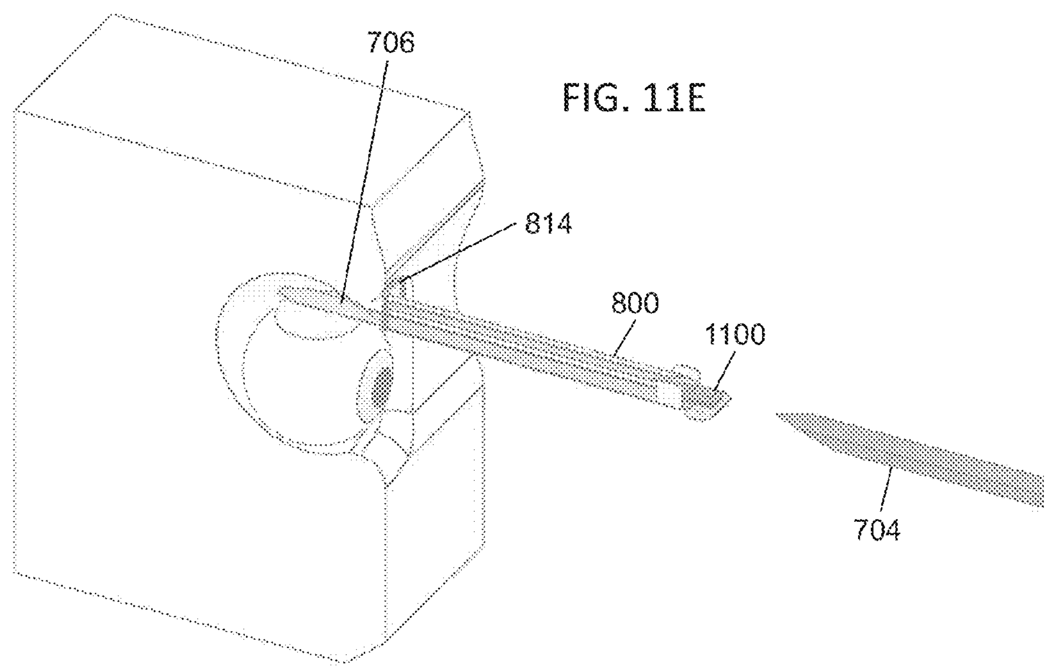
Figure 11F:
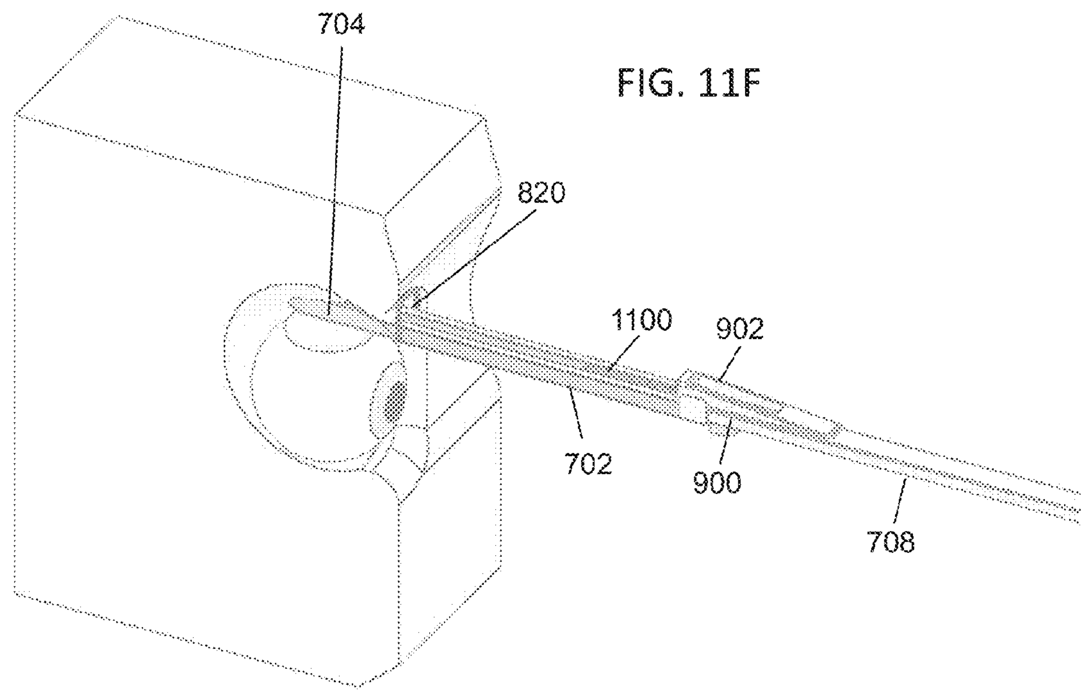

The spacer (or plunger) may be removed from the tissue opening and channel (806) (e.g., by proximally withdrawing the spacer or plunger relative to the cannula (702)), and the implant (1100) may be inserted into the channel (806) (e.g., by inserting the implant (1100) into the inlet (808) of the channel (806)), such as shown in FIG. 11E. In some instances, the implant (1100) may be positioned between the tongue (706) and the top wall (800) of the cannula (700). With the implant positioned in the channel (806), a plunger portion (900) of the plunger (708) may be advanced into the channel (806), such as shown in FIG. 11F. As shown there, the plunger portion (900) may be positioned between the tongue (706) and the top wall (800), and the stopper portion (902) may be positioned outside of the channel (806) (e.g., the transition region (904) may extend through the slot (824) in the top wall (800) of the cannula). As the plunger (708) is advanced into the channel (806), a portion of the plunger (708) (e.g. the plunger portion (900)) may contact the implant (1100) and push the implant (1100) along the channel (806).

Figure 11G:
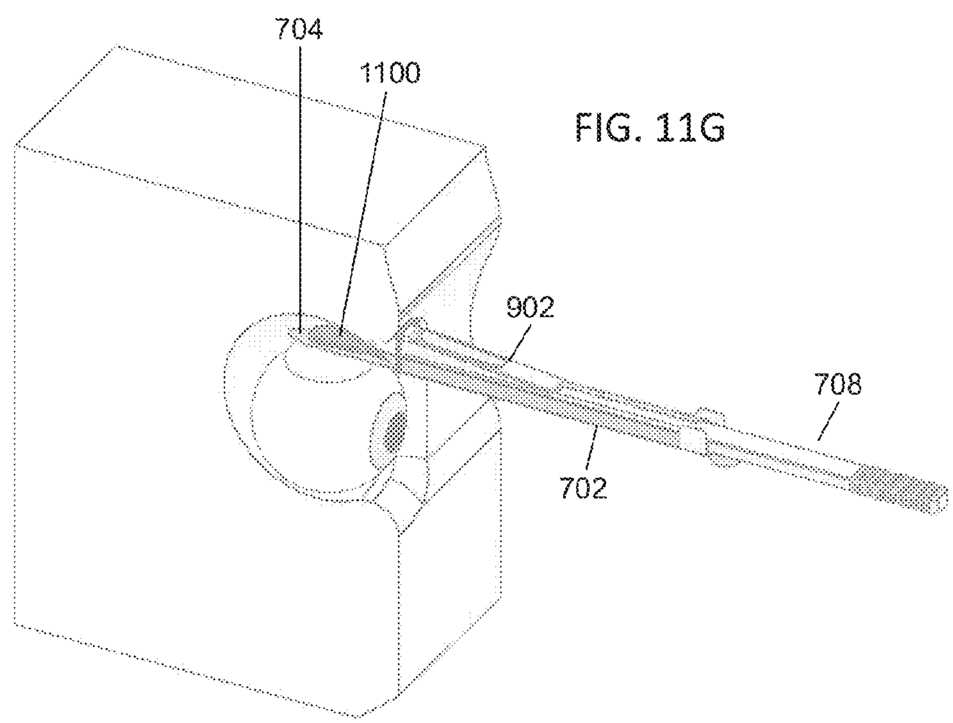

In some variations, the plunger (708) may advance the implant (1100) until the stopper portion (902) contacts tissue (e.g., tissue overlying the orbital fossa), such as shown in FIG. 11G. In variations where the cannula (702) has a stop bracket (814) defining an aperture (820) extending therethrough, the stopper portion (902) may extend at least partially through the aperture (820) to contact tissue. In some variations, the plunger (708) may be configured such that when the stopper portion (902) of the plunger (708) engages tissue (e.g., to prevent further advancement of the plunger), the plunger portion (900) has advanced the implant (1100) distally of the outlet (810) of the channel (806) of the cannula (702), through the tissue opening, and into the pocket, such as depicted in FIG. 11G. In these variations, the blade (816) and the tongue (706) may guide advancement of the implant (1100) after the implant (1100) has been advanced out of the outlet (810) of the channel (806).

Figure 11H:
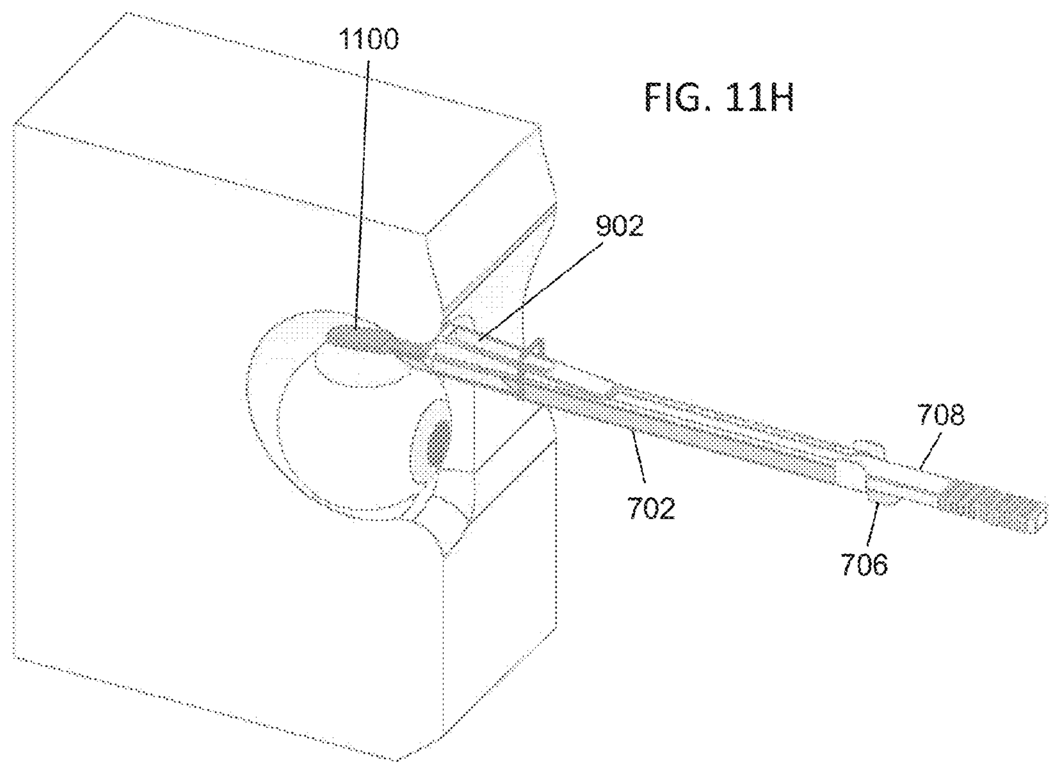
Figure 11I:
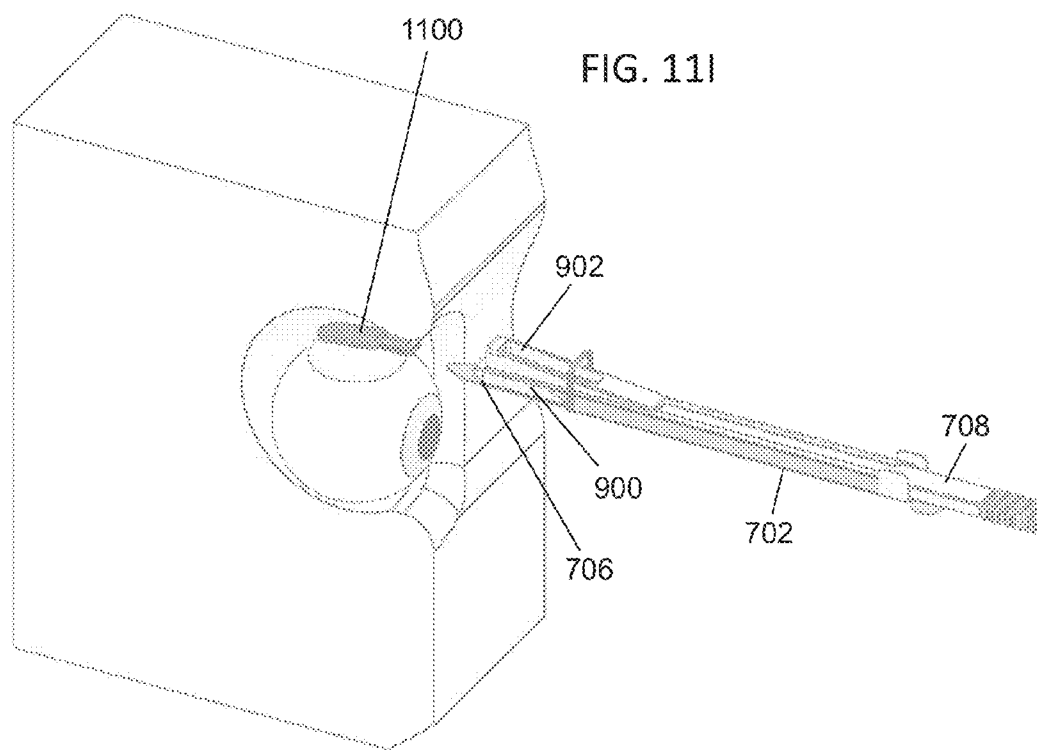

A user may hold the stopper portion (902) against the patient, and may withdraw the cannula (702) and the tongue (704) relative to the plunger (708) to withdraw the blade (816) and the distal tip of the tongue (704) at least partially from the tissue opening and pocket, such as shown in FIG. 11H. As the cannula (702) and the tongue (706) are withdrawn relative to plunger (708), the plunger portion (900) of the plunger (708) may contact and hold the implant (1100) in place, and thus may prevent the implant (1100) from being withdrawn with the cannula (702) and the tongue (706). In variations where the stopper portion (902) of the plunger (708) extends distally of the transition region (904), the cannula (702) may be withdrawn relative to the plunger (708) until the distal end of the slot (824) engages the transition region (904), at which point further retraction of the cannula (702) relative to the patient may also pull the plunger (708) proximally relative to the patient, such as shown in FIG. 11I, which may disengage the entire delivery system (700) from the patient. It should be appreciated that while the plunger (708) described above with respect to FIG.

9 is depicted in FIGS. 11F-11I as advancing implant (1100), the second end of the plunger (1000) described above with respect to FIG. 10 may be used to advance the implant (1100) in the manner discussed immediately above. Once the delivery system (700) has been removed from the patient, the tissue opening may be closed in any suitable manner such as those discussed above.

In some instances, one or more components of the delivery systems (700) described above with respect FIGS. 7-10 may be integrated into single device. For example, FIGS. 12A-12I depict a variation a delivery device (1200) as described here. As shown there, the delivery device (1200) may comprise a cannula (1202), a tongue (1204), and a plunger (1206). The cannula (1202) may define a channel (1208) extending between an inlet (1210) and an outlet (1212), and the tongue (1204) and plunger (1206) may be slidably connected to the cannula (1202) to extend at least partially through the channel (1208). In some variations, the outlet (1212) may be angled, such that the height of the channel (1208) increases from a distal end of the outlet (1212) to a proximal end of the outlet (1212). In these variations, the walls of the cannula (1202) defining the outlet (1212) may dilate a tissue opening as the cannula (1202) is advanced into a tissue opening.

Figure 12A:
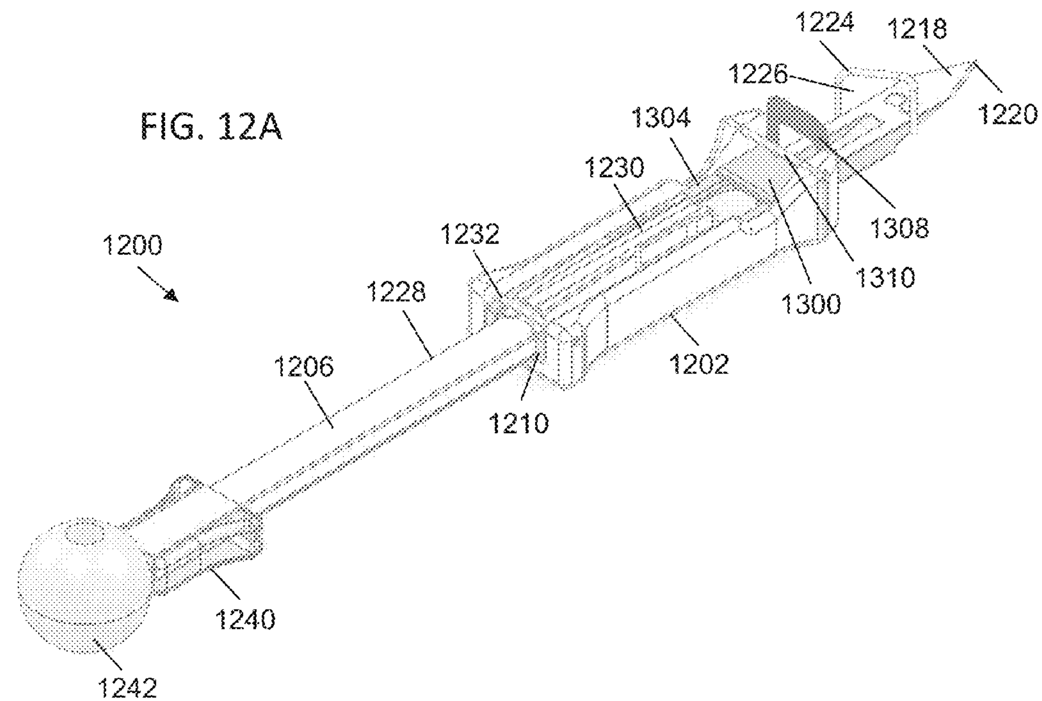
FIGS. 12A-12D depict perspective, side, top, and front views, respectively of a variation of a delivery device as described here.
Figure 12B:
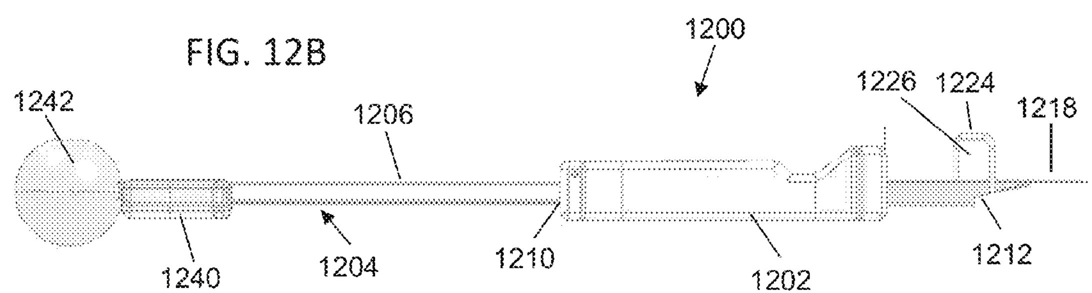
Figure 12C:
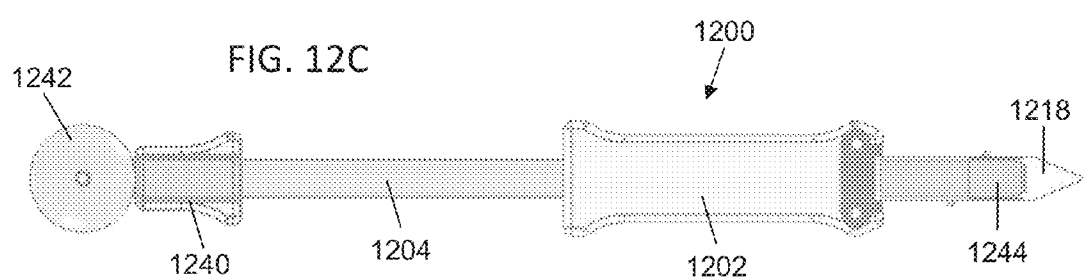
Figure 12D:
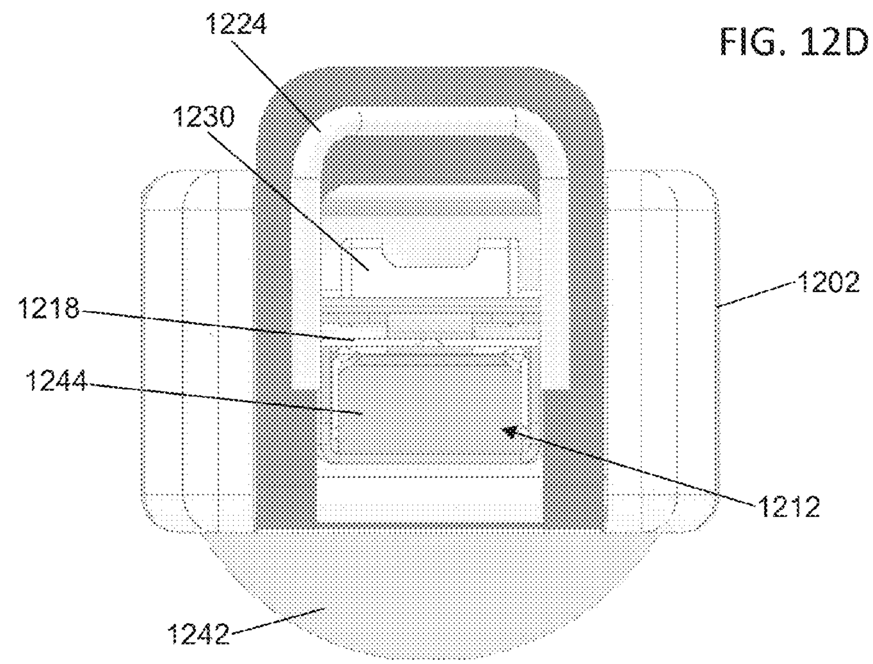
Figure 12E:
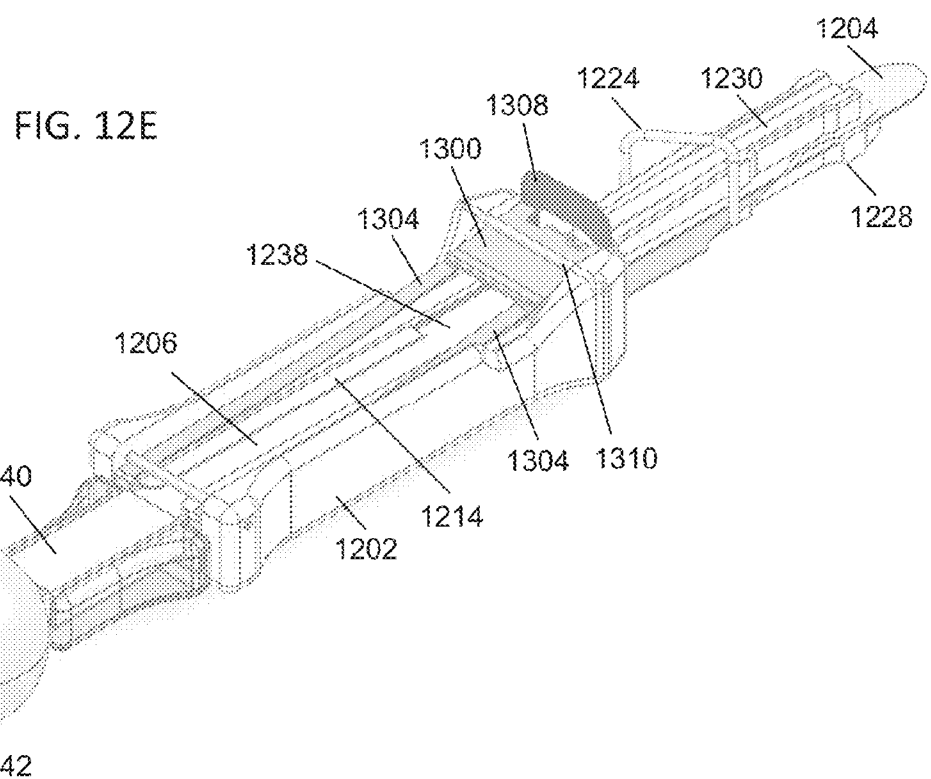
FIGS. 12E and 12F depict perspective views and FIGS. 12G and 12H depict side views of the delivery device of FIGS. 12A-12D.
Figure 12F:
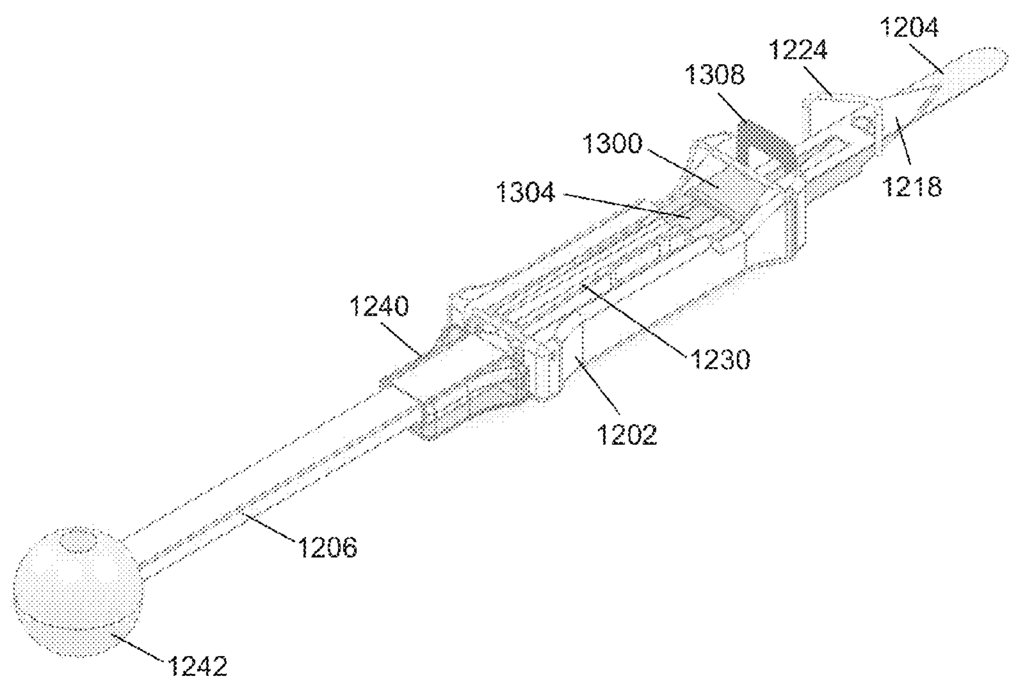
Figure 12G:
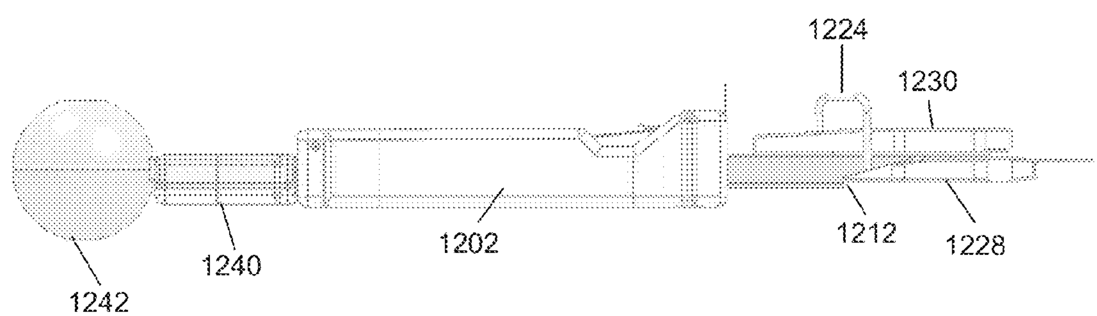
Figure 12H:
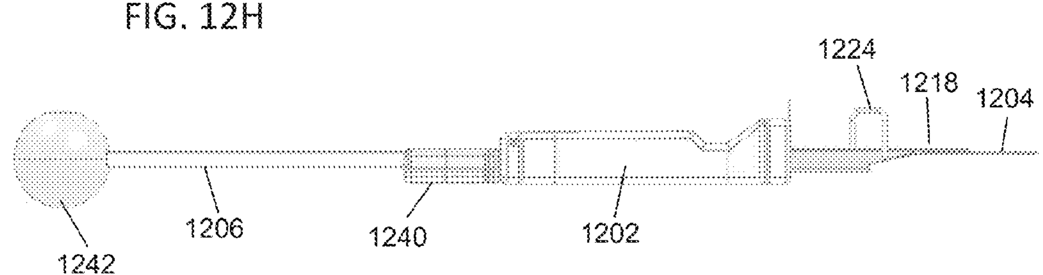
Figure 12I:
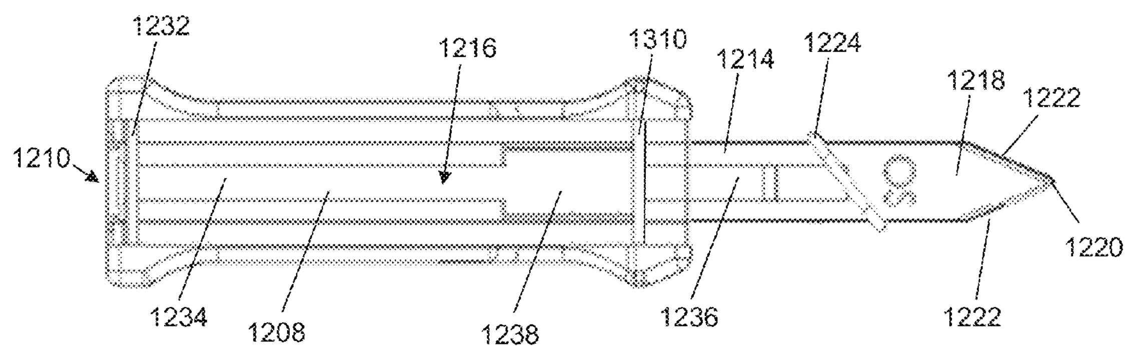
FIG. 12I depicts a top view of the cannula of the delivery device of FIGS. 12A-12H.
Figure 13A:
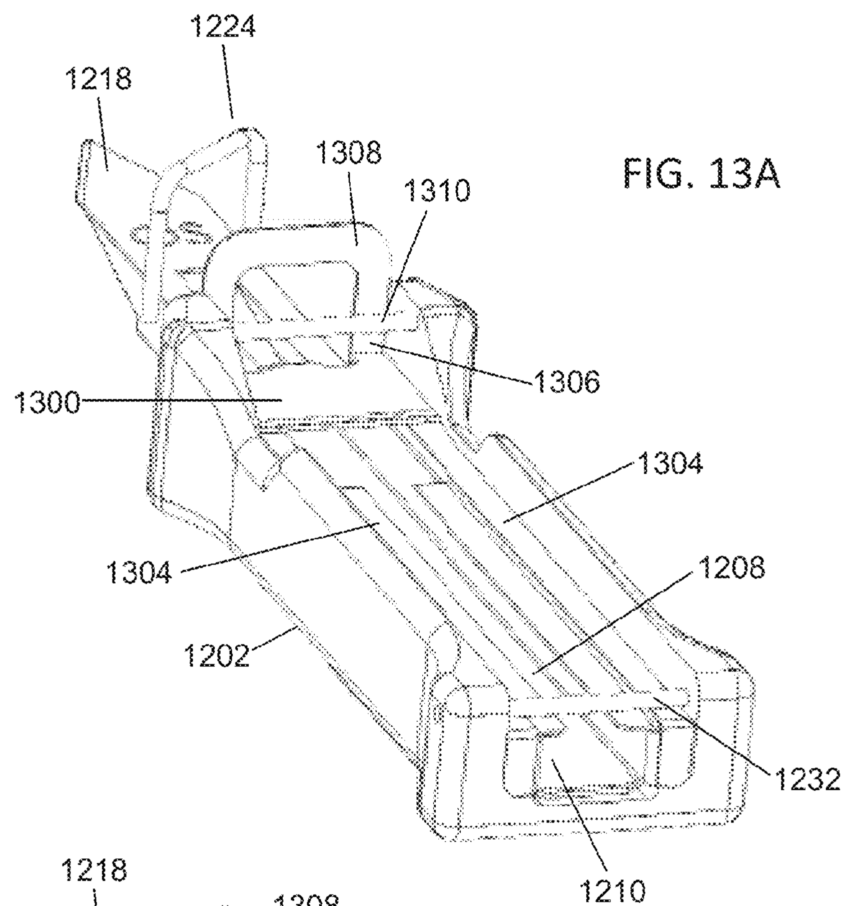
FIGS. 13A and 13B depict rear perspective views and FIGS. 13C and 13D depict front perspective views of a variation the cannula of the delivery device of FIGS. 12A-12I having a bumper plate.
Figure 13B:
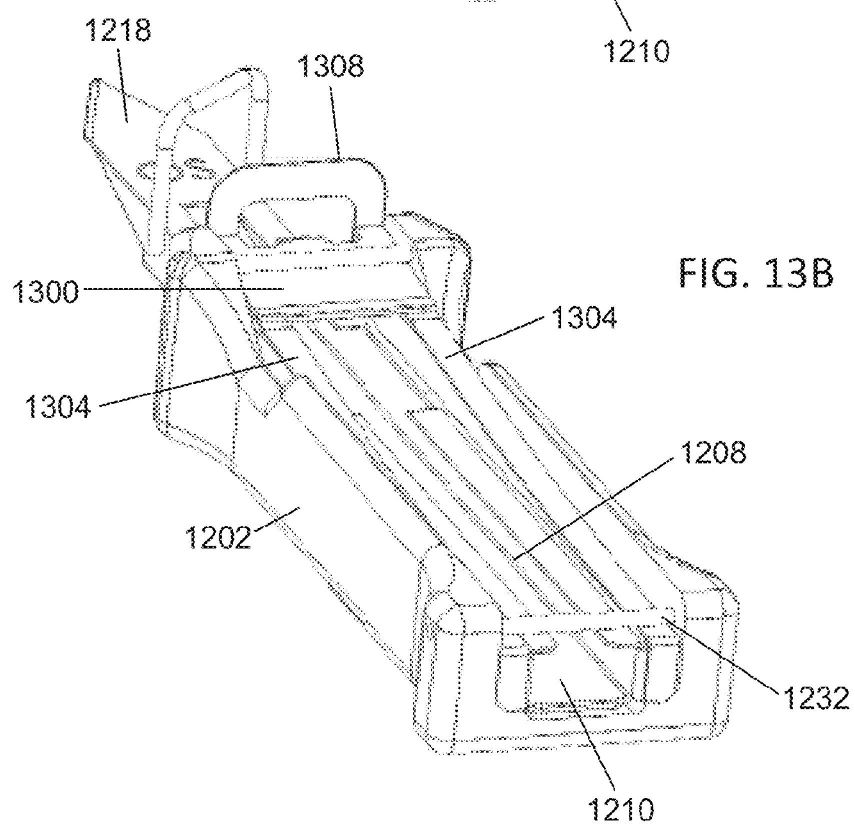
Figure 13C:
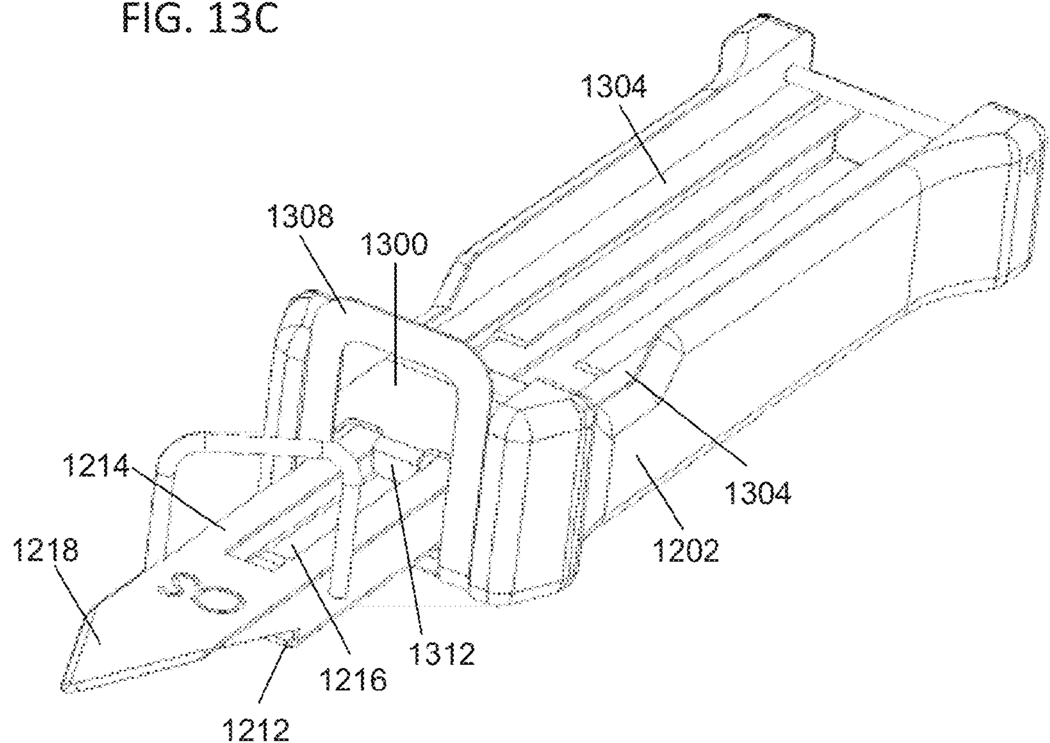
Figure 13D:
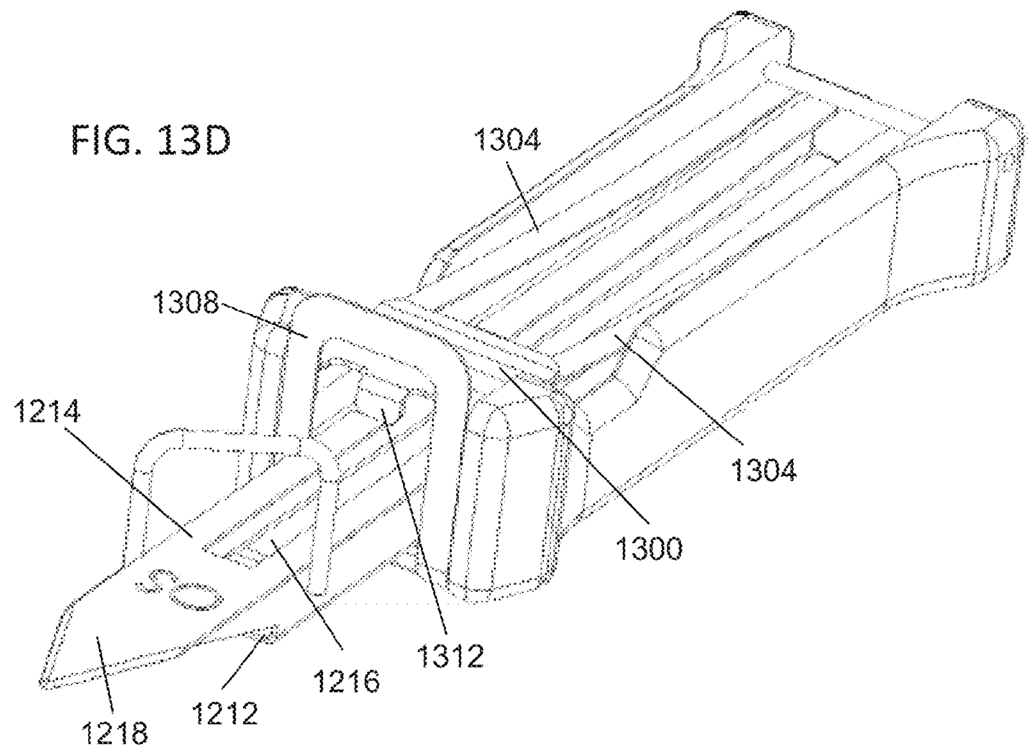

FIG. 12I depicts a top view of the cannula (1202) (the remaining components of the delivery device (1200) are not illustrated in this figure). As shown there, the cannula (1202) may further comprise a top wall (1214) having a slot (1216) extending at least partially along the channel (1208). In some of these variations, the slot (1216) may extend at least partially along the channel (1208) from an inlet (1210) of the channel (1208). A portion of the plunger (1206) may extend through the slot (1216) of the top wall (1214), as will be discussed in more detail below. In some variations, such as shown in FIG. 12I, the slot (1216) may comprise a proximal segment (1234), a distal segment (1236), and an intermediate segment (1238) between the proximal segment (1234) and the distal segment (1236). The width of the intermediate segment (1238) may be wider than the widths of the proximal segment (1234) and the distal segment (1236). In some instances, an implant may be inserted into the channel (1208) of the cannula (1202) via the intermediate segment (1238). In these variations, the width of the intermediate segment (1238) may be greater than a width of the implant, which may allow the implant to enter the channel (1208) through the intermediate segment (1238). In some of these variations, the width of the distal segment (1236) of the slot (1216) may be less than the width of the implant, which may prevent the implant from exiting the channel (1208) through the distal segment (1236) as the implant is advanced through the channel (1208) of the cannula (1202).

The cannula (1202) may further comprise a blade (1218), which may be configured in any suitable manner such as described above with respect to the blade (812) of the cannula (702) described above with respect to FIGS. 8A-8C above. For example, the blade (1218) may include a piercing tip (1220), which may puncture tissue to form a tissue opening. In some variations, the width of the blade (1218) may be tapered such that the width of the blade (1218) increases proximally from the piercing tip (1220). In these instances, advancement of the blade (1218) into the tissue opening may dilate the tissue opening. The blade (1218) may optionally further comprise one or more cutting edges (1222), which may configured to cut tissue as the blade (1218) is advanced into the tissue opening (which may facilitate expansion of the tissue opening). Additionally, in some variations the cannula (1202) may further comprise a stop bracket (1224), which may be configured as any of the variations of the stop bracket (814) described above with respect to FIGS. 8A-8C. Generally, the stop bracket (814) may extend away from the top wall (1214) by a height which may allow the stop bracket (814) to engage the tissue (e.g., tissue overlying the orbital fossa) during advancement of the blade (1218) into the tissue opening. In some variations, the stop bracket (1224) may comprise an aperture (1226) extending through the stop bracket (1224). A portion of the plunger (1206) may extend through the aperture (1226) during use of the delivery device (1200), as will be discussed in more detail below. Additionally, the stop bracket (814) may be positioned at any angle relative the longitudinal axis of the cannula (1202) as discussed above with respect to the stop bracket (814) of FIGS. 8A-8C.

As mentioned above, the plunger (1206) may be slidably connected to the cannula (1202). In some variations, the plunger (1206) may comprise a plunger portion (1228) and a stopper portion (1230), wherein the plunger portion (1228) is positioned at least partially in the channel (1208) and the stopper portion (1230) is positioned outside of the channel (1208). The stopper portion (1230) and plunger portion (1228) may be configured in any manner as described above with respect to the plunger portion (900) and stopper portion (902) described above with respect to the plunger (708) of FIG. 9. For example, in some variations, the stopper portion (1230) may be connected to the plunger portion (1228) by a transition region, which may extend through the slot (1216) of the top wall (1214). In some of these variations, the distal end of the stopper portion (1230) may extend distally of the distal end of the transition region to define a space between the distal portion of the stopper portion and the plunger portion.

In some instances, the stopper portion (1230) and/or the transition region may control the range of motion of the plunger (1206) relative to the cannula (1202). For example, in some variations, a proximal end of the stopper portion (1230) and/or transition region may engage a portion of the cannula (1202) during withdrawal of the plunger (1206) to prevent further withdrawal of the plunger (1206) (which may prevent the plunger (1206) from being removed from the channel (1208) of the cannula (1202)). For example, the cannula (1202) may comprise a projection such as a bar (1232) which may be connected to the cannula (1202). The bar (1232) may be positioned relative to the plunger (1206) such that a proximal end of the stopper portion (1230) of the plunger (1206) contacts the bar (1232) when the plunger (1206) is retracted relative to the cannula (1202), such as shown in FIGS. 12A-12D. The contact between the plunger (1206) and the bar (1232) may prevent further retraction of the plunger (1206) relative to the cannula (1202). Similarly, a portion of the plunger (1206) may limit the distal advancement of the plunger (1206) relative to the cannula (1202). In some variations, the plunger (1206) may be advanced until the transition region contacts a distal end of the slot (1216), which may prevent further advancement of the plunger (1206) relative to the cannula (1202). In variations where a distal end of the stopper portion (1230) extends distally of the distal end of a transition region, the plunger (1206) may be advanced relative to the cannula (1202) until a distal end of the transition region contacts a distal end of the slot (1216), such as shown in FIGS. 12E and 12G. In these variations, the distal end of the stopper portion (1230) may extend distally of the distal end of the slot (1216), and in some instances may extend at least partially through the aperture (1226) of the stop bracket (1224). Additionally or alternatively, the distal end of the plunger portion (1228)

may extend distally of the distal end of the slot (1216) when the distal end of the transition region contacts the distal end of the slot (1216). In some of these variations, the distal end of the plunger portion (1228) may extend distally of the outlet (1212) of the channel (1208) when the distal end of the transition region contacts the distal end of the slot (1216).

It should be also be appreciated that in some instances the delivery device (1200) may be temporarily configured to prevent advancement of the plunger (1206) between the retracted position shown in FIGS. 12A-12D and the extended position shown in FIGS. 12E and 12G. In some variations, the delivery device (1200) may comprise an intermediate stop, which may temporarily limit advancement of the plunger (1206) between the retracted and extended positions. For example, FIGS. 13A-13D depict a variation of the cannula (1202) of the delivery device (1200) of FIGS. 12A-12I with the plunger (1206) and tongue (1204) removed. As shown there, the cannula (1202) may comprise a bumper plate (1300). The bumper plate (1300) may be moveable between a lowered position (as shown in rear and front perspective views in FIGS. 13A and 13C) and a raised position (as shown in rear and front perspective views in FIGS. 13B and 13D). When the bumper plate (1300) is in the lowered position, the bumper plate (1300) may block advancement of the plunger (1206) to the extended position shown in FIGS. 12E and 12G. For example, the plunger (1206) may be advanced with the bumper plate (1300) in the lower position until the stopper portion (1230) reaches and contacts the bumper plate (1300). The engagement between the stopper portion (1230) and the bumper plate (1300) may temporarily prevent further advancement of the plunger (1206) relative to the cannula (1202). Conversely, when the bumper plate (1300) is in the raised position, the stopper portion (1230) may pass under the bumper plate (1300) and may allow the plunger (1206) to be advanced to the extended position.

The bumper plate (1300) may be moved between the lowered and raised positions in any suitable manner. For example, in some variations the delivery device (1200) may comprise one or more spring elements (1304) connecting the bumper plate (1300) to the cannula (1202). While shown in FIGS. 13A-13D as being a beam springs, the spring elements (1304) may be any suitable spring (e.g., a compression spring, a torsion spring, or the like). Additionally, while shown in FIGS. 13A-13D as having two spring elements (1304), the bumper plate (1300) may comprise any suitable number of spring elements (1304) (e.g., one, two, or three or more). In some variations, the one or more spring elements (1304) may be biased toward the lowered position. In these variations, a control (such as a switch, lever, or the like) may be actuated to lift the bumper plate (1300) to overcome the bias of the one or more spring elements (1304) and raise the bumper plate (1300) to the raised position. In other variations, such as that shown in FIGS. 13A-13D, the one or more spring elements (1304) may bias the bumper toward the raised position. In these variations, a control element may temporarily hold the bumper plate (1300) in the lowered position.

For example, in the variation of the cannula (1202) shown in FIGS. 13A-13D, the cannula (1202) may comprise a release bracket (1308), which may be position and arranged to temporarily hold the bumper plate (1300) in the lowered position. For example, the release bracket (1304) may comprise one or more projections (1306) or lips, or may otherwise be configured to engage the release bracket (1308) when the bumper plate (1300) is in the lowered position to hold bumper plate (1300) in the lowered position. To move the bumper plate (1300) to the raised position, a user may deflect or otherwise move the release bracket (1308) away from the bumper plate (1300), which may temporarily disengage the release bracket (1308) from the bumper plate (1300). When the release bracket (1308) is disengaged from the bumper plate (1300), the one or more spring elements (1304) may lift the bumper plate (1300) to the raised position. In some variations, the cannula (1202) may optionally further comprise a structure (such as a stop bar (1310)) positioned to contact the bumper plate (1300) and/or the one or more spring elements (1304) to limit the upward motion of the bumper plate (1300), which in turn may control the raised position of the bumper plate (1300).

In some variations, the bumper plate (1300) may be further configured to temporarily limit advancement of the implant relative to the bumper plate (1300). For example, in the variation of the cannula (1202) shown in FIGS. 13A-13D, the bumper plate (1300) may comprise an extension (1312) positioned and arranged to extend into the channel (1208) when the bumper plate (1300) is in the lowered position. For example, extension (1312) of the bumper plate (1300) may extend through the intermediate segment (1238) and/or the distal segment (1236) of the slot (1216) when the bumper plate (1300) is in the lowered position. When an implant is inserted into the channel (1208) (i.e., through the intermediate segment (1238)), the implant may be advanced until it contacts the extension (1312). The extension (1312) may be sized such that the implant may be prevented from being advanced distally of the extension (1312) when the extension (1312) is positioned in the channel (1208). When the bumper plate (1300) is move to the raised position, the extension (1312) may be removed from the channel (1208), which may allow the implant to be advanced distally of the bumper plate (1300) as will be discussed in more detail below. While the delivery device (1200) is depicted in FIGS. 12A-12I and 13A-13D as having a bumper plate as an intermediate stop, it should be appreciated that in other variations the delivery device (1200) may comprise a plug or other component which may be removably connected to the cannula (1202) to limit advancement of the plunger (1206) to the extended position while the plug is connected to the cannula (1202). The plug may in turn be disconnected from the cannula (1202) to allow further advancement of the plunger (1206). Additionally, the plug may further comprise an extension positioned to extend into the channel (1208) when the plug is connected to the cannula (1202), which may temporarily prevent advancement of an implant relative to the plug, such as discussed above with respect to the extension (1312) of the bumper plate (1300).

Returning to FIGS. 12A-12H, the delivery device (1200) may comprise a tongue (1204) slidably connected to the cannula (1202), wherein the tongue (1204) extends at least partially through the channel (1208) of the cannula (1202). In some variations, the plunger portion (1228) of the plunger (1206) may be positioned between the tongue (1204) and the top wall (1214) of the cannula (1202). The tongue (1204) may be moved between a retracted position (as shown in FIGS. 12A-12D), in which a distal tip of the tongue (1204) is positioned in the channel (1208), and an advanced position (as shown in FIGS. 12E-12H), in which a distal tip of the tongue (1204) extends distally out of the outlet (1212) of the cannula (1202). In some of these variations, the tongue (1204) may extend distally of the distal tip of the blade (1218) of the cannula (1202) when the tongue is in the advanced position. As the distal tip of the tongue (1204) is advanced distally of the blade (1218), the tongue (1204) may further separate tissue to extend the length of the pocket.

In some variations, the tongue (1204) may comprise a handle (1240) at a proximal end thereof, which a user may grasp to facilitate movement of the tongue (1204) relative to the cannula (1202). In some instances, the handle (1240) of the tongue (1204) may limit movement of the tongue (1204) relative to the cannula (1202). For example, in some variations the handle (1240) may be sized such it may be prevented from entering the inlet (1210) of the channel (1208) of the cannula (1202). In these variations, the tongue (1204) may be advanced relative to the cannula (1202) until the handle (1240) of the tongue (1204) contacts the inlet (1210) (such as shown in FIGS. 12E-12H), which may prevent further advancement of the tongue (1204) and thereby set the advanced position of the tongue (1204).

Additionally or alternatively, in some variations the handle (1240) of the tongue (1204) may limit retraction of the tongue (1204) relative to the cannula (1202). For example, in the variation of the delivery device (1200) shown in FIGS. 12A-12H, the plunger (1206) may comprise a handle (1242) at a proximal end of the plunger (1206). In some variations, the handle (1240) of the tongue (1204) may be prevented from being withdrawn proximally of the handle (1242) of the plunger (1206). For example, in some of these variations, a portion of the handle (1240) of the tongue (1204) may at least partially surround the plunger (1206) to slidably connect the handle (1240) of the tongue (1204) to the plunger (1206). In these variations, the handle (1240) of the tongue (1204) may be withdrawn relative to the cannula (1202) and the plunger (1206) until the handle (1240) of the tongue (1204) reaches the handle (1242) of the plunger (1206), such as shown in FIGS. 12A-12D. The handle (1242) of the plunger (1206) may be sized or shaped such that the handle (1242) of the plunger (1206) prevents further withdrawal of the handle (1240) of the tongue (1204) when the handle (1240) of the tongue (1204) contacts the handle (1242) of the plunger (1206).

In some variations, the delivery device (1200) may further comprise a biasing member (1244) connected to the cannula (1202). Generally, the biasing member (1244) may comprise a piece of material (e.g., stainless steel, a nickel titanium alloy, or the like) that may have a first end connected to a bottom wall of the cannula (1202) and a free end that is biased toward the top wall (1214) of the channel (1208). In some variations, the biasing member (1244) may be sized such that the free end of the biasing member (1244) contacts the top wall (1214) of the cannula. When distal tip of the tongue (1204) is advanced out of the outlet (1212), the tongue (1204) may deflect the biasing member (1244) away from the top wall (1214) to allow the tongue (1204) to pass between the biasing member (1244) and the top wall (1214). When the tongue (1204) is positioned between the biasing member (1244) and the top wall (1214) (e.g., when the plunger (1206) is retracted and the tongue (1204) is advanced, such as shown in FIGS. 12F and 12H), the biasing member (1244) may press the tongue (1204) toward the top wall (1214) (and in some instance, may press a portion of the tongue (1204) into contact with the top wall (1214)). As the plunger (1206) is advanced relative to the cannula (1202), (such as shown in FIGS. 12E and 12G) the plunger (1206) may push the tongue (1204) away from the top wall (1214), which may further deflect the biasing member (1244) away from the top wall (1214) to allow the plunger (1206) to exit the outlet (1212).

The delivery device (1200) may be used to deliver an implant. Generally, the delivery device (1200) may be advanced toward the orbit of a patient, and the blade (1218) may pierce tissue of a patient to form an opening therein. In some variations the piercing tip (1220) of the blade (1218) may puncture the conjunctiva to form a tissue opening in the conjunctiva. In some of these variations, the method may comprise retracting an eyelid prior to piercing the conjunctiva. In other variations, the piercing tip (1220) of the blade (1218) may puncture the eyelid to form a tissue opening in the eyelid. The blade (1218) may be further advanced relative to the tissue opening to separate tissue beyond the tissue opening to form a pocket. In some variations, the blade (1218) may be advanced between the periosteum and the orbital bone to form a pocket therebetween. In other instances, the blade (1218) may be advanced between the periosteum and another tissue, such as the lacrimal gland, to form a pocket therebetween. In variations where the width of the blade (1218) tapers, advancement of the blade (1218) through the tissue opening may dilate the tissue opening. Additionally, in variations where the cannula (1202) comprises a stop bracket (1224), the delivery device (1200) may be advanced to advance the blade (1218) into tissue until the stop bracket (1224) contacts tissue (e.g., the skin overlying the orbital fossa), which may prevent or otherwise limit further advancement of the cannula (1202) relative to tissue.

The implant may also be loaded into the channel (1208) of the cannula (1202). In some variations, the implant may be loaded into the channel (1208) of the cannula (1202) prior to forming a tissue opening with the blade (1218). In other variations, the implant may be loaded into the channel (1208) after the blade (1218) has formed the tissue opening. In some variations, to load the implant into the cannula (1202), the plunger (1206) may be positioned in a retracted position (such as shown in FIGS. 12A-12D), and the implant may be inserted into the channel (1208) through the intermediate segment (1238) of the slot (1216). In variations where the delivery device (1200) comprises a bumper plate (1300) or other structure configured to limit advancement of the implant and/or plunger (1206), the plunger (1206) may be advanced relative to the channel to hold the implant into the channel. For example, when an implant is inserted into the channel (1208) through the intermediate segment (1238), the plunger (1206) may be advanced relative to the cannula with the bumper plate (1300) in the lowered position until the stopper portion (1230) of the plunger (1206) contacts the bumper plate (1300). In these instances, the bumper plate (1300) may temporarily prevent further advancement of the plunger (1206), which may prevent premature delivery of the implant from the delivery device (1200). Additionally, in variations where the bumper plate (1300) comprises an extension (1312) positioned to extend through the slot (1216) of the top wall (1214), the implant may be held between the distal end of the plunger portion (1228) and the extension (1312).

After the blade (1218) has formed a tissue opening, the tongue (1204) may be advanced relative to the cannula (1202) to advance a distal tip of the tongue (1204) out of the outlet (1212) of the channel (1208). In some of these variations, the distal tip of the tongue (1204) may be advanced distally of the distal tip of the blade (1218), such as shown in FIGS. 12F and 12H, which may extend the pocket further into the orbit of the patient. In variations where the tongue (1204) comprises a handle (1240), the tongue (1204) may be advanced until the handle (1240) contacts the inlet (1210) of the channel (1208).

With the tongue (1204) advanced, the plunger (1206) may be further advanced relative to the cannula (1202) to advance the implant out of the outlet (1212) of the channel (1208). Specifically, as the plunger portion (1228) is advanced through the channel (1208), a distal end of the plunger portion (1228) may contact and push the implant distally through the channel (1208). In variations where an intermediate stop (e.g., a bumper plate (1300), a plug, or the like) is positioned to temporarily prevent further advancement of the plunger (1206), the intermediate stop may be moved or disengaged to allow the plunger (1206) to be advanced. For example, in variations where the delivery device (1200) comprises a bumper plate (1300), the bumper plate (1300) may be moved to a raised position (e.g., by deflecting a release bracket (1308) to disengage the bumper plate (1300) as discussed in more detail above) to allow the plunger (1206) to be advanced past the bumper plate (1300). As the plunger (1206) is advanced, the plunger portion (1228) may push the implant between the tongue (1204) and the top wall (1214), which may advance the implant through the tissue opening and into the pocket.

In variations where the cannula (1202) has a stop bracket (1224) defining an aperture (1226) extending therethrough, the stopper portion (1230) may extend at least partially through the aperture (1226) to contact tissue during advancement of the plunger (1206). In some variations, the plunger (1206) may be sized such that when the stopper portion (1230) of the plunger (1206) engages tissue (e.g., to prevent further advancement of the plunger), the implant has been advanced out of the outlet (1212) of the channel (1208) of the cannula (1202), through the tissue opening, and into the pocket. A user may hold the plunger (1206) with the stopper portion (1230) in contact with the patient, and the cannula (1202) may be withdrawn relative to the plunger (1206) to remove the blade at least partially from the tissue opening and pocket. In instances where a handle (1240) of the tongue (1204) is in contact with an inlet (1210) of the channel (1208) of the cannula (1202), withdrawing the cannula (1202) may also withdraw the tongue (1204). In other variations, the tongue (1204) may be withdrawn prior to withdrawing the cannula (1202).

As the cannula (1202) and the tongue (1204) are withdrawn relative to plunger (1206), the plunger portion (1228) of the plunger (1206) may contact and hold the implant in place within the pocket, and thus may prevent the implant from being withdrawn with the cannula (1202) and the tongue (1204). In variations where the stopper portion (1230) of the plunger (1206) extends distally of a transition region, the cannula (1202) may be withdrawn relative to the plunger (1206) until the distal end of the slot (1216) engages the transition region, at which point further retraction of the cannula (1202) relative to the patient may also pull the plunger (1206) proximally relative to the patient, which may disengage the entire delivery device (1200) from the patient. Once the delivery device (1200) has been removed from the patient, the tissue opening may be closed in any suitable manner such as discussed in more detail above.

The delivery systems and devices described above with respect to FIGS. 7-13 may control placement of the implant relative to a patient. For example, in variations where the cannula comprises a stop bracket (such as stop bracket (1224) of cannula (1202) or stop bracket (814) of cannula (702), the distance between the stop bracket at the distal tip of the blade may control the depth of penetration of the blade into tissue. In some instances, the stop bracket (1224) may be used to help advanced the blade of the cannula at a certain angle relative to the orbit. Additionally, when a plunger (e.g., plunger (1206) of delivery device (1200) or plunger (708) of delivery system (700)) is used to advance the implant, the amount of advancement of the plunger relative to the cannula may control the depth of insertion of the implant. For example, when a portion of the plunger (e.g., a distal end of a transition region) may limit advancement of the plunger, this may help control the depth of insertion of the implant. Additionally, in variations where an implant is advanced between a top wall of a cannula and a tongue (e.g., tongue (706) of delivery system (700) or tongue (1204) of delivery system), this may help control the positioning of the implant between tissues. For example, when the blade of a cannula is advanced between tissues (e.g., between bone and the periosteum, between the periosteum and another anatomical location such as the lacrimal gland) to form a pocket therebetween, the tongue may be advanced along the top wall and blade of the cannula to position the tongue between the same tissues. As the implant is advanced between the blade and the tongue (which are both positioned between the same tissues), the implant may also be advanced between those tissues.

We claim:

1. A system comprising:

an implant; and a delivery device comprising a handle, a tongue member extending from the handle, a piercing member having a piercing tip, wherein the piercing member is moveable between a piercing configuration in which the piercing tip extends beyond a tip of the tongue member and a retracted configuration in which the piercing tip does not extend beyond the tip of the tongue member, and an ejector comprising a control slider, wherein the implant is releasably and slidably connected to the tongue member, wherein advancement of the control slider delivers the implant, and wherein retraction of the control slider is configured to move the piercing member from the retracted configuration to the piercing configuration.

2. The system of claim 1, wherein the tongue member is curved.

3. The system of claim 2, wherein the tongue member has a radius of curvature greater than or equal to 10 mm.

4. The system of claim 1, wherein the tongue member comprises one or more depth stops positioned along a length of the tongue member.

5. The system of claim 4, wherein the one or more depth stops comprises one or more projections.

6. The system of claim 4, wherein the one or more depth stops comprises one or more notches.

7. The system of claim 4, wherein the one or more depth stops comprises one or more markers.

8. The system of claim 1, wherein the tongue member comprises a tapered tip.

9. The system of claim 1, wherein the piercing member is biased toward the retracted configuration.

10. The system of claim 1, wherein the delivery device further comprises a rocker, wherein the rocker is rotatably connected to the handle, wherein the delivery device is configured such that rotation of the rocker in a first direction to a first position moves the piercing member to the piercing configuration, wherein the control slider is configured to rotate the rocker in the first direction, and wherein rotation of the rocker in a second direction opposite the first direction to a second position moves the piercing member to the retracted configuration.

11. The system of claim 10, wherein the rocker is biased toward the second position.

12. The system of claim 1, wherein the control slider is slidably attached to the handle.

13. The system of claim 12, wherein the ejector further comprises a pusher slidably attached to the tongue member, and a linkage connecting the control slider and the pusher.

* * * * *